US006833242B2

(12) United States Patent
Quake et al.

(10) Patent No.: US 6,833,242 B2
(45) Date of Patent: Dec. 21, 2004

(54) METHODS FOR DETECTING AND SORTING POLYNUCLEOTIDES BASED ON SIZE

(75) Inventors: Stephen R. Quake, San Marino, CA (US); Hou-Pu Chou, Foster City, CA (US)

(73) Assignee: California Institute of Technology, Pasadena, CA (US)

( * ) Notice: Subject to any disclaimer, the term of this patent is extended or adjusted under 35 U.S.C. 154(b) by 54 days.

(21) Appl. No.: 09/826,373

(22) Filed: Apr. 4, 2001

(65) Prior Publication Data

US 2002/0034748 A1 Mar. 21, 2002

Related U.S. Application Data

(63) Continuation-in-part of application No. 09/325,667, filed on May 21, 1999, now Pat. No. 6,540,895, and a continuation-in-part of application No. 08/932,774, filed on Sep. 23, 1997, now Pat. No. 6,221,564.
(60) Provisional application No. 60/194,422, filed on Apr. 4, 2000.

(51) Int. Cl.[7] ............................. C12Q 1/68; G01N 1/18; G01N 33/487

(52) U.S. Cl. ......................... 435/6; 435/91.1; 435/91.2; 435/287.2; 435/287.3; 435/286.5; 435/288.7
(58) Field of Search ........................ 435/6, 91.1, 91.2, 435/287.2, 287.3, 286.5, 288.7; 536/22.1, 24.2, 24.3

(56) References Cited

U.S. PATENT DOCUMENTS

| | | | |
|---|---|---|---|
| 4,581,624 A | 4/1986 | O'Connor | 357/26 |
| 4,585,209 A | 4/1986 | Aine et al. | 251/129 |
| 5,271,724 A | 12/1993 | Khuri-Yakub et al. | 73/597 |
| 5,417,235 A | 5/1995 | Wise et al. | 137/1 |
| 5,452,878 A | 9/1995 | Gravesen et al. | 251/129.02 |
| 5,800,690 A | 9/1998 | Chow et al. | 204/451 |
| 5,948,227 A | 9/1999 | Dubrow | 204/455 |
| 5,965,001 A | 10/1999 | Chow et al. | 204/600 |
| 6,007,690 A | 12/1999 | Nelson et al. | 204/601 |
| 6,042,709 A | 3/2000 | Parce et al. | 204/453 |
| 6,117,634 A * | 9/2000 | Langmore et al. | 435/6 |

FOREIGN PATENT DOCUMENTS

| | | | |
|---|---|---|---|
| EP | 0 778 351 | 6/1997 | C12Q/1/68 |
| GB | 2264296 | 8/1993 | C04B/35/82 |
| WO | 95/33853 | 12/1995 | C12Q/1/68 |
| WO | WO 98/52691 | 11/1998 | B01L/3/00 |

OTHER PUBLICATIONS

Angell, et al., "Silicon Micromechanical Devices," *Scientific American*, Apr. 1983, 248: pp. 44–55.
A. Ashkin et al. "Optical trapping and manipulation of single cells using infrared laser beams," *Nature*, Dec. 1987, vol. 330 24/31, pp. 769–771.
A. Ashkin et al., "Optical Trapping and Manipulation of Viruses and Bacteria," *Science*, Mar. 20, 1987, vol. 235, pp. 1518–1520.
J. P. Brody, et al., "Low Reynolds number micro– fluidic devices," *In Proc. of Solid–State Sensor and Actuator Workshop*, Jun. 1996, pp. 105–108.
Budowle et al., "Analysis of the VNTR Locus DIS80 by the PCR Followed by High–Resolution PAGE," *Am. J. Hum. Gent.*, 1991, vol. 48, pp. 137–144.
Castro, A., et al., "Fluorescence Detection and Size Measurement of Single DNA Molecules," *Analytical Chemistry*, Apr. 1, 1993, vol. 65, pp. 849–852.
Hou–Pu Chou, et al., "A microfabricated device for sizing and sorting DNA molecules," *PNAS*, Jan. 1999, vol. 96, pp. 11–13.
Thesis by Chou, H., "Microfabricated Devices for Rapid DNA Diagnostics," California Institute of Technology, May 30, 2000.
S. Fielder, et al., "Dielectrophoretic Sorting of Particles and Cells in a Microsystem," *Analytical Chemistry*, May, 1, 1998, vol. 70, pp. 1909–1915.
M. J. Fulwyer, "Electronic Separation of Biological Cells by Volume," *Science*, 1974, vol. 156, pp. 910–911.
Giusti, et al., "Application of Deoxyribonucleic Acid (DNA) Polymorphisms to the Anaylysis of DNA Recovered from Sperm," *Journal of Forsensic Science*, 1986, vol. 31, pp. 409–417.
Goodwin, P.M., et al., "Rapid sizing of individual fluorescently stained DNA fragments 6Y flow cytometry," *Nucleic Acids Research*, 1993, vol. 21, No. 4, pp. 803–806.
D.J. Harrison, et al., "Micromachining a Miniaturized Capillary Electrophoresis–Based Chemical Analysis System on a Chip," *Science*, Aug. 13, 1993, vol. 26, pp. 895–897.
Jeffreys et al., "Hypervariable 'minisatellite'regions in human DNA," *Nature*, Mar. 7, 1985, vol. 314, pp. 67–72.
Kanter et al., "Analysis of Restriction Fragment Length Polymorphisms in Deoxyribonucleic Acid (DNA) Recovered from Dried from Dried Bloodstains," *Journal of Forensic Sciences*, Apr. 1986, vol. 31, No. 2, pp. 389–408.
M. U. Kopp, et al., "Chemical amplification: Continuous–flow PCR on a chip," *Science*, May 15, 1998, vol. 280 (5366), pp. 1046–1048.

(List continued on next page.)

*Primary Examiner*—Carla J. Meyers
(74) *Attorney, Agent, or Firm*—Darby & Darby

(57) ABSTRACT

This invention relates in general to a method for molecular fingerprinting. The method can be used for forensic identification (e.g. DNA fingerprinting, especially by VNTR), bacterial typing, and human/animal pathogen diagnosis. More particularly, molecules such as polynucleotides (e.g. DNA) can be assessed or sorted by size in a microfabricated device that analyzes the polynucleotides according to restriction fragment length polymorphism. In a microfabricated device according to the invention, DNA fragments or other molecules can be rapidly and accurately typed using relatively small samples, by measuring for example the signal of an optically-detectable (e.g., fluorescent) reporter associated with the polynucleotide fragments.

16 Claims, 13 Drawing Sheets

OTHER PUBLICATIONS

Paul C. H. Li et al., "Transport, Manipulation, and Reaction of Biological Cells On–Chip Using Electrokinetic Effects," *Analytical Chemistry*, vol. 69, No. 8, pp. 1564–1568 Apr. 15, 1997.

Manz et al., "Micromachining of monocrystalline silicon and glass for chemical analysis systems," *Trends in Analytical Chemistry*, 1991, vol. 10, pp. 144–149.

Nakamura et al., "Variable Number of Tanden Repeat (VNTR) Markers for Human Gene Mapping," *Science*, Mar. 27, 1987, vol. 235, pp. 1616–1622.

J. P. Nolan, et al., "The emergence of flow cytometry for sensitive, real–time measurements of molecular interactions," *Nature Biotechnology*, Jul., 1998, vol. 16, pp. 633–638.

L.A. Sklar, "Sample handling for kinetics and molecular assembly in flow cytometry," *SPIE* 1998, vol. 3256, pp. 144–153.

Thompson, L.F., "Introduction to Micro Lithography," *ACS Symposium Series*, 1983, vol. 219, pp. 1–13.

M.A. Van Dilla et al., "Cell Microfluorometry: A Method for Rapid Fluorescence Measurement," *Science*, 1969, vol. 163, pp. 1213–1214.

G. Whitesides, Y. Xia, "Soft Lithography," *Angewandte Chemie International Edition* 37, 1998, vol. 37, pp. 550–575.

Tatri, et al., "HLA–Cw Allele Analysis by PCR–Restriction Fragment Length Polymorphism: Study of Known and Additional Alleies," *Proceedings of the National Academy of Sciences of The United States of America*, Sep. 1995, 92: pp. 8803–8807.

Ju, et al., "Application of Silver Staining to the Rapid Typing of the Polymorphism of HLA–DQ Alleles by Enzymatic Amplification and Allele–Specific Restriction Fragment Length Polymorphism," *Electrophoresis*, Apr. 1991, 12: pp. 270–273.

Murray, et al., "Detection of Polymorphisms Using Thermal Cycling With A Single Oligonucleotide On A DNA Sequencing Gel," *Human Mutation*, 1993, 2: pp. 118–122.

Chou, et al., "A Microfabricated Device for Sizing and Sorting DNA Molecules," *Proceedings of the National Academy of Sciences of The United States of America*, Jan. 1999, 96: pp. 11–13.

Rouhi, "Sizing, Sorting DNA One Piece At A Time," *Chemical and Engineering News, American Chemical Society*, Jan. 1999, 77: pp. 5–6.

* cited by examiner

METHODS FOR DETECTING AND SORTING POLYNUCLEOTIDES BASED ON SIZE

This application claims priority under 35 U.S.C. §119(e) to copending U.S. provisional patent application Ser. No. 60/194,422 filed on Apr. 4, 2000. The present application is also a continuation-in-part of U.S. patent application Ser. No. 08/932,774, now U.S. Pat. No. 6,221,564 and Ser. No. 09/325,667, now U.S. Pat. No. 6,540,895, filed on Sep. 23, 1997 and May 21, 1999, respectively. Each of these prior applications is hereby incorporated by reference in its entirety.

1. FIELD OF THE INVENTION

This invention relates in general to a method for molecular fingerprinting. The method can be used for forensic identification (e.g. DNA fingerprinting, especially by VNTR), bacterial typing, and human/animal pathogen diagnosis. More particularly, molecules such as polynucleotides (e.g. DNA) can be assessed or sorted by size in a microfabricated device that analyzes the polynucleotides according to restriction fragment length polymorphism. In a microfabricated device according to the invention, DNA fragments or other molecules can be rapidly and accurately typed using relatively small samples, by measuring for example the signal of an optically-detectable (e.g., fluorescent) reporter associated with the polynucleotide fragments.

More generally, the invention relates to a method of analyzing or sorting molecules such as polynucleotides (e.g., DNA) by size or some other characteristic. In particular, the invention relates to a method of analyzing and/or sorting individual polynucleotide molecules in a microfabricated device by measuring the signal of an optically-detectable (e.g., fluorescent, ultraviolet, radioactive or color change) reporter associated with the molecules. These methods and devices can also be adapted to analyze or sort cells or particles.

The devices and methods of the invention are advantageous, particularly in comparison with conventional gel electrophoresis techniques. For example, the invention provides less costly and more rapid equipment, can use smaller molecular samples, is less labor-intensive and is more readily automated. The invention is also advantageously flexible. Additional functions can be incorporated into the design as desired, such as in-line digestion, separation, etc.

2. BACKGROUND OF THE INVENTION

When DNA is broken into fragments using restriction enzymes, each of which cuts the DNA in a known way, the resulting DNA fragments or polypeptides of different sizes produce a unique pattern or profile which can be used to uniquely identify the source of the DNA molecules. In the invention, a reporter or other measurable signal varies as a function of molecule size, and in this way profiles based on size can be efficiently generated and compared, particularly on a small scale and in an automated or semi-automated fashion.

Methods enabling the matching of unidentified tissue samples to specific individuals have wide application in many fields. For DNA fingerprinting, commonly used methods include RFLP analysis (53, 54), variable nucleotide tandem repeats (55), and microsatellites (56). With the possible exception of monozygotic twins, each individual in the human population has a unique genetic composition which can be used to specifically identify each individual. This phenomenon has allowed law enforcement officials to use DNA sequence variation to determine, for example, whether a forensic sample was derived from any given individual. The fields of forensic and medical serology, paternity testing, and tissue and sample origin have seen increasing use of such techniques, including the forensic and diagnostic use of DNA sequence variation, e.g., statistical evaluations based on satellite sequences and variable number of tandem repeats (VNTRS) or amplified fragment length polymorphisms (AMP-FLPS). These methods are being used in crime laboratories, courts, hospitals and research and testing labs. Inclusion probabilities stated by the laboratories performing the analyses in such cases often exceed 1:1,000,000. That is, only one individual in one million is predicted, on a statistical basis, to have a given DNA "fingerprint" obtained by analyzing a pattern of DNA fragments generated according to these techniques.

The first implementation of DNA typing in forensics was Jeffreys' use of a multilocus DNA probe "fingerprint" that identified a suspect in a murder case in England. (55) In the United States, DNA profiling has been established using a battery of unlinked highly polymorphic single locus VNTR probes. (57) The use of these batteries of probes permits the development of a composite DNA profile for an individual. These profiles can be compared to databases, for example using the principles of Hardy-Weinberg to determine the probability of a match between a suspect and an unknown forensic sample.

Although these methods have markedly improved the power of the forensic and medical scientists to distinguish between individuals, they suffer from a number of shortcomings including a lack of sensitivity, the absence of internal controls, expense, time intensity, relatively large sample size, an inability to perform precise allele (gene pair) identification, and problems with identifying degraded DNA samples.

For example, the most frequently used method for forensic identification is the "Southern" hybridization technique, which has been widely used in forensic identification and medical diagnosis. Also called a "Southern blot," this technique treats an extracted molecule (a DNA sample) with a restriction endonuclease, an enzyme that cuts a polynucleotide chain wherever a specific and relatively short sequence of nucleic acids in the chain occurs. Examples of well known restriction enzymes used in this way are the endocucleases HaeIII, EcoRI, HpaI and HindIII. In DNA fingerprinting, restriction sites are typically used to isolate VNTRs (variable number of tandem repeats), which are regions in which a short sequence of DNA has been repeated a number of times. The number of repeating units within these regions vary between individuals, and when cut with a restriction endonuclease result in multiple fragments of different size called] RFLPs (restriction fragment length polymorphisms). These fragments can be used as a "fingerprint" because they vary in number and size from one individual to another.

The resulting nucleotide fragments (i.e. the RFLPs) are separated by size via gel electrophoresis, in which different sized charged molecules are separated by their different rates of movement through a stationary gel under the influence of an electric current. Following electrophoresis, the separated nucleotides are denatured and transferred to the surface of a nylon membrane by blotting; the so-called "Southern Blot". The Southern Blot is then incubated in a solution containing a radioactive single locus probe under conditions of temperature and salt concentration that favor hybridization. (A single locus probe is also called a "primer.") The locations of radioactive probe hybridization on the Southern Blot are detected and recorded via X-ray film or some other detection technique, thus providing a "profile" of the nucleotide. (Hybridization is used to pull out VNTR fragments, i.e. to separate them from irrelevant fragments.) In this approach, sample DNA is digested, and the resulting fragments are separated by size using gel electrophoresis. The separated fragments are transferred to a membrane by blotting, and are subjected to primer hybridization. (58)

This technique is time-consuming, labor intensive, and the gel may have a limited resolving power, making it potentially difficult to interpret the results. Another disadvantage is that these techniques generally require the use of a polymerase chain reaction (PCR) to multiply the polynucleotide in the sample. That is, the conventional tests are not very sensitive, and require relatively large DNA samples which often are not available. In such cases the sample concentration is increased to a meaningful detectable level by PCR. While this addresses some problems of sensitivity and sample degradation, PCR has been open to challenge because of possible sample contamination, and consequent undesirable amplification of contaminants leading to unreliable results. PCR approaches are also difficult to multiplex. For example, the probes and primers must be chosen with care, and generally only one set can be used. The sample may be consumed by one round of PCR, and different sets of probes or primers may require different reaction conditions, such as temperature. A simpler, more powerful technique is needed, which can accommodate small samples, does not rely on PCR, and which makes use of the most recent advances in DNA technology.

As described herein, the invention addresses these problems. In preferred embodiments a DNA sample is digested, primers are used to extend specifically desired DNA regions (e.g. VNTRs), without successive rounds of PCR, and highly sensitive or specific reporter molecules, such as fluorescently-labeled single nucleotides, are used to efficiently determine the length of the resulting DNA. A microfabricated or microfluidic device may be used to implement these techniques, for example to separate and optically detect labeled fragments.

The identification and separation of nucleic acid fragments by size, such as in sequencing of DNA or RNA, is a widely used technique in many fields, including molecular biology, biotechnology, and medical diagnostics. The most frequently used method for such separation is gel electrophoresis, in which different sized charged molecules are separated by their different rates of movement through a stationary gel under the influence of an electric current. Gel electrophoresis presents several disadvantages, however. The process can be time consuming, and resolution is typically about 10%. Efficiency and resolution decrease as the size of fragments increases; molecules larger than 40,000 base pairs are difficult to process, and those larger than 10 million base pairs cannot be distinguished.

Methods have been proposed for determination of the size of nucleic acid molecules based on the level of fluorescence emitted from molecules treated with a fluorescent dye. See Keller, et al., 1995 (31); Goodwin, et al., 1993 (28); Castro, et. al., 1993 (27); and Quake, et al., 1999 (59). Castro (27) describes the detection of individual molecules in samples containing either uniformly sized (48 Kbp) DNA molecules or a predetermined 1:1 ratio of molecules of two different sizes (48 Kbp and 24 Kbp). A resolution of approximately 12–15% was achieved between these two sizes. There is no discussion of sorting or isolating the differently sized molecules.

In order to provide a small diameter sample stream, Castro (27) uses a "sheath flow" technique wherein a sheath fluid hydrodynamically focuses the sample stream from 100 $\mu$m to 20 $\mu$m. This method requires that the radiation exciting the dye molecules, and the emitted fluorescence, must traverse the sheath fluid, leading to poor light collection efficiency and resolution problems caused by lack of uniformity. Specifically, this method results in a relatively poor signal-to-noise ratio of the collected fluorescence, leading to inaccuracies in the sizing of the DNA molecules.

Goodwin (28) mentions the sorting of fluorescently stained DNA molecules by flow cytometry. This method, however, employs costly and cumbersome equipment, and requires atomization of the nucleic acid solution into droplets, with the requirement that each droplet contains at most one analyte molecule. Furthermore, the flow velocities required for successful sorting of DNA fragments were determined to be considerably slower than used in conventional flow cytometry, so the method would require adaptations to conventional equipment. Sorting a usable amount (e.g., 100 ng) of DNA using such equipment would take weeks, if not months, for a single run, and would generate inordinately large volumes of DNA solution requiring additional concentration and/or precipitation steps.

Quake (59) relates to a single molecule sizing microfabricated device (SMS) for sorting polynucleotides or particles by size, charge or other identifying characteristics, for example, characteristics that can be optically detected. The invention includes a fluorescence activated sorter (FAS), and methods for analyzing and sorting polynucleotides by measuring a signal produced by an optically-detectable (e.g., fluorescent, ultraviolet or color change) reporter associated with the molecules. These methods and microfabricated devices allow for high sensitivity, no cross-contamination, and lower cost than conventional gel techniques. In one embodiment of the invention, it has been discovered that devices of this kind can be advantageously designed for use in molecular fingerprinting applications, such as DNA fingerprinting.

It is thus desirable to provide a method of rapidly analyzing and sorting differently sized nucleic acid molecules with high resolution, using simple and inexpensive equipment. In a microfabricated system, a short optical path length is desirable to reduce distortion and improve signal-to-noise of detected radiation. Ideally, sorting of fragments can be carried out using any size-based criteria.

3. SUMMARY OF THE INVENTION

The invention provides a molecular fingerprinting method and system, including for example microfabricated devices for sorting reporter-labeled polynucleotides or polynucleotide molecules by size.

An object of the present invention is a method for DNA fingerprinting using synthetic repeat polymorphisms.

An additional object of the present invention is a method for identifying the source of DNA in a forensic or medical sample.

A further object of the present invention is to provide an automated DNA profiling assay. This case be used, for example for DNA mapping, e.g. of BAC or YAC libraries.

An additional object of the present invention is to provide a kit for detecting synthetic repeat polymorphisms.

In accomplishing these and other objectives, the invention provides a method for molecular fingerprinting using a synthetic version of restriction fragment length polymorphism. The method includes choosing at random a short (20–50 bp) sequence of the polynucleotide that is a fixed distance away from a restriction site. This can be repeated any number of times for enhanced statistical discrimination, with different locations in the polynucleotide and different distances to a restriction site. Thus, a unique set of fragments can be generated, resulting in a fingerprint that can be obtained without relying on naturally occurring repeat sequences or restriction sites.

The method also provides for identification of a fingerprint in a sample. To identify a fingerprinted polynucleotide in a sample, an oligonucleotide (i.e. a short polynucleotide probe) is synthesized to complement the randomly chosen sequences. The probes are mixed with the sample along with nucleotide triphosphates and polymerase. The nucleotides can be fluorescently labeled. Through this technique a set of fluorescent strands of polynucleotide will be synthesized. Each complementary strand is cut with restriction enzymes to yield a polynucleotide of a fixed length. The polynucleotides can then be sized, either by gel electrophoresis or in a single molecule sizing device (SMS). One oligonucelotide probe derived from a references sample can be used, resulting in one complementary strand in a test sample containing matching sequences. If multiple oligonucleotides are designed, the reaction can be multiplexed and the different length fragments can be resolved into a multiple fragment fingerprint that can be compared to the standard or reference fingerprint. Preferably, a digestion is performed before enzyme/primer extension to prevent non-specific binding of primers. A six-base cutter (digestion enzyme) is particularly preferred to cut the sample into fragments of tens of thousands of base pairs. Alternatively, digestion after extension to fix the length can be performed.

A number of variations and modifications to this technique will be apparent to the practitioner of ordinary skill. For example, instead of using labeled nucleotides, complementary polynucleotides can be post-stained with an intercalating dye. Another variation is to use affinity purification to pull down the fragment of interest, i.e., using biotinylated oligonucleotides and streptavidin coated magnetic beads.

In a preferred embodiment, a microfabricated device is used for detecting or sorting the nucleotide fragments in a fingerprint based on size. The SMS device is fast, allowing analysis in as little as 10 minutes, and requires only femtograms of material, thus, the SMS device provides relatively high sensitivity without the need for PCR.

Mircofabricated Device. The device includes a chip having a substrate with at least one microfabricated analysis unit. Each analysis unit includes a main channel, having at one end a sample inlet, having along its length a detection region, and having, adjacent and downstream of the detection region, an outlet or a branch point discrimination region leading to a plurality of branch channels originating at the discrimination region and in communication with the main channel. The analysis unit also provides a stream of solution, preferably continuous, containing the molecules and passing through the detection region, such that on average only one molecule occupies the detection region at any given time. The level of reporter from each molecule is measured as it passes within the detection region. If desired, the molecule is directed to a selected branch channel based on the level of reporter.

In a preferred embodiment, the substrate is planar, and contains a microfluidic chip made from a silicone elastomer impression of an etched silicon wafer according replica methods in soft-lithography (11). In one embodiment, the channels meet to form a "T" (T junction). A Y-shaped junction, and other shapes and geometries may also be used. A detection region is typically upstream from the branch point. Molecules or cells are diverted into one or another outlet channel based on a predetermined characteristic that is evaluated as each cell passes through the detection region. The channels are preferably sealed to contain the flow, for example by fixing a transparent coverslip, such as glass, over the chip, to cover the channels while permitting optical examination of one or more channels or regions, particularly the detection region. In a preferred embodiment the coverslip is pyrex, anodically bonded to the chip.

Other devices such as electrophoresis chips may also be used. Exemplary devices are described in U.S. Pat. Nos. 6,042,709; 5,965,001; 5,948,227; 5,880,690; and 6,007,690.

Channel Dimensions. The channels in a molecular analysis device are preferably between about 1 $\mu$m and about 20 $\mu$m in width and between about 1 $\mu$m and about 20 $\mu$m in depth, and the detection region has a volume of between about 1 fl and about 1 pl. In a cell analysis device the channels are preferably between about 1 and 500 microns in width and between about 1 and 500 microns in depth, and the detection region has a volume of between about 1 fl and 100 nl. In preferred embodiments, the device includes a transparent (e.g., glass) cover slip bonded to the substrate and covering the channels to form the roof of the channels. The channels may be of any dimensions suitable to accommodate the largest dimension of the molecules to be analyzed.

Manifolds. A device which contains a plurality of analysis units may further include a plurality of manifolds, the number of such manifolds typically being equal to the number of branch channels in one analysis unit, to facilitate collection of molecules from corresponding branch channels of the different analysis units.

Flow of molecules. In one embodiment, the molecules are directed or sorted by electroosmotic force. A pair of electrodes apply an electric field or gradient across the discrimination region that is effective to move the flow of molecules through the device. In a sorting embodiment the electrodes can be switched to direct a particular molecule into a selected branch channel based on the amount of reporter signal detected from that molecule. In another embodiment, a flow of molecules is maintained through the device via a pump or pressure differential, and a valve structure can be used at the branch point effective to permit each molecule to enter only one selected branch channel. Alternatively, a valve can be placed in one or more channels downstream of the branch point to allow or curtail flow through each channel. In a related, pressure can be adjusted at the outlet of each branch channel effective to allow or curtail flow through the channel.

Optical Detection. Preferably the molecules are optically detectable when passing through the detection region. For example the molecules may be labeled with a reporter, for example a fluorescent reporter. The optically detectable signal can be measured, and generally is proportional to or is a function of a characteristic of the molecules, such as size or molecular weight. A fluorescent reporter, generating a quantitative optical signal can be used. Fluorescent reporters are known, and can be associated with molecules such as polynucleotides using known techniques.

In a preferred molecular fingerprinting embodiment, the reporter label is a fluorescently-labeled single nucleotides, such as fluorescein-dNTP, rhodamine-dNTP, Cy3-dNTP, Cy5-dNTP, where dNTP represents dATP, dTTP, dUTP or dCTP. The reporter can also be chemically-modified single nucleotides, such as biotin-dNTP. Alternatively, chemicals can be used that will react with an attached functional group such as biotin.

Sorting Molecules. In another aspect, the invention includes a method of isolating polynucleotides having a selected size. The method includes: a) flowing a continuous stream of solution containing reporter-labeled polynucleotides through a channel comprising a detection region having a selected volume, where the concentration of the molecules in the solution is such that the molecules pass through the detection region one-by-one, c) determining the size of each molecule as it passes through the detection region by measuring the level of the reporter, d) in the continuous stream of solution, diverting (i) molecules having the selected size into a first branch channel, and (ii) molecules not having the selected size into a second branch channel. Polynucleotides diverted into any channel can be collected as desired.

Flow Control In preferred embodiments, the concentration of polynucleotides in the solution is between about 10 fM and about 1 nM and the detection region volume is between about 1 fl and about 1 pl. The molecules can be diverted, for example, by transient application of an electric field effective to bias (i) a molecule having the selected size (e.g., between about 100 bp and about 10 mb) to enter one branch channel, and (ii) a molecule not having the selected size to enter another branch channel. Alternatively, molecules can be directed into a selected channel, based on size, by temporarily blocking the flow in other channels, such that the continuous stream of solution carries the molecule having the selected size into the selected channel. Pumps and valves may also be used to divert flow, and carry molecules into one or another channels, and mechanical switches may also be used. These methods can also be used in combination, and likewise molecules can be diverted based on whether they have a selected property or size, or do not have that property or size, or exceed or do not exceed a selected threshold measurement.

Synchronization. In each embodiment where molecules are measured and then diverted, as opposed to being measured only, the molecules are detected and measured one-by-one within the detection region, and are diverted one-by-one into the appropriate channels, by coordinating or synchronizing the diversion of flow with the detection step and with the flow entering the detection, as described for example in more detail below. In certain embodiments the flow rate may be adjusted, for example delayed, to maintain efficient detection and switching, and as described below the flow may in some cases be temporarily reversed to improve accuracy.

Sizing Molecules. In yet another aspect, the invention includes a method of sizing polynucleotides in solution. This method includes: a) flowing a continuous stream of solution containing reporter-labeled polynucleotides through a microfabricated channel comprising a detection region having a selected volume, where the concentration of the molecules in the solution is such that most molecules pass through the detection region one by one, and b) determining the size of each molecule as it passes through the detection region by measuring the level of the reporter.

Multiparameter Embodiments. In addition to analyzing or sorting fluorescent and non-fluorescent nucleotide fragments, the SMS can also provide multiparameter analysis. For example, sizing or sorting can be done according to a window or threshold value, meaning that molecules (e.g. polynucleotides) are selected based on the presence of a signal above or below a certain value or threshold. There can also be several points of analysis on the same chip for multiple time course measurements.

Thus, the invention provides for the rapid and accurate determination of the "profile" of a polynucleotide in high resolution using minimal amounts of material in these simple and inexpensive microfabricated devices. The methods and devices of the invention can replace or be used in combination with conventional gel based approaches.

5. DETAILED DESCRIPTION OF THE INVENTION

Definitions

Figure 1:
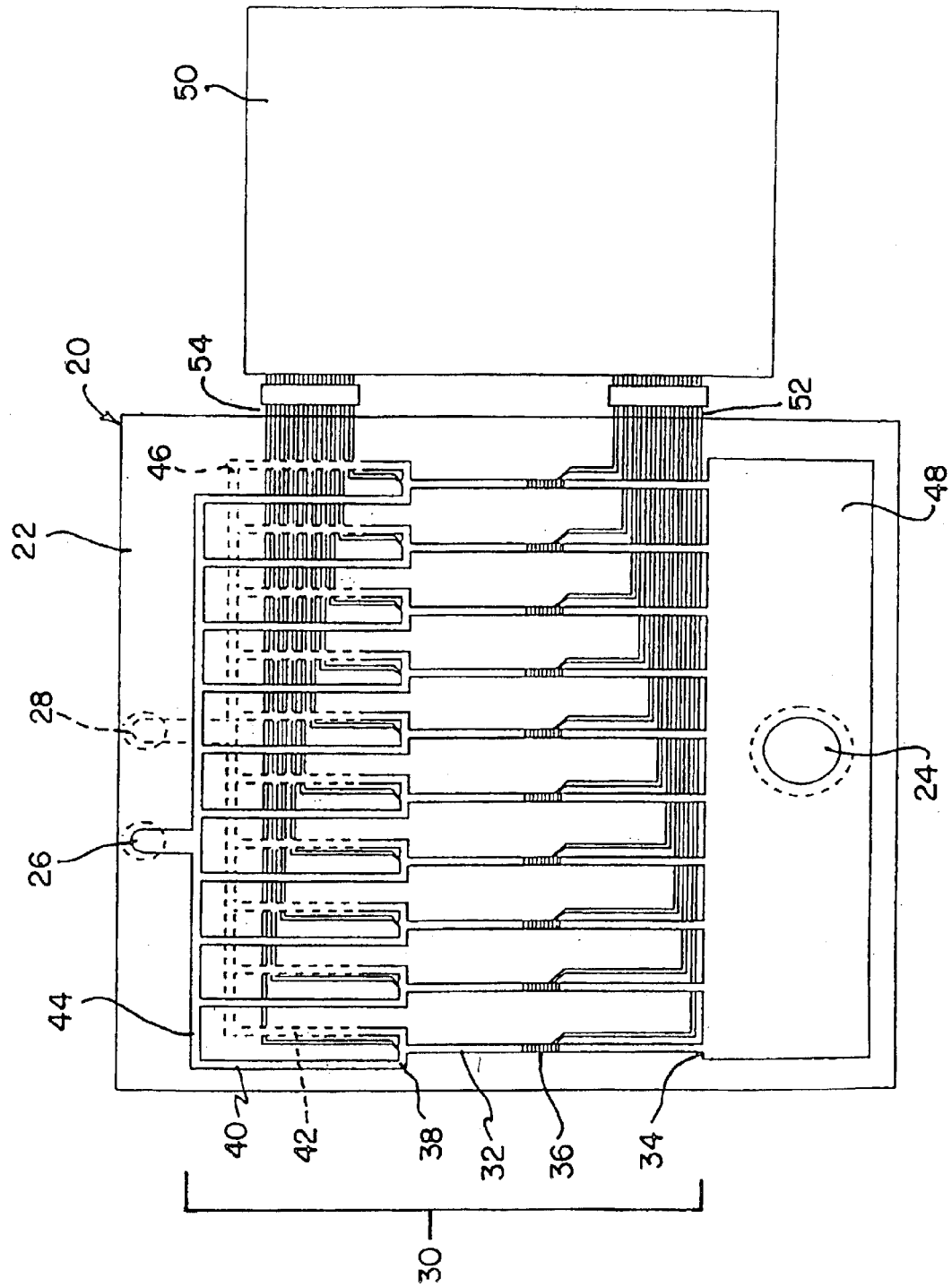
FIG. 1 shows a nucleic acid sorting device in accordance with one embodiment of the invention.

The terms used in this specification generally have their ordinary meanings in the art, within the context of the invention, and in the specific context where each term is used. Certain terms are discussed below, or elsewhere in the specification, to provide additional guidance to the practitioner in describing the devices and methods of the invention and how to make and use them. For convenience, certain terms are highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to the preferred embodiments.

General Definitions. As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate the presence of unrelated materials, i e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

Methods for purification are well-known in the art. For example, nucleic acids can be purified by precipitation, chromatography (including preparative solid phase chromatography, oligonucleotide hybridization, and triple helix chromatography), ultracentrifugation, and other means. Polypeptides and proteins can be purified by various methods including, without limitation, preparative disc-gel electrophoresis, isoelectric focusing, HPLC, reversed-phase HPLC, gel filtration, ion exchange and partition chromatography, precipitation and salting-out chromatography, extraction, and countercurrent distribution. For some purposes, it is preferable to produce the polypeptide in a recombinant system in which the protein contains an additional sequence tag that facilitates purification, such as, but not limited to, a polyhistidine sequence, or a sequence that specifically binds to an antibody, such as FLAG and GST. The polypeptide can then be purified from a crude lysate of the host cell by chromatography on an appropriate solid-phase matrix. Alternatively, antibodies produced against the protein or against peptides derived therefrom can be used as purification reagents. Cells can be purified by various techniques, including centrifugation, matrix separation (e.g., nylon wool separation), panning and other immunoselection techniques, depletion (e.g., complement depletion of contaminating cells), and cell sorting (e.g., fluorescence activated cell sorting which is also referred to as FACS). Other purification methods are possible. A purified material may contain less than about 50%, preferably less than about 75%, and most preferably less than about 90%, of the cellular components with which it was originally associated. The "substantially pure" indicates the highest degree of purity which can be achieved using conventional purification techniques known in the art.

A "sample" as used herein refers to a biological material which can be tested, e.g., for the presence of CK-2 polypeptides or CK-2 nucleic acids, e.g., to identify cells that specifically express the CK-2 gene and its gene product. Such samples can be obtained from any source, including tissue, blood and blood cells, including circulating hematopoietic stem cells (for possible detection of protein or nucleic acids), plural effusions, cerebrospinal fluid (CSF), ascites fluid, and cell culture. In preferred embodiments samples are obtained from bone marrow.

Non-human animals include, without limitation, laboratory animals such as mice, rats, rabbits, hamsters, guinea pigs, etc.; domestic animals such as dogs and cats; and, farm animals such as sheep, goats, pigs, horses, and cows.

In preferred embodiments, the terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The term "molecule" means any distinct or distinguishable structural unit of matter comprising one or more atoms, and includes, for example, polypeptides and polynucleotides.

As used herein, the term "cell" means any cell or cells (e.g., biological cells) as well as viruses or any other particle having a microscopic size; e.g., a size that similar to (such as having the same order of magnistude as) the size of a biological cell. The terms cell therefore encompasses both prokaryotic and eukaryotic cells; including bacteria, fungi, plant and animal cells. Cells are typically spherical, but can also be elongated, flattened, deformable and asymmetrical, i.e., non-spherical. The size or diameter of a cell typically ranges from about 0.1 to 120 microns, and typically is from about 1 to 50 microns. A cell may be living or dead. Since the microfabricated device of the invention is directed to sorting materials having a size similar to a biological cell (e.g. about 0.1 to 120 microns) any material having a size similar to a biological cell can be characterized and sorted using the microfabricated device of the invention. Thus, the term cell shall further include microscopic beads (such as chromatogrophic and fluorescent beads), liposomes, emulsions, or any other encapsulating biomaterials and porous materials. Non-limiting examples include latex, glass, or paramagnetic beads; and vesicles such as emulsions and liposomes, and other porous materials such as silica beads. Beads ranging in size from 0.1 micron to 1 mm can also be used, for example in sorting a library of compounds produced by combinatorial chemistry. As used herein, a cell may be charged or uncharged. For example, charged beads may be used to facilitate flow or detection, or as a reporter. Biological cells, living or dead, may be charged for example by using a surfactant, such as SDS (sodium dodecyl sulfate).

A "reporter" is any molecule, or a portion thereof, that is detectable, or measurable, for example, by optical detection. In addition, the reporter associates with a molecule or cell or with a particular marker or characteristic of the molecule or cell, or is itself detectable, to permit identification of the molecule or cell, or the presence or absence of a characteristic of the molecule or cell. In the case of molecules such as polynucleotides such characteristics include size, molecular weight, the presence or absence of particular constituents or moeties (such as particular nucleotide sequences or restrictions sites). The term "label" can be used interchangeably with "reporter". The reporter is typically a dye, fluorescent, ultraviolet, or chemiluminescent agent, chromophore, or radio-label, any of which may be detected with or without some kind of stimulatory event, e.g., fluoresce with or without a reagent. Typical reporters for molecular fingerprinting include without limitation fluorescently-labeled single nucleotides such as fluorescein-dNTP, rhodamine-dNTP, Cy3-dNTP, Cy5-dNTP, where dNTP represents dATP, dTTP, dUTP or dCTP. The reporter can also be chemically-modified single nucleotides, such as biotin-dNTP. Alternatively, chemicals can be used that react with an attached functional group such as biotin.

A "marker" is a characteristic of a molecule or cell that is detectable or is made detectable by a reporter, or which may be coexpressed with a reporter. For molecules, a marker can be particular constituents or moeties, such as restrictions sites or particular nucleic acid sequences in the case of polynucleotides. The marker may be directly or indirectly associated with the reporter or can itself be a reporter. Thus, a marker is generally a distinguishing feature of a molecule, and a reporter is generally an agent which directly or indirectly identifies or permits measurement of a marker. These terms may, however, be used interchangeably.

The term "flow" means any movement of liquid or solid through a device or in a method of the invention, and encompasses without limitation any fluid stream, and any material moving with, within or against the stream, whether or not the material is carried by the stream. For example, the movement of molecules or cells through a device or in a method of the invention, e.g. through channels of a microfluidic chip of the invention, comprises a flow. This is so, according to the invention, whether or not the molecules or cells are carried by a stream of fluid also comprising a flow, or whether the molecules or cells are caused to move by some other direct or indirect force or motivation, and whether or not the nature of any motivating force is known or understood. The application of any force may be used to provide a flow, including without limitation, pressure, capillary action, electro-osmosis, electrophoresis, dielectrophoresis, optical tweezers, and combinations thereof, without regard for any particular theory or mechanism of action, so long as molecules or cells are directed for detection, measurement or sorting according to the invention.

An "inlet region" is an area of a microfabricated chip that receives molecules or cells for detection measurement or sorting. The inlet region may contain an inlet channel, a well or reservoir, an opening, and other features which facilitate the entry of molecules or cells into the device. A chip may contain more than one inlet region if desired. The inlet region is in fluid communication with the main channel and is upstream therefrom.

An "outlet region" is an area of a microfabricated chip that collects or dispenses molecules or cells after detection, measurement or sorting. An outlet region is downstream from a discrimination region, and may contain branch channels or outlet channels. A chip may contain more than one outlet region if desired.

An "analysis unit" is a microfabricated substrate, e.g., a microfabricated chip, having at least one inlet region, at least one main channel, at least one detection region and at least one outlet region. Sorting embodiments of the analysis unit include a discrimination region and/or a branch point, e.g. downstream of the detection region, that forms at least two branch channels and two outlet regions. A device of the invention may comprise a plurality of analysis units.

A "main channel" is a channel of the chip of the invention which permits the flow of molecules or cells past a detection region for detection (identification), measurement, or sorting. In a chip designed for sorting, the main channel also comprises a discrimination region. The detection and discrimination regions can be placed or fabricated into the main channel. The main channel is typically in fluid communication with an inlet channel or inlet region, which permit the flow of molecules or cells into the main channel. The main channel is also typically in fluid communication with an outlet region and optionally with branch channels, each of which may have an outlet channel or waste channel. These channels permit the flow of cells out of the main channel.

A "detection region" is a location within the chip, typically within the main channel where molecules or cells to be identified, measured or sorted are examined on the basis of a predetermined characteristic. In a preferred embodiment, molecules or cells are examined one at a time, and the characteristic is detected or measured optically, for example, by testing for the presence or amount of a reporter. For example, the detection region is in communication with one or more microscopes, diodes, light stimulating devices, (e.g., lasers), photomultiplier tubes, and processors (e.g., computers and software), and combinations thereof, which cooperate to detect a signal representative of a characteristic, marker, or reporter, and to determine and direct the measurement or the sorting action at the discrimination region. In sorting embodiments the the detection region is in fluid communication with a discrimination region and is at, proximate to, or upstream of the discrimination region.

A "discrimination region" or "branch point" is a junction of a channel where the flow of molecules or cells can change direction to enter one or more other channels, e.g., a branch channel, depending on a signal received in connection with an examination in the detection region. Typically, a discrimination region is monitored and/or under the control of a detection region, and therefore a discrimination region may "correspond" to such detection region. The discrimination region is in communication with and is influenced by one or more sorting techniques or flow control systems, e.g., electric, electro-osmotic, (micro-) valve, etc. A flow control system can employ a variety of sorting techniques to change or direct the flow of molecules or cells into a predetermined branch channel.

A "branch channel" is a channel which is in communication with a discrimination region and a main channel. Typically, a branch channel receives molecules or cells depending on the molecule or cell characteristic of interest as detected by the detection region and sorted at the discrimination region. A branch channel may be in communication with other channels to permit additional sorting. Alternatively, a branch channel may also have an outlet region and/or terminate with a well or reservoir to allow collection or disposal of the molecules or cells.

The term "forward sorting" or flow describes a one-direction flow of molecules or cells, typically from an inlet region (upstream) to an outlet region (downstream), and preferably without a change in direction, e.g., opposing the "forward" flow. Preferably, molecules or cells travel forward in a linear fashion, i.e., in single file. A preferred "forward" sorting algorithm consists of running molecules or cells from the input channel to the waste channel, until a molecule or cell is identified to have an optically detectable signal (e.g. fluorescence) that is above a pre-set threshold, at which point voltages are temporarily changed to electroosmotically divert the molecule or to the collection channel.

The term "reversible sorting" or flow describes a movement or flow that can change, i.e., reverse direction, for example, from a forward direction to an opposing backwards direction. Stated another way, reversible sorting permits a change in the direction of flow from a downstream to an upstream direction. This may be useful for more accurate sorting, for example, by allowing for confirmation of a sorting decision, selection of particular branch channel, or to correct an improperly selected channel.

Different algorithms for sorting in the microfluidic device can be implemented by different programs, for example under the control of a personal computer. As an example, consider a pressure-switched scheme instead of electro-osmotic flow. Electro-osmotic switching is virtually instantaneous and throughput is limited by the highest voltage that can be applied to the sorter (which also affects the run time through ion depletion effects). A pressure switched-scheme does not require high voltages and is more robust for longer runs. However, mechanical compliance in the system is likely to cause the fluid switching speed to become rate-limiting with the "forward" sorting program. Since the fluid is at low Reynolds number and is completely reversible, when trying to separate rare molecules or cells one can implement a sorting algorithm that is not limited by the intrinsic switching speed of the device. The molecules or cells flow at the highest possible static (non-switching) speed from the input to the waste. When an interesting molecule or cell is detected, the flow is stopped. By the time the flow stops, the molecule or cell may be past the junction and part way down the waste channel. The system is then run backwards at a slow (switchable) speed from waste to input, and the molecule or cell is switched to the collection channel when it passes through the detection region. At that point, the molecule or cell is "saved" and the device can be run at high speed in the forward direction again. Similarly, an device of the invention that is used for analysis, without sorting, can be run in reverse to re-read or verify the detection or analysis made for one or more molecules or cells in the detection region. This "reversible" analysis or sorting method is not possible with standard gel electrophoresis technologies (for molecules) nor with conventional FACS machines (for cells). Reversible algorithms are particularly useful for collecting rare molecules or cells or making multiple time course measurements of a molecule or single cell.

Molecular Biology Definitions. In accordance with the present invention, there may be employed conventional molecular biology, microbiology and recombinant DNA techniques within the skill of the art. Such techniques are explained fully in the literature. See, for example, Sambrook, Fitsch & Maniatis, *Molecular Cloning: A Laboratory Manual*, Second Edition (1989) Cold Spring Harbor Laboratory Press, Cold Spring Harbor, N.Y. (referred to herein as "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins, eds. 1984); *Animal Cell Culture* (R. I. Freshney, ed. 1986); *Immobilized Cells and Enzymes* (IRL Press, 1986); B. E. Perbal, *A Practical Guide to Molecular Cloning* (1984); F. M. Ausubel et al. (eds.), *Current Protocols in Molecular Biology*, John Wiley & Sons, Inc. (1994).

The term "polymer" means any substance or compound that is composed of two or more building blocks ('mers') that are repetitively linked together. For example, a "dimer" is a compound in which two building blocks have been joined together; a "trimer" is a compound in which three building blocks have been joined together; etc.

The term "polynucleotide" or "nucleic acid molecule" as used herein refers to a polymeric molecule having a backbone that supports bases capable of hydrogen bonding to typical polynucleotides, wherein the polymer backbone presents the bases in a manner to permit such hydrogen bonding in a specific fashion between the polymeric molecule and a typical polynucleotide (e.g., single-stranded DNA). Such bases are typically inosine, adenosine, guanosine, cytosine, uracil and thymidine. Polymeric molecules include "double stranded" and "single stranded" DNA and RNA, as well as backbone modifications thereof (for example, methylphosphonate linkages).

Thus, a "polynucleotide" or "nucleic acid" sequence is a series of nucleotide bases (also called "nucleotides"), generally in DNA and RNA, and means any chain of two or more nucleotides. A nucleotide sequence frequently carries genetic information, including the information used by cellular machinery to make proteins and enzymes. The terms include genomic DNA, cDNA, RNA, any synthetic and genetically manipulated polynucleotide, and both sense and antisense polynucleotides. This includes single- and double-stranded molecules; i.e., DNA-DNA, DNA-RNA, and RNA-RNA hybrids as well as "protein nucleic acids" (PNA) formed by conjugating bases to an amino acid backbone. This also includes nucleic acids containing modified bases, for example, thio-uracil, thio-guanine and fluoro-uracil.

The polynucleotides herein may be flanked by natural regulatory sequences, or may be associated with heterologous sequences, including promoters, enhancers, response elements, signal sequences, polyadenylation sequences, introns, 5'- and 3'-non-coding regions and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.) and alkylators to name a few. The polynucleotides may be derivatized by formation of a methyl or ethyl phosphotriester or an alkyl phosphoramidite linkage. Furthermore, the polynucleotides herein may also be modified with a label capable of providing a detectable signal, either directly or indirectly. Exemplary labels include radioisotopes, fluorescent molecules, biotin and the like. Other non-limiting examples of modification which may be made are provided, below, in the description of the present invention.

As used herein, the term "oligonucleotide" refers to a nucleic acid, generally of at least 10, preferably at least 15, and more preferably at least 20 nucleotides, preferably no more than 100 nucleotides, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}$P-nucleotides or nucleotides to which a label, such as biotin or a fluorescent dye (for example, Cy3 or Cy5) has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of a particular nucleic acid (e.g., a particular gene or a particular gene sequence), or to detect the presence of particular nucleic acids (e.g., of a particular gene or a particular gene sequence). Generally, oligonucleotides are prepared synthetically, preferably on a nucleic acid synthesizer. Accordingly, oligonucleotides can be prepared with non-naturally occurring phosphoester analog bonds, such as thioester bonds, etc.

Specific non-limiting examples of synthetic nucleotides (including polynucleotides and oligonucleotides) envisioned for this invention include, in addition to the nucleic acid moieties described above, oligonucleotides that contain phosphorothioates, phosphotriesters, methyl phosphonates, short chain alkyl, or cycloalkyl intersugar linkages or short chain heteroatomic or heterocyclic intersugar linkages. Most preferred are those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—$PO_2$—O—$CH_2$). U.S. Pat. No. 5,677,437 describes heteroaromatic olignucleoside linkages. Nitrogen linkers or groups containing nitrogen can also be used to prepare oligonucleotide mimics (U.S. Pat. Nos. 5,792,844 and 5,783,682). U.S Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., Science 254:1497, 1991). Other synthetic oligonucleotides may contain substituted sugar moieties comprising one of the following at the 2' position: OH, SH, $SCH_3$, F, OCN, $O(CH_2)_n$ $NH_2$ or $O(CH_2)_n$ $CH_3$ where n is from 1 to about 10; $C_1$ to $C_{10}$ lower alkyl, substituted lower alkyl, alkaryl or aralkyl; Cl; Br; CN; $CF_3$; $OCF_3$; O—; S—, or N—alkyl; O—, S—, or N—alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substitued silyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties. Oligonucleotides may also have sugar mimetics such as cyclobutyls or other carbocyclics in place of the pentofaranosyl group. Nucleotide units having nucleosides other than adenosine, cytidine, guanosine, thymidine and uridine, such as inosine, may be used in an oligonucleotide molecule.

A "polypeptide" is a chain of chemical building blocks called amino acids that are linked together by chemical bonds called "peptide bonds". The term "protein" refers to polypeptides that contain the amino acid residues encoded by a gene or by a nucleic acid molecule (e.g., an mRNA or a cDNA) transcribed from that gene either directly or indirectly. Optionally, a protein may lack certain amino acid residues that are encoded by a gene or by an mRNA. For example, a gene or mRNA molecule may encode a sequence of amino acid residues on the N-terminus of a protein (i.e., a signal sequence) that is cleaved from, and therefore may not be part of, the final protein. A protein or polypeptide, including an enzyme, may be a "native" or "wild-type", meaning that it occurs in nature; or it may be a "mutant", "variant" or "modified", meaning that it has been made, altered, derived, or is in some way different or changed from a native protein or from another mutant.

"Amplification" of a polynucleotide, as used herein, denotes the use of polymerase chain reaction (PCR) to increase the concentration of a particular DNA sequence within a mixture of DNA sequences. For a description of PCR see Saiki et al., *Science* 1988, 239:487.

"Chemical sequencing" of DNA denotes methods such as that of Maxam and Gilbert (Maxam-Gilbert sequencing; see Maxam & Gilbert, *Proc. Natl. Acad. Sci. U.S.A.* 1977, 74:560), in which DNA is cleaved using individual base-specific reactions.

"Enzymatic sequencing" of DNA denotes methods such as that of Sanger (Sanger et al., *Proc. Natl. Acad. Sci. U.S.A.* 1977, 74:5463) and variations thereof well known in the art, in a single-stranded DNA is copied and randomly terminated using DNA polymerase.

A "gene" is a sequence of nucleotides which code for a functional "*gene product*". Generally, a gene product is a functional protein. However, a gene product can also be another type of molecule in a cell, such as an RNA (e.g., a tRNA or a rRNA). For the purposes of the present invention, a gene product also refers to an mRNA sequence which may be found in a cell. For example, measuring gene expression levels according to the invention may correspond to measuring mRNA levels. A gene may also comprise regulatory (i.e., non-coding) sequences as well as coding sequences. Exemplary regulatory sequences include promoter sequences, which determine, for example, the conditions under which the gene is expressed. The transcribed region of the gene may also include untranslated regions including introns, a 5'-untranslated region (5'-UTR) and a 3'-untranslated region (3'-UTR).

A "coding sequence" or a sequence "encoding" an expression product, such as a RNA, polypeptide, protein or enzyme, is a nucleotide sequence that, when expressed, results in the production of that RNA, polypeptide, protein or enzyme; i.e., the nucleotide sequence "encodes" that RNA or it encodes the amino acid sequence for that polypeptide, protein or enzyme.

A "promoter sequence" is a DNA regulatory region capable of binding RNA polymerase in a cell and initiating transcription of a downstream (3' direction) coding sequence. For purposes of defining the present invention, the promoter sequence is bounded at its 3'terminus by the transcription initiation site and extends upstream (5' direction) to include the minimum number of bases or elements necessary to initiate transcription at levels detectable above background. Within the promoter sequence will be found a transcription initiation site (conveniently found, for example, by mapping with nuclease S1), as well as protein binding domains (consensus sequences) responsible for the binding of RNA polymerase.

A coding sequence is "under the control of" or is "operatively associated with" transcriptional and translational control sequences in a cell when RNA polymerase transcribes the coding sequence into RNA, which is then trans-RNA spliced (if it contains introns) and, if the sequence encodes a protein, is translated into that protein.

The term "express" and "expression" means allowing or causing the information in a gene or DNA sequence to become manifest, for example producing RNA (such as rRNA or mRNA) or a protein by activating the cellular functions involved in transcription and translation of a corresponding gene or DNA sequence. A DNA sequence is expressed by a cell to form an "expression product" such as an RNA (e.g., a mRNA or a rRNA) or a protein. The expression product itself, e.g., the resulting RNA or protein, may also said to be "expressed" by the cell.

The term "transfection" means the introduction of a foreign nucleic acid into a cell. The term "transformation" means the introduction of a "foreign" (i.e., extrinsic or extracellular) gene, DNA or RNA sequence into a host cell so that the host cell will express the introduced gene or sequence to produce a desired substance, in this invention typically an RNA coded by the introduced gene or sequence, but also a protein or an enzyme coded by the introduced gene or sequence. The introduced gene or sequence may also be called a "cloned" or "foreign" gene or sequence, may include regulatory or control sequences (e.g., start, stop, promoter, signal, secretion or other sequences used by a cell's genetic machinery). The gene or sequence may include nonfunctional sequences or sequences with no known function. A host cell that receives and expresses introduced DNA or RNA has been "transformed" and is a "transformant" or a "clone". The DNA or RNA introduced to a host cell can come from any source, including cells of the same genus or species as the host cell or cells of a different genus or species.

The terms "vector", "cloning vector" and "expression vectors" mean the vehicle by which a DNA or RNA sequence (e.g., a foreign gene) can be introduced into a host cell so as to transform the host and promote expression (e.g., transcription and translation) of the introduced sequence. Vectors may include plasmids, phages, viruses, etc. and are discussed in greater detail below.

A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily introduced into a suitable host cell. A large number of vectors, including plasmid and fungal vectors, have been described for replication and/or expression in a variety of eukaryotic and prokaryotic hosts. The term "host cell" means any cell of any organism that is selected, modified, transformed, grown or used or manipulated in any way for the production of a substance by the cell. For example, a host cell may be one that is manipulated to express a particular gene, a DNA or RNA sequence, a protein or an enzyme. Host cells can further be used for screening or other assays that are described infra. Host cells may be cultured in vitro or one or more cells in a non-human animal (e.g., a transgenic animal or a transiently transfected animal).

The term "expression system" means a host cell and compatible vector under suitable conditions, e.g. for the expression of a protein coded for by foreign DNA carried by the vector and introduced to the host cell. Common expression systems include *E. coli* host cells and plasmid vectors, insect host cells such as Sf9, Hi5 or S2 cells and Baculovirus vectors, Drosophila cells (Schneider cells) and expression systems, fish cells and expression systems (including, for example, RTH-149 cells from rainbow trout, which are available from the American Type Culture Collection and have been assigned the accession no. CRL-1710) and mammalian host cells and vectors.

The term "heterologous" refers to a combination of elements not naturally occurring. For example, the present invention includes chimeric RNA molecules that comprise an rRNA sequence and a heterologous RNA sequence which is not part of the rRNA sequence. In this context, the heterologous RNA sequence refers to an RNA sequence that is not naturally located within the ribosomal RNA sequence. Alternatively, the heterologous RNA sequence may be naturally located within the ribosomal RNA sequence, but is found at a location in the rRNA sequence where it does not naturally occur. As another example, heterologous DNA refers to DNA that is not naturally located in the cell, or in a chromosomal site of the cell. Preferably, heterologous DNA includes a gene foreign to the cell. A heterologous expression regulatory element is a regulatory element operatively associated with a different gene that the one it is operatively associated with in nature.

The terms "mutant" and "mutation" mean any detectable change in genetic material, e.g., DNA, or any process, mechanism or result of such a change. This includes gene mutations, in which the structure (e.g., DNA sequence) of a gene is altered, any gene or DNA arising from any mutation process, and any expression product (e.g., RNA, protein or enzyme) expressed by a modified gene or DNA sequence. The term "variant" may also be used to indicate a modified or altered gene, DNA sequence, RNA, enzyme, cell, etc.; i.e., any kind of mutant. For example, the present invention relates to altered or "chimeric" RNA molecules that comprise an rRNA sequence that is altered by inserting a heterologous RNA sequence that is not naturally part of that sequence or is not naturally located at the position of that rRNA sequence. Such chimeric RNA sequences, as well as DNA and genes that encode them, are also referred to herein as "mutant" sequences.

The term "homologous", in all its grammatical forms and spelling variations, refers to the relationship between two proteins that possess a "common evolutionary origin", including proteins from superfamilies (e.g., the immunoglobulin superfamily) in the same species of organism, as well as homologous proteins from different species of organism (for example, myosin light chain polypeptide, etc.; see, Reeck et al., Cell 1987, 50:667). Such proteins (and their encoding nucleic acids) have sequence homology, as reflected by their sequence similarity, whether in terms of percent identity or by the presence of specific residues or motifs and conserved positions.

The term "sequence similarity", in all its grammatical forms, refers to the degree of identity or correspondence between nucleic acid or amino acid sequences that may or may not share a common evolutionary origin (see, Reeck et al., supra). However, in common usage and in the instant application, the term "homologous", when modified with an adverb such as "highly", may refer to sequence similarity and may or may not relate to a common evolutionary origin.

In specific embodiments, two nucleic acid sequences are "substantially homologous" or "substantially similar" when at least about 80%, and more preferably at least about 90% or at least about 95% of the nucleotides match over a defined length of the nucleic acid sequences, as determined by a sequence comparison algorithm known such as BLAST, FASTA, DNA Strider, CLUSTAL, etc. An example of such a sequence is an allelic or species variant of the specific genes of the present invention. Sequences that are substantially homologous may also be identified by hybridization, e.g., in a Southern hybridization experiment under, e.g., stringent conditions as defined for that particular system.

Similarly, in particular embodiments of the invention, two amino acid sequences are "substantially homologous" or "substantially similar" when greater than 80% of the amino acid residues are identical, or when greater than about 90% of the amino acid residues are similar (i.e., are functionally identical). Preferably the similar or homologous polypeptide sequences are identified by alignment using, for example, the GCG (Genetics Computer Group, Program Manual for the GCG Package, Version 7, Madison Wis.) pileup program, or using any of the programs and algorithms described above (e.g., BLAST, FASTA, CLUSTAL, etc.).

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al ., supra). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. SCC is a 0.15 M NaCl, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–9.51). For hybridization with shorter nucleic acids, i.e., oligonucleotides, the position of mismatches becomes more important, and the length of the oligonucleotide determines its specificity (see Sambrook et al., supra, 11.7–11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2× SSC, at 42° C. in 50% formamide, 4×SSC, or under conditions that afford levels of hybridization equivalent to those observed under either of these two conditions.

Suitable hybridization conditions for oligonucleotides (e.g., for oligonucleotide probes or primers) are typically somewhat different than for full-length nucleic acids (e.g., full-length cDNA), because of the oligonucleotides'lower melting temperature. Because the melting temperature of oligonucleotides will depend on the length of the oligonucleotide sequences involved, suitable hybridization temperatures will vary depending upon the oligoncucleotide molecules used. Exemplary temperatures may be 37° C. (for 14-base oligonucleotides), 48° C. (for 17-base oligoncucleotides), 55° C. (for 20-base oligonucleotides) and 60° C. (for 23-base oligonucleotides). Exemplary suitable hybridization conditions for oligonucleotides include washing in 6×SSC/0.05% sodium pyrophosphate, or other conditions that afford equivalent levels of hybridization.

5.2. Overview of the Invention

The invention provides a method and system for molecular fingerprinting, and devices for molecular fingerprinting, including microfabricated microfluidic devices for evaluating or sorting molecules according to size. More particularly, polynucleotides such as DNA samples can be fragmented, for example using endonucleases, to produce a set of fragments that vary in size. The size distribution of these fragments (e.g. the number of fragments of each size over a range of sizes) may uniquely identify the source of the sample. Some or all of the fragments can be selected to serve as a "fingerprint" of the sample. Further, fragments comprising the fingerprint can be labeled, for example with a reporter molecule such as fluorescent marker, so that the they can be more readily detected, measured or sorted.

These measurements can be detected by any suitable means, preferably optical, and can be stored for example in a computer as a representation of the fragments comprising the fingerprint. Depending on the strategy for producing the fragments which comprise a fingerprint, oligonucleotide probes of known composition and length may be used to "tag" or label the fragments. For example, probes having sequences that are complementary to each of the fragments can be made by combining the fragments with labeled nucleotide bases in the presence of a polymerase, which is an enzyme that assembles a single strand of complementary polynucleotide using another strand (i.e. a fingerprint fragment) as a template. The nucleotide bases used to make these probes may be radioactive, or can be labeled with a fluorescent marker, or with some other readily detectable reporter. The resulting probes can be used to record a fingerprint of the sample, by detecting and measuring the lever of reporter as an indication of size, or by sorting the probes according to size.

Labeled or unlabeled probes can also be used to "fish out" matching polynucleotides from a test sample containing unknown DNA or polynucleotides. Under appropriate hybridizing conditions, probes will bind to matching fragments in a sample. This can provide a way to test for a match, for example when the probes comprising a fingerprint hybridize to complementary fragments in the sample.

According to one aspect of the invention polynucleotides can be fingerprinted using a synthetic version of restriction fragment length polymorphism. The method includes choosing at random a short (20–50 bp) sequence of the polynucleotide that is a fixed distance away from a restriction site. This can be repeated any number of times for enhanced statistical discrimination, with different locations in the polynucleotide and different distances to a restriction site. Samples are digested with a specific restriction enzyme, such as Bg II, EcoR I, Hind III or Xho I. A final mixture of DNA fragments of thousands of base pairs is preferred. In this way a unique fingerprint can be synthesized without relying on naturally occurring repeat sequences or restriction sites.

The method also provides for identification of the fingerprinted nucleotide in a sample. To identify the fingerprinted polynucleotide in a sample, an oligonucleotide probe is synthesized to complement each randomly chosen sequence. Each probe is mixed with the test sample along with nucleotide triphosphates and polymerase. The nucleotides can be fluorescently labeled. Through this technique a fluorescent strand of polynucleotide (complementary to each probe) will be synthesized. Each strand is then cut with restriction enzymes to yield a polynucleotide of a fixed length. The polynucleotide can then be sized, either by gel electrophoresis or in a single molecule sizing device (SMS) (59). If multiple oligonucleotides are designed, the reaction can be multiplexed and the different length fragments can then be resolved into a fingerprint that can be compared to a standard fingerprint.

In one aspect of the invention, polynucleotides, e.g., DNA, can be detected, sized or sorted dynamically in a continuous flow stream of microscopic dimensions based for example on molecular weight, using a microfabricated polynucleotide sorting device. The polynucleotides, suspended in a suitable carrier fluid (e.g., $ddH_2O$ or TE), are introduced into an inlet end of a narrow channel in the sorting device. The molecular weight of each molecule is calculated from the intensity of signal from an optically-detectable reporter incorporated into or associated with the polynucleotide molecule as the molecule passes through a "detection window" or "detection region" in the device.

In a sorter embodiment, molecules having a molecular weight falling within a selected range are diverted into a selected output or "branch" channel of the device. The sorted polynucleotide molecules may be collected from the output channels and used in subsequent manipulations.

According to another aspect of the invention, a device such as described above, but not necessarily including components for sorting the molecules, can be used to measure or quantify the size range of polynucleotides in a sample, and store or feed this information into a processor or computer for subsequent analysis or display, e.g., as a size distribution histogram. Such a device enables the generation of the type of polynucleotide fragment length data now commonly obtained from analytical gels, such as agarose or polyacrylamide gels, or from Southern blot results, in a fraction of the time required for preparation and analysis of gels, and using a substantially smaller amount of sample.

5.3. Microfluidic Chip Architecture and Methods

A molecular or cell analyzer or sorter according to the invention comprises at least one analysis unit having an inlet region in communication with a main channel, a detection region within or coincident with a portion of the main channel, and a detector associated with the detection region. Sorter embodiments also have a discrimination region or branch point in communication with the main channel and with branch channels, and a flow control responsive to the detector. The branch channels may each lead to an outlet region and to a well or reservoir. The inlet region may also communicate with a well or reservoir. As each molecule or cell passes into the detection region, it is examined for a predetermined characteristic (i.e. using the detector), and a corresponding signal is produced, for example indicating that "yes" the characteristic is present, or "no" it is not. The signal may correspond to a characteristic qualitatively or quantitatively. That is, the amount of the signal can be measured and can correspond to the degree to which a characteristic is present. For example, the strength of the signal may indicate the size of the molecule, or the potency or amount of an enzyme expressed by a cell. In response to the signal, data can be collected and/or a flow control can be activated to divert a molecule or cell into one branch channel or another. Thus, molecules or cells within the discrimination region can be sorted into an appropriate branch channel according to a signal produced by the corresponding examination at the detection region. Optical detection of molecule or cell characteristics is preferred, for example directly or by use of a reporter associated with a characteristic chosen for sorting. However, other detection techniques may also be employed.

A variety of channels for sample flow and mixing can be microfabricated on a single chip and can be positioned at any location on the chip as the detection and discrimination or sorting points, e.g., for kinetic studies (12, 14). A plurality of analysis units of the invention may be combined in one device. Microfabrication applied according to the invention eliminates the dead time occurring in conventional gel electrophoresis or flow cytometric kinetic studies, and achieves a better time-resolution. Furthermore, linear arrays of channels on a single chip, i.e., a multiplex system, can simultaneously detect and sort a sample by using an array of photomultiplier tubes (PMT) for parallel analysis of different channels (15). This arrangement can be used to improve throughput or for successive sample enrichment, and can be adapted to provide a very high throughput to the microfluidic devices that exceeds the capacity permitted by conventional flow sorters. Moreover, microfabrication permits other technologies to be integrated or combined on a single chip, such as PCR (21), moving molecules or cells using optical tweezer/trapping (16–18), transformation of cells by electroporation (19), $\mu$TAS (22), and DNA hybridization (6). Detectors and/or light filters that are used to detect molecule or cell characteristics or their reporters can also be fabricated directly on the chip.

A device of the invention can be microfabricated with a sample solution reservoir or well at the inlet region, which is typically in fluid communication with an inlet channel. A reservoir may facilitate introduction of molecules or cells into the device and into the sample inlet channel of each analysis unit. An inlet region may have an opening, such as in the floor of the microfabricated chip, to permit entry of the sample into the device. The inlet region may also contain a connector adapted to receive a suitable piece of tubing, such as liquid chromatography or HPLC tubing, through which a sample may be supplied. Such an arrangement facilitates introducing the sample solution under positive pressure in order to achieve a desired flow rate through the channels. Outlet channels and wells can be similarly provided.

Substrate and Flow Channels. A typical analysis unit of the invention comprises an inlet region that is part of and feeds or communicates with a main channel, which in turn communicates with an outlet (for analysis only) or with two (or more) branch channels at a junction or branch point, forming for example a T-shape or a Y-shape for sorting. Other shapes and channel geometries may be used as desired. The region at or surrounding the junction can also be referred to as a discrimination region, however, precise boundaries for the discrimination region are not required. A detection region is identified within or coincident with a portion of the main channel downstream of the inlet region, and at or upstream of the discrimination region or branch point. Precise boundaries for the detection region are not required, but are preferred. The discrimination region may be located immediately downstream of the detection region, or it may be separated by a suitable distance consistent with the size of the molecules, the channel dimensions, and the detection system. It will be appreciated that the channels can have any suitable shape or cross-section, such as tubular or grooved, and can be arranged in any suitable manner, so long as a flow can be directed from one channel into at least one of two or more branch channels.

The channels of the invention are microfabricated, for example by etching a silicon chip using conventional photolithography techniques, or using a micromachining technology called "soft lithography", developed in the late 1990's (11). These and other microfabrication methods may be used to provide inexpensive miniaturized devices, and in the case of soft lithography, can provide robust devices having beneficial properties such as improved flexibility, stability, and mechanical strength. When optical detection is employed, the invention also provides minimal light scatter from molecule or cell suspension and chamber material. Devices according to the invention are relatively inexpensive and easy to set up. They can also be disposable, which greatly relieves many of the concerns of gel electrophoresis (for molecules) and for sterilization and permanent adsorption of particles unto the flow chambers and channels of conventional FACS machines (for cells). Using these kinds of techniques, microfabricated fluidic devices can replace the conventional gel electrophoresis and fluidic flow chambers of the prior art.

A microfabricated device of the invention is preferably fabricated from a silicon microchip or silicon elastomer. The dimensions of the chip are those of typical microchips, ranging between about 0.5 cm to about 5 cm per side and about 1 micron to about 1 cm in thickness. The device contains at least one analysis unit containing a main channel having detection and discrimination regions. Preferably a device also contains at least one inlet region (which may contain an inlet channel) and two or more outlet regions (which have fluid communication with a branch channel in each region). It shall be appreciated that the "regions" and "channels" are in fluid communication with each other, and therefore they may overlap, i.e., there may be no clear boundary where a region or channel begins or ends. A microfabricated device can be covered with a material having transparent properties, e.g., a glass coverslip to permit detection of a reporter for example by an optical device, such as an optical microscope.

The dimensions of the channels and in particular of the detection region are influenced by the size of the molecules or cells under study. For polynucleotides, which are large by molecular standards, a typical length or diameter is about 3.4 angstroms per base pair. Thus, a DNA 49 kpbs long, such as Lambda phage DNA, is about 17 microns long when fully extended. A typical range of sizes for polynucleotides of the invention is from about 1 to about 200 kpbs, or about 0.3 to about 70 microns. Detection regions used for detecting molecules have a cross-sectional area large enough to allow a desired molecule to pass through without being substantially slowed down relative to the flow of the solution carrying it. To avoid "bottlenecks" and/or turbulence, and promote single-file flow, the channel dimensions, particularly in the detection region, should generally be at least about twice, preferably at least about five times as large per side or in diameter as the diameter of the largest molecule that will be passing through it.

For molecules such as DNA, the channels in a device are typically between about 1 to about 100 microns ($\mu$m) in diameter, with preferred channel dimensions ranging from about 2 to about 5 microns in width and between about 2 and about 4 or 5 microns in depth. Similarly, the volume of the detection region in a molecular analysis or sorting device may be from about 1 femtoliter (fl) to about 1 nanoliter (nl). Typically, the detection region will have a volume between about 10 to about 5000 fl, preferably about 40 or 50 fl to about 1000 or 2000 fl, most preferably on the order of about 200 fl.

To prevent material from adhering to the sides of the channels, the channels (and coverslip, if used) may have a coating which minimizes adhesion. Such a coating may be intrinsic to the material from which the device is manufactured, or it may be applied after the structural aspects of the channels have been microfabricated. "TEFLON" is an example of a coating that has suitable surface properties.

A silicon substrate containing the microfabricated flow channels and other components is preferably covered and sealed, most preferably with a transparent cover, e.g., thin glass or quartz, although other clear or opaque cover materials may be used. When external radiation sources or detectors are employed, the detection region is covered with a clear cover material to allow optical access to the molecules or cells. For example, anodic bonding to a "PYREX" cover slip can be accomplished by washing both components in an aqueous $H_2SO_4/H_2O_2$ bath, rinsing in water, and then, for example, heating to about 350 degrees C. while applying a voltage of 450V.

Switching and Flow Control. Electro-osmotic and pressure-driven flow are examples of methods or systems for flow control, that is, manipulating the flow of molecules cells, particles or reagents in one or more directions and/or into one or more channels of a microfluidic device of the invention (8, 12, 13, 23). Other methods may also be used, for example, electrophoresis and dielectrophoresis. In certain embodiments of the invention, the flow moves in one "forward" direction, e.g. from the inlet region through the main and branch channels to an outlet region. In other embodiments the direction of flow is reversible. Application of these techniques according to the invention provides more rapid and accurate devices and methods for sorting, for example, because the sorting occurs at or in a discrimination region that can be placed at or immediately after a detection region. This provides a shorter distance for molecules or cells to travel, they can move more rapidly and with less turbulence, and can more readily be moved, examined, and sorted in single file, i. e., one at a time. In a reversible embodiment, potential sorting errors can be avoided, for example by reversing and slowing the flow to re-read or resort a molecule or cell (or a plurality thereof) before irretrievably committing the molecule or cell to the outlet or to a particular branch channel.

Without being bound by any theory, electro-osmosis is believed to produce motion in a stream containing ions, e.g. a liquid such as a buffer, by application of a voltage differential or charge gradient between two or more electrodes. Neutral (uncharged) molecules or cells can be carried by the stream. Electro-osmosis is particularly suitable for rapidly changing the course, direction or speed of flow. Electrophoresis is believed to produce movement of charged objects in a fluid toward one or more electrodes of opposite charge, and away from one on or more electrodes of like charge. Because of its charged nature (2 charges for each base pair) DNA can be conveniently moved by electrophoresis in a buffer of appropriate pH.

Dielectrophoresis is believed to produce movement of dielectric objects, which have no net charge, but have regions that are positively or negatively charged in relation to each other. Alternating, non-homogeneous electric fields in the presence of particles, such as molecules, cells or beads, cause them to become electrically polarized and thus to experience dielectrophoretic forces. Depending on the dielectric polarizability of the particles and the suspending medium, dielectric particles will move either toward the regions of high field strength or low field strength. For example, the polarizability of living cells depends on their composition, morphology, and phenotype and is highly dependent on the frequency of the applied electrical field. Thus, cells of different types and in different physiological states generally possess distinctly different dielectric properties, which may provide a basis for cell separation, e.g., by differential dielectrophoretic forces. According to formulas provided in Fiedler et al. (13), individual manipulation of single particles requires field differences (inhomogeneties) with dimensions close to the particles.

Manipulation is also dependent on permittivity (a dielectric property) of the particles with the suspending medium. Thus, polymer particles and living cells show negative dielectrophoresis at high-field frequencies in water. For example, dielectrophoretic forces experienced by a latex sphere in a 0.5 MV/m field (10V for a 20 micron electrode gap) in water are predicted to be about 0.2 piconewtons (pN) for a 3.4 micron latex sphere to 15 pN for a 15 micron latex sphere (13). These values are mostly greater than the hydrodynamic forces experienced by the sphere in a stream (about 0.3 pN for a 3.4 micron sphere and 1.5 pN for a 15 micron sphere). Therefore, manipulation of individual cells or particles can be accomplished in a streaming fluid, such as in a cell sorter device, using dielectrophoresis. Using conventional semiconductor technologies, electrodes can be microfabricated onto a substrate to control the force fields in a microfabricated sorting device of the invention. Dielectrophoresis is particularly suitable for moving objects that are electrical conductors. The use of AC current is preferred, to prevent permanent alignment of ions. Megahertz frequencies are suitable to provide a net alignment, attractive force, and motion over relatively long distances. E.g. Benecke (49).

Optical tweezers can also be used in the invention to trap and move objects, e.g. molecules or cells, with focused beams of light such as lasers. Flow can also be obtained and controlled by providing a pressure differential or gradient between one or more channels of a device or in a method of the invention.

Molecules or cells can be moved by direct mechanical switching, e.g. with on-off valves, or by squeezing the channels. Pressure control may also be used, for example by raising or lowering an output well to change the pressure inside the channels on the chip. See e.g. the devices and methods described in pending U.S. application Ser. No. 08/932,774 filed Sep. 25, 1997; No. 60/108,894 filed Nov. 17, 1998; No. 60/086,394 filed May 22, 1998; and No. 09/325,667 filed May 21, 1999 (molecular analysis systems). These methods and devices can further be used in combination with the methods and devices described in pending U.S. application Ser. No. 60/141,503 (filed Jun. 28, 1999), No. 609/147,199 (filed Aug. 3, 1999) and No. 60/186, 856 (filed Mar. 3, 2000). Each of these references is hereby incorporated by reference in its entirety.

Detection and Discrimination for Sorting. The detector can be any device or method for interrogating a molecule or cell as it passes through the detection region. Typically, molecules or cells are to be analyzed or sorted according to a predetermined characteristic that is directly or indirectly detectable, and the detector is selected or adapted to detect that characteristic. A preferred detector is an optical detector, such as a microscope, which may be coupled with a computer and/or other image processing or enhancement devices to process images or information produced by the microscope using known techniques. For example, molecules can be sorted by size or molecular weight. Cells can be sorted for whether they contain or produce a particular protein, by using an optical detector to examine each cell for an optical indication of the presence or amount of that protein. The protein may itself be detectable, for example by a characteristic fluorescence, or it may be labeled or associated with a reporter that produces a detectable signal when the desired protein is present, or is present in at least a threshold amount. There is no limit to the kind or number of molecule or cell characteristics that can be identified or measured using the techniques of the invention, which include without limitation surface characteristics of the cell and intracellular characteristics, provided only that the characteristic or characteristics of interest for sorting can be sufficiently identified and detected or measured to distinguish cells having the desired characteristic(s) from those which do not. For example, any label or reporter as described herein can be used as the basis for sorting molecules or cells, i. e. detecting them to be collected.

In preferred embodiments, the molecules or cells are analyzed and/or separated based on the intensity of a signal from an optically-detectable reporter bound to or associated with them as they pass through a detection window or "detection region" in the device. Molecules or cells having an amount or level of the reporter at a selected threshold or within a selected range are diverted into a predetermined outlet or branch channel of the device. The reporter signal is collected by a microscope and measured by a photomultiplier tube (PMT). A computer digitizes the PMT signal and controls the flow via valve action or electro-osmotic potentials. Alternatively, the signal can be recorded or quantified, as a measure of the reporter and/or its corresponding characteristic or marker, e.g. for purposes of evaluation without necessarily proceeding to sort the molecules or cells.

In one embodiment, the chip is mounted on an inverted optical microscope. Fluorescence produced by a reporter is excited using a laser beam focused on molecules (e.g. DNA) or cells passing through a detection region. Fluorescent reporters include, e.g., rhodamine, fluorescein, Texas red, Cy3, Cy5, phycobiliprotein, green fluorescent protein (GFP), YOY-1, and picogreen. In molecular fingerprinting applications, the reporter labels are preferably a fluorescently-labeled single nucleotides, such as fluorescein-dNTP, rhodamine-dNTP, Cy3-dNTP, Cy5-dNTP, where dNTP represents dATP, dTTP, dUTP or dCTP. The reporter can also be chemically-modified single nucleotides, such as biotin-dNTP. Thus, in one aspect of the invention, the device can determine the size or molecular weight of molecules such as polynucleotide fragments passing through the detection region, or the presence or degree of some other characteristic indicated by a reporter. If desired, the molecules can be sorted based on this analysis.

To detect a reporter or determine whether a molecule has a desired characteristic, the detection region may include an apparatus for stimulating a reporter for that characteristic to emit measurable light energy, e.g., a light source such as a laser, laser diode, high-intensity lamp, (e.g., mercury lamp), and the like. In embodiments where a lamp is used, the channels are preferably shielded from light in all regions except the detection region. In embodiments where a laser is used, the laser can be set to scan across a set of detection regions from different analysis units. In addition, laser diodes may be microfabricated into the same chip that contains the analysis units. Alternatively, laser diodes may be incorporated into a second chip (i. e., a laser diode chip) that is placed adjacent to the microfabricated sorter chip such that the laser light from the diodes shines on the detection region(s).

In preferred embodiments, an integrated semiconductor laser and/or an integrated photodiode detector are included on the silicon wafer in the vicinity of the detection region. This design provides the advantages of compactness and a shorter optical path for exciting and/or emitted radiation, thus minimizing distortion.

Sorting Schemes. According to the invention, molecules or cells are sorted dynamically in a flow stream of microscopic dimensions, based on the detection or measurement of a characteristic, marker or reporter that is associated with the molecules or cells. The stream is typically but not necessarily continuous, and may be stopped and started, reversed, or changed in speed. Prior to sorting, a liquid that does not contain sample molecules or cells can be introduced at an inlet region of the chip (e.g., from an inlet well or channel) and is directed through the device by capillary action, to hydrate and prepare the device for sorting. If desired, the pressure can be adjusted or equalized for example by adding buffer to an outlet region. The liquid typically is an aqueous buffer solution, such as ultrapure water (e.g., 18 mega ohm resistivity, obtained for example by column chromatography), ultrapure water, 10 mM Tris HCL and 1 mM EDTA (TE), phosphate buffer saline (PBS), and acetate buffer. Any liquid or buffer that is physiologically compatible with the population of molecules or cells to be sorted can be used.

A sample solution containing a mixture or population of molecules or cells in a suitable carrier fluid (such as a liquid or buffer described above) is supplied to the inlet region. The capillary force causes the sample to enter the device. The force and direction of flow can be controlled by any desired method for controlling flow, for example, by a pressure differential, by valve action, or by electro-osmotic flow, e.g., produced by electrodes at inlet and outlet channels. This permits the movement of the molecules or cells into one or more desired branch channels or outlet regions.

A "forward" sorting algorithm, according to the invention, includes embodiments where molecules or cells from an inlet channel flow through the device to a predetermined branch or outlet channel (which can be called a "waste channel"), until the level of measurable reporter is above a pre-set threshold. At that time, the flow is diverted to deliver the molecule or cell to another channel. For example, in an electro-osmotic embodiment, where switching is virtually instantaneous and throughput is limited by the highest voltage, the voltages are temporarily changed to divert the chosen molecule or cell to another predetermined outlet channel (which can be called a "collection channel"). Sorting, including synchronizing detection of a reporter and diversion of the flow, can be controlled by various methods including computer or microprocessor control. Different algorithms for sorting in the microfluidic device can be implemented by different computer programs, such as programs used in conventional FACS devices for sorting cells. For example, a programmable card can be used to control switching, such as a Lab PC 1200 Card, available from National Instruments, Austin, Tex. Algorithms as sorting procedures can be programmed using C++, LABVIEW, or any suitable software. The method is advantageous, for example, because conventional gel electrophoresis methods are generally not automated or under computer control.

A "reversible" sorting algorithm can be used in place of a "forward" mode, for example in embodiments where switching speed may be limited. For example, a pressure-switched scheme can be used instead of electro-osmotic flow and does not require high voltages and may be more robust for longer runs. However, mechanical constraints may cause the fluid switching speed to become rate-limiting. In a pressure-switched scheme the flow is stopped when a molecule or cell of interest is detected. By the time the flow stops, the molecule or cell may be past the branch point and be part-way down the waste channel. In this situation, a reversible embodiment can be used. The system can be run backwards at a slower (switchable) speed (e.g., from waste to inlet), and the molecule or cell is then switched to a different channel. At that point, a potentially mis-sorted molecule or cell is "saved", and the device can again be run at high speed in the forward direction. This "reversible" sorting method is not possible with standard FACS machines or in gel electrophoresis technologies. FACS machines mostly sort aerosol droplets which cannot be reversed back to the chamber, in order to be redirected. The aerosol droplet sorter are virtually irreversible. In gel electrophoresis, molecules such as polynucleotides are drawn through a gel by an electric current and migrate at different rates proportional to their molecular weights. Individual molecules can not be reversed through the gel, and indeed, altering the rate or direction of migration would prevent meaningful use of the technique. Reversible sorting is particularly useful for identifying rare molecules or cells (e.g., in molecular evolution and cancer cytological identification), or molecules or cells that are few in number, which may be misdirected due to a margin of error inherent to any fluidic device. The reversible nature of the device of the invention permits a reduction in this possible error.

A "reversible" sorting method permits multiple time course measurements of a single molecule or cell. This allows for observations or measurements of the same molecule or cell at different times, because the flow reverses the molecule or cell back into the detection window before directing it to a downstream channel. Measurements can be compared or confirmed, and changes in molecule or cell properties over time can be examined, for example in kinetic studies.

When trying to separate molecules or cells in a sample at a very low ratio to the total number of molecules or cells, a sorting algorithm can be implemented that is not limited by the intrinsic switching speed of the device. Consequently, the molecules or cells flow at the highest possible static (non-switching) speed from the inlet channel to the waste channel. Unwanted molecules or cells can be directed into the waste channel at the highest speed possible, and when a desired molecule or cell is detected, the flow can be slowed down and then reversed, to direct it back into the detection region, from where it can be redirected (i.e. to accomplish efficient switching). Hence the molecules or cells can flow at the highest possible static speed.

Figure 11A:
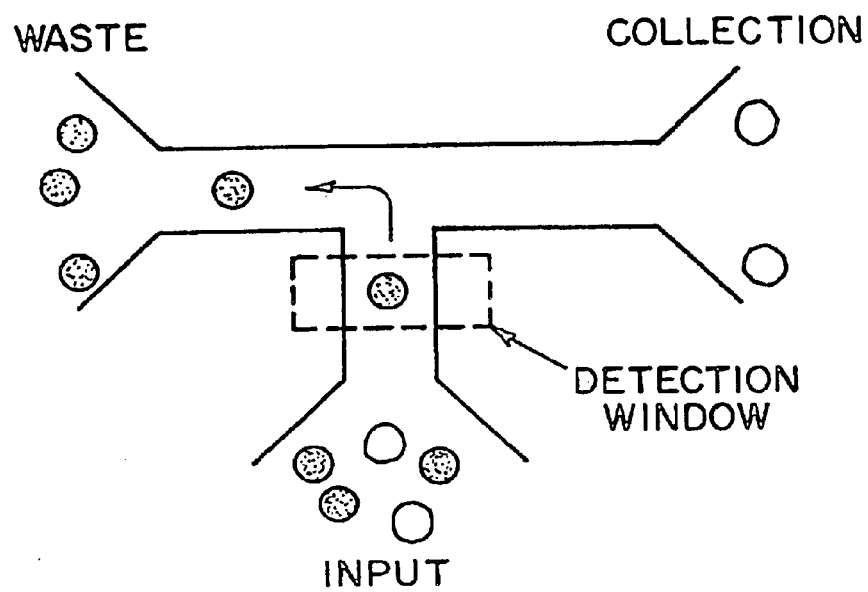
FIGS. 11A and 11B show a sorting scheme according to the invention, in diagrammatic form.
Figure 11B:
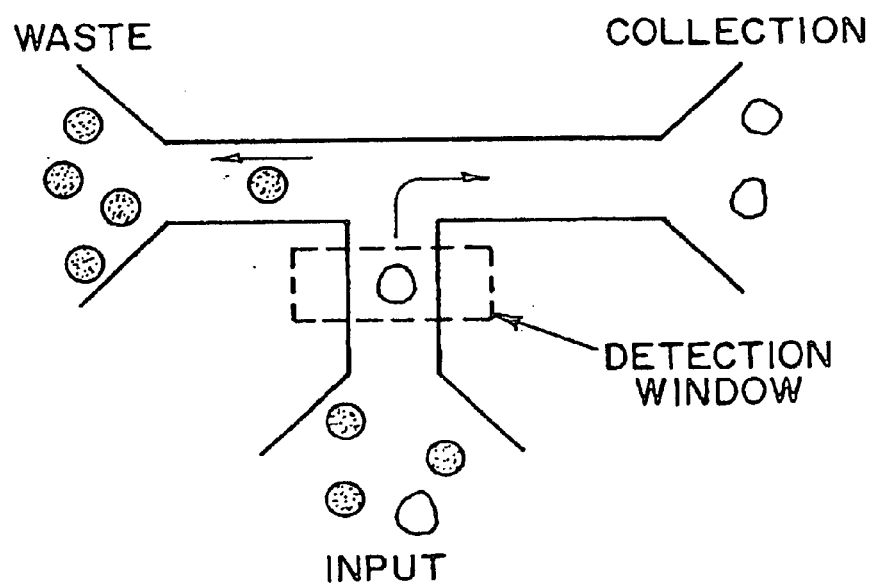
Figure 12A:
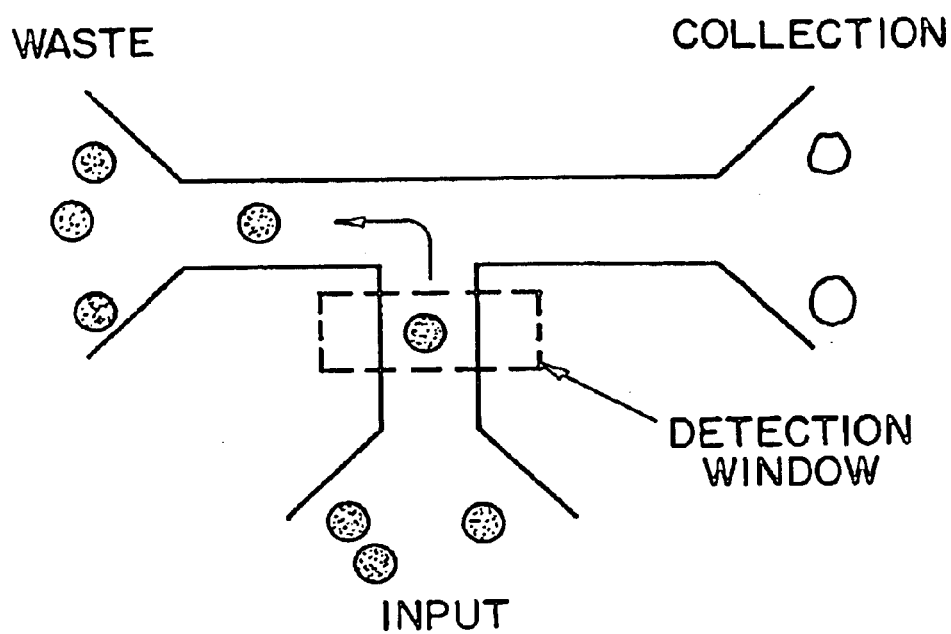
FIGS. 12A and 12B show a reversible sorting scheme according to the invention.
Figure 12B:
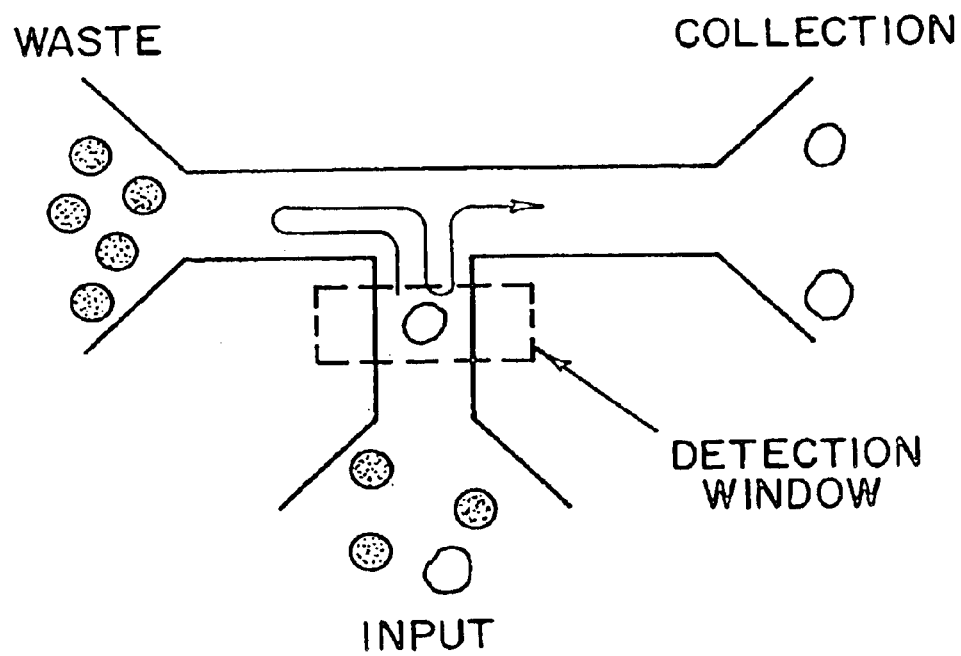

Preferably, the fluid carrying the molecules or cells has a relatively low Reynolds Number, for example $10^{-2}$. The Reynolds Number represents an inverse relationship between the density and velocity of a fluid and its viscosity in a channel of given length. More viscous, less dense, slower moving fluids over a shorter distance will have a lower Reynolds Number, and are easier to divert, stop, start, or reverse without turbulence. Because of the small sizes and slow velocities, microfabricated fluid systems are often in a low Reynolds number regime (<<1). In this regime, inertial effects, which cause turbulence and secondary flows, are negligible; viscous effects dominate the dynamics. These conditions are advantageous for sorting, and are provided by microfabricated devices of the invention. Accordingly the microfabricated devices of the invention are preferably if not exclusively operated at a low or very low Reynold's number. Exemplary sorting schemes are shown diagrammatically in FIGS. 11A and B and FIGS. 12A and B.

6. EXAMPLES

The present invention is also described by means of particular examples. However, the use of such examples anywhere in the specification is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification and can be made without departing from its spirit and scope. The invention is therefore to be limited only by the terms of the appended claims along with the full scope of equivalents to which the claims are entitled.

6.1. A Microfabricated Polynucleotide Sorting Device

FIG. 1 shows an embodiment of a microfabricated polynucleotide sorting device 20 in accordance with the invention. The device is preferably fabricated from a silicon microchip 22. The dimensions of the chip are those of typical microchips, ranging between about 0.5 cm to about 5 cm per side and about 0.1 mm to about 1 cm in thickness. The device contains a solution inlet 24, two or more solution outlets, such as outlets 26 and 28, and at least one analysis unit, such as the unit at 30.

Each analysis unit includes a main channel 32 having at one end a sample inlet 34, and downstream of the sample inlet, a detection region 36, and downstream of the detection region 36 a discrimination region 38. A plurality of branch channels, such as channels 40 and 42, are in fluid communication with and branch out from the discrimination region. The dimensions of the main and branch channels are typically between about 1 µm and 10 µm per side, but may vary at various points to facilitate analysis, sorting and/or collection of molecules.

In embodiments such as shown in FIG. 1, where the device contains a plurality of analysis units, the device may further contain collection manifolds, such as manifolds 44 and 46, to facilitate collection of sample from corresponding branch channels of different analysis units for routing to the appropriate solution outlet. The manifolds are preferably microfabricated into different levels of the device, as indicated by the dotted line representing manifold 46. Similarly, such embodiments may include a sample solution reservoir, such as reservoir 48, to facilitate introduction of sample into the sample inlet of each analysis unit.

Also included with the device is a processor, such as processor 50. The processor can be integrated into the same chip as contains the analysis unit(s), or it can be separate, e.g, an independent microchip connected to the analysis unit-containing chip via electronic leads, such as leads 52 (connected to the detection region(s) and 54 (connected to the discrimination region(s)).

Figure 2:
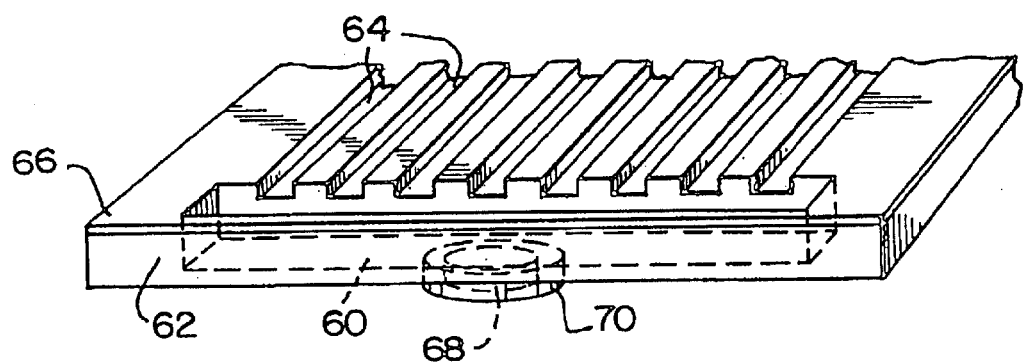
FIG. 2 shows a partial perspective view of a nucleic acid sorting device, showing a sample solution reservoir and sample inlet.

As mentioned above, the device may be microfabricated with a sample solution reservoir to facilitate introduction of a polynucleotide solution into the device and into the sample inlet of each analysis unit. With reference to FIG. 2, the reservoir is microfabricated into the silicon substrate of the chip 62, and is covered, along with the channels (such as main channel 64) of the analysis units, with a glass coverslip 66. The device solution inlet comprises an opening 68 in the floor of the microchip. The inlet may further contain a connector 70 adapted to receive a suitable piece of tubing, such as liquid chromatography or HPLC tubing, through which the sample may be supplied. Such an arrangement facilitates introducing the sample solution under positive pressure, to achieve a desired flow rate through the channels as described below.

Downstream of the sample inlet of the main channel of each analysis unit is the detection region, designed to detect the level of an optically-detectable reporter associated with polynucleotides present in the region. Exemplary embodiments of detection regions in devices of the invention are shown in FIGS. 3A and 3B.

6.2. Photodiode Detectors

Figure 3A:
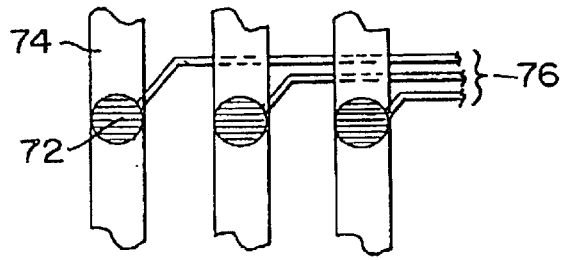
FIG. 3A shows one embodiment of a detection region used in a nucleic acid sorting device, having an integrated photodiode detector.
Figure 3B:
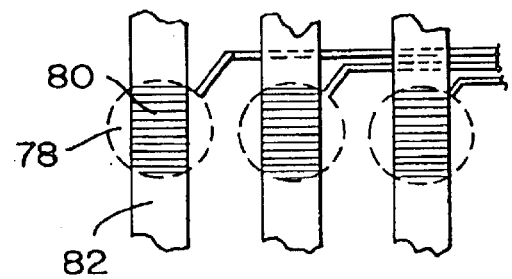
FIG. 3B shows another embodiment of a detection region, having an integrated photodiode detector, and providing a larger detection volume (than the embodiment of FIG. 3A).

With reference to FIG. 3A, each detection region is formed of a portion of the main channel of an analysis unit and a photodiode, such as photodiode 72, located in the floor of the main channel. In this embodiment, the area detectable by the detection region is the circular portion each channel defined by the receptive field of the photodiode in that channel. The volume of the detection region is the volume of a cylinder with a diameter equal to the receptive field of the photodiode and a height equal to the depth of the channel above the photodiode.

The signals from the photodiodes are carried via output lines 76 to the processor (not shown), which processes the signals into values corresponding to the length of the polynucleotide giving rise to the signal. The processor then uses this information, for example, to control active elements in the discrimination region. The processor may process the signals into values for comparison with a predetermined or reference set of values for analysis or sorting.

When more than one detection region is used, the photodiodes in the laser diode chip are preferably spaced apart relative to the spacing of the detection regions in the analysis unit. That is, for more accurate detection, the photodiodes are placed apart at the same spacing as the spacing of the detection region.

The processor can be integrated into the same chip that contains the analysis unit(s), or it can be separate, e.g., an independent microchip connected to the analysis unit-containing chip via electronic leads that connect to the detection region(s) and/or to the discrimination region(s), such as by a photodiode. The processor can be a computer or microprocessor, and is typically connected to a data storage unit, such as computer memory, hard disk, or the like, and/or a data output unit, such as a display monitor, printer and/or plotter.

The types and numbers of molecules or cells, based on detection of a reporter associated with or bound to the molecules or cells passing through the detection region, can be calculated or determined, and the data obtained can be stored in the data storage unit. This information can then be further processed or routed to the data outlet unit for presentation, e.g. histograms, of the types of molecules or cells (or levels of a cell protein, saccharide), or some other characteristic. The data can also be presented in real time as the sample is flowing through the device.

With reference to FIG. 3B, the photodiode 78 can be larger in diameter than the width of the main channel, forming a detection region 80 that is longer (along the length of the main channel 82) than it is wide. The volume of such a detection region is approximately equal to the cross-sectional area of the channel above the diode multiplied by the diameter of the diode.

In a preferred sorting embodiment the detection region is connected by the main channel to the discrimination region. The discrimination region may be located immediately downstream of the detection region, or may be separated by a suitable length of channel. Constraints on the length of channel between the detection and discrimination regions are discussed below, with respect to the operation of the device. This length is typically between about 1 µm and about 2 cm. The discrimination region is at the junction of the main channel and the branch channels. It comprises the physical location where molecules are directed into a selected branch channel. The means by which the molecules or cells are directed into a selected branch channel may (i) be present in the discrimination region, as in, e.g., electrophoretic or microvalve-based discrimination, or (ii) be present at a distant location, as in, e.g., electroosmotic or flow stoppage-based discrimination.

If desired, the device may contain a plurality of analysis units, i.e., more than one detection and discrimination region, and a plurality of branch channels which are in fluid communication with and branch out from the discrimination regions. It will be appreciated that the position and fate of molecules or cells in the discrimination region can be monitored by additional detection regions installed, for example, immediately upstream of the discrimination region and/or within the branch channels immediately downstream of the branch point. The information obtained by the additional detection regions can be used by a processor to continuously revise estimates of the velocity of the molecules or cells in the channels and to confirm that molecules or cells having a selected characteristic enter the desired branch channel.

A group of manifolds (a region consisting of several channels which lead to or from a common channel) can be included to facilitate movement of sample from the different analysis units, through the plurality of branch channels and to the appropriate solution outlet. Manifolds are preferably microfabricated into the chip at different levels of depth. Thus, devices of the invention having a plurality of analysis units can collect the solution from associated branch channels of each unit into a manifold, which routes the flow of solution to an outlet. The outlet can be adapted for receiving, for example, a segment of tubing or a sample tube, such as a standard 1.5 ml centrifuge tube. Collection can also be done using micropipettes.

6.3. Valve Structures

Figure 4A:
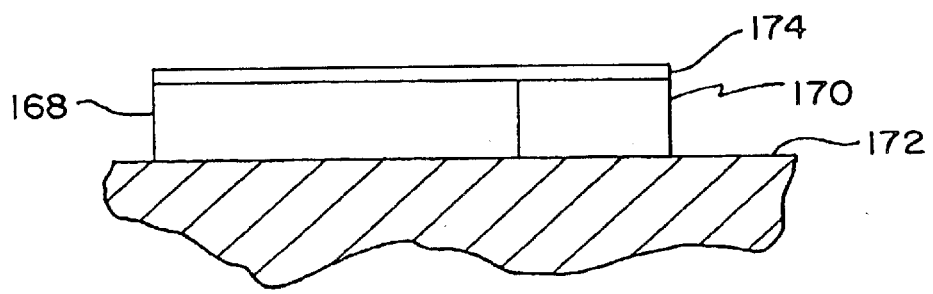
FIGS. 4A–4B show one embodiment of a valve within a branch channel of a nucleic acid sorting device, and steps in fabrication of the valve.
Figure 4B:
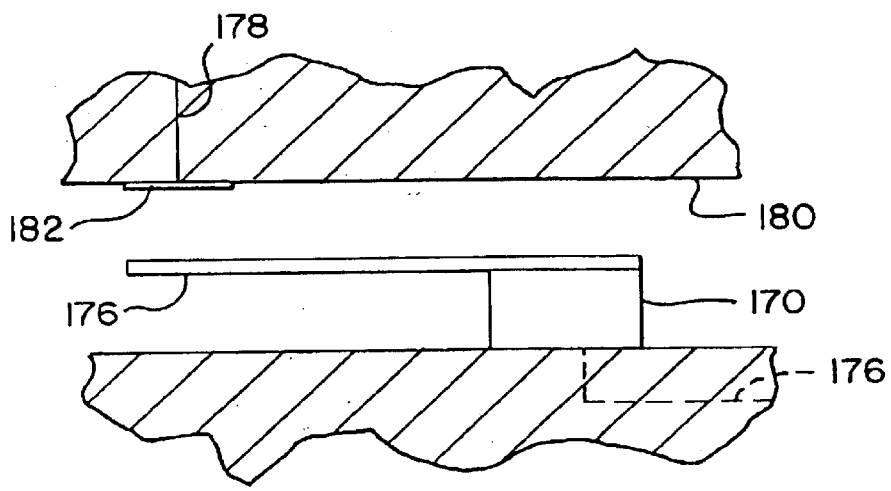

In an embodiment where pressurized flow is used, valves can be used to block or unblock the pressurized flow of molecules or cells through selected channels. A thin cantilever, for example, may be included within a branch point, as shown in FIGS. 4A and 4B, such that it may be displaced towards one or the other wall of the main channel, typically by electrostatic attraction, thus closing off a selected branch channel. Electrodes are on the walls of the channel adjacent to the end of the cantilever. Suitable electrical contacts for applying a potential to the cantilever are also provided in a similar manner as the electrodes. Because the cantilever in FIG. 4B is parallel to the direction of etching, it may be formed of a thin layer of silicon by incorporating the element into the original photoresist pattern. The cantilever is preferably coated with a dielectric material such as silicon nitride, as described in Wise, et al., 1995 (35), for example, to prevent short circuiting between the conductive surfaces.

Alternatively, a valve may be situated within each branch channel, rather than at the branch point, to close off and terminate pressurized flow through selected channels. Because the valves are located downstream of the discrimination region, the channels in this region may be formed having a greater width than in the discrimination region, which simplifies the formation of valves.

A valve within a channel may be microfabricated, if desired, in the form of an electrostatically operated cantilever or diaphragm. Techniques for forming such elements are well known in the art (e.g., 24, 29, 35, 36, 37). Typical processes include the use of selectively etched sacrificial layers in a multilayer structure or, for example, the undercutting of a layer of silicon dioxide via anisotropic etching. For example, to form a cantilever within a channel, as illustrated in FIGS. 4A and 4B, a sacrificial layer 168 may be formed adjacent to a small section of a non-etchable material 170, using known photolithography methods, on the floor of a channel, as shown in FIG. 4A. Both layers can then be coated with, for example, silicon dioxide or another non-etchable layer, as shown at 172. Etching of the sacrificial layer deposits the cantilever member 174 within the channel, as shown in FIG. 4B. Suitable materials for the sacrificial layer, non-etchable layers and etchant include undoped silicon, p-doped silicon and silicon dioxide, and the etchant EDP (ethylene diamine/pyrocatechol), respectively. Because the cantilever in FIG. 4B is parallel to the direction of etching, it may be formed of a thin layer of silicon by incorporating the element into the original photoresist pattern. The cantilever is preferably coated with a dielectric material such as silicon nitride, as described in (35) for example, to prevent short circuiting between the conductive surfaces.

The width of the cantilever or diaphragm should approximately equal that of the channel, allowing for movement within the channel. If desired, the element may be coated with a more malleable material, such as a metal, to allow for a better seal. Such coating may also be employed to render a non-conductive material, such as silicon dioxide, conductive.

As above, suitable electrical contacts are provided for displacing the cantilever or diaphragm towards the opposing surface of the channel. When the upper surface is a glass cover plate, as described below, electrodes and contacts may be deposited onto the glass.

It will be apparent to one of skill in the field that other types of valves or switches can be designed and fabricated, using well known photolithographic or other microfabrication techniques, for controlling flow within the channels of the device. Multiple layers of channels can also be prepared.

Operation of the valves or charging of the electrodes, in response to the level of fluorescence measured from an analyte molecule, is controlled by the processor, which receives this information from the detector. All of these components are operably connected in the apparatus, and electrical contacts are included as necessary, using standard microchip circuitry.

In preferred embodiments, an integrated semiconductor laser and/or an integrated photodiode detector are included on the silicon wafer in the vicinity of the detection region. This design provides the advantages of compactness and a shorter optical path for exciting and/or emitted radiation, thus minimizing distortion.

The silicon substrate containing the microfabricated flow channels and other components is covered and sealed, preferably with a thin glass or quartz cover, although other clear or opaque cover materials may be used. when external radiation sources or detectors are employed, the interrogation region is covered with a clear cover material to allow optical access to the analyte molecules. Anodic bonding to a "PYREX" cover slip may be accomplished by washing both components in an aqueous $H_2SO_4/H_2O_2$ bath, rinsing in water, and then heating to about 350° C. while applying a voltage of, e.g., 450V.

6.4. Exemplary Microchip Architectures for Sorting

As illustrated with respect to FIGS. 5A–5D, there are a number of ways in which cells can be routed or sorted into a selected branch channel.

Figure 5A:
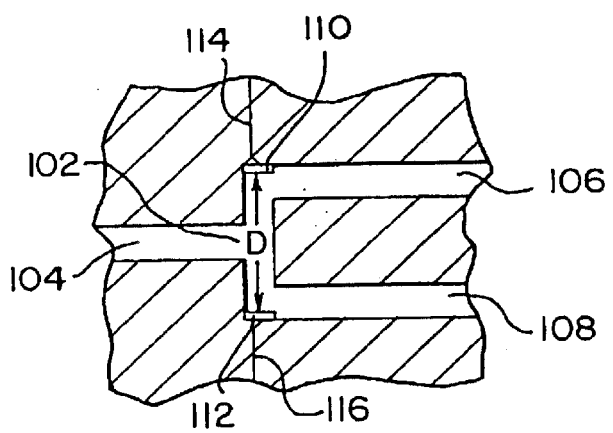
FIG. 5A shows one embodiment of a discrimination region used in a nucleic acid sorting device, having electrodes disposed within the channels for electrophoretic discrimination.

FIG. 5A shows a discrimination region 102, which is suitable for electrophoretic discrimination as the sorting technique. The discrimination region is preceded by a main channel 104. A junction divides the main channel into two branch channels 106 and 108. The discrimination region 102 includes electrodes 110 and 112, positioned on outer side walls of the branch channels 106 and 108, and which connect to leads 114 and 116. The leads are connected to a voltage source (not shown) incorporated into or controlled by a processor (not shown), as described, infra. The distance (D) between the electrodes is preferably less than the average distance separating the cells during flow through the main channel. The dimensions of the electrodes are typically the same as the dimensions of the channels in which they are positioned, e.e such that the electrodes are as high and wide as the channel.

Figure 5B:
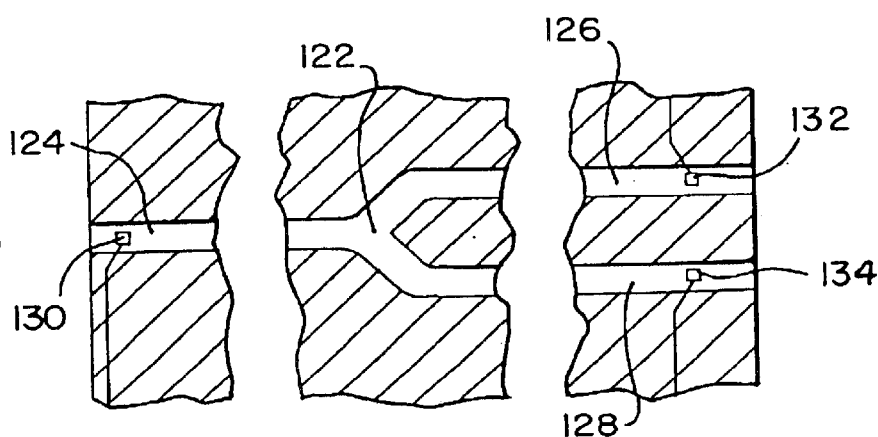
FIG. 5B shows another embodiment of a discrimination region used in a nucleic acid sorting device, having electrodes disposed for electroosmotic discrimination.

The discrimination region shown in FIG. 5B is suitable for use in a device that employs electro-osmotic flow, to move the molecules or cells and bulk solution through the device. FIG. 4B shows a discrimination region 122 which is preceded by a main channel 124. The main channel contains a junction that divides the main channel into two branch channels 126 and 128. An electrode 130 is placed downstream of the junction of the main channel, for example near the sample inlet of main channel. Electrodes are also placed in each branch channel (electrodes 132 and 134). The electrode 130 can be negative and electrodes 132 and 134 can be positive (or vice versa) to establish bulk solution flow according to well-established principles of electro-osmotic flow (25). See, also, U.S. patent application Ser. No. 09/325, 667 filed May 21, 1999.

After a molecule or cell passes the detection region (not shown) and enters the discrimination region 122 (e.g. between the main channel and the two branch channels) the voltage to one of the electrodes 132 or 134 can be shut off, leaving a single attractive force that acts on the solution and the molecule or cell to influence it into the selected branch channel. As above, the appropriate electrodes are activated after the molecule or cell has committed to the selected branch channel in order to continue bulk flow through both channels. In one embodiment, the electrodes are charged to divert the flow into one branch channel, for example channel 126, which can be called a waste channel. In response to a signal indicating that a molecule or cell has been identified or selected for collection, the charge on the electrodes can be changed to divert the selected molecule or cell into the other channel (channel 128), which can be called a collection channel.

Figure 5C:
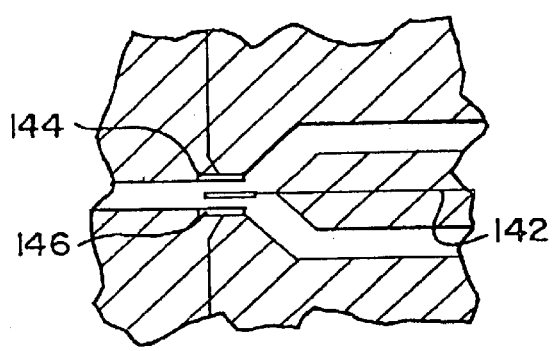
FIGS. 5C and 5D show two further embodiments of a discrimination region, having valves disposed for pressure electrophoretic separation, where the valves are within the branch point, as shown in FIG. 5C, or within the branch channels, as shown in FIG. 5D.

In another embodiment of the invention, shown in FIG. 5C, the molecules or cells are directed into a predetermined branch channel via a valve 140 in the discrimination region. The valve 140 comprises a thin extension of material to which a charge can be applied via an electrode lead 142. The valve 140 is shown with both channels open, and can be deflected to close either branch channel by application of a voltage across electrodes 144 and 146. A molecule or cell is detected and chosen for sorting in the detection region (not shown), and can be directed to the appropriate channel by closing off the other channel, e.g by applying, removing or changing a voltage applied to the electrodes. The valve can also be configured to close one channel in the presence of a voltage, and to close the other channel in the absence of a voltage.

Figure 5D:
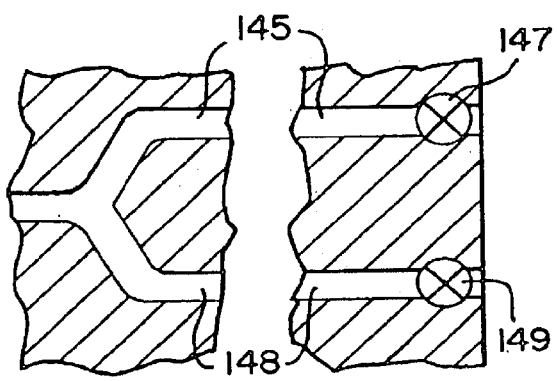

FIG. 5D shows another embodiment of a discrimination region of the invention, which uses flow stoppage in one or more branch channels as the discrimination means. The sample solution moves through the device by application of positive pressure at an end where the solution inlet is located. Discrimination or routing of the molecules or cells is affected by simply blocking a branch channel (145 or 148) or a branch channel sample outlet using valves in a pressure-driven flow (147 or 149). Due to the small size scale of the channels and the incompressibility of liquids, blocking the solution flow creates an effective "plug" in the non-selected branch channel, thereby temporarily routing the molecule or cell together with the bulk solution flow into the selected channel. Valve structures can be incorporated downstream from the discrimination region, which are controlled by the detection region, as described herein.

Alternatively, the discrimination function represented in FIG. 5D may be controlled by changing the hydrostatic pressure at the sample outlets of one or both branch channels 145 or 148. If the branch channels in a particular analysis unit have the same resistance to fluid flow, and the pressure at the sample inlet of the main channel of an analysis unit is P, then the fluid flow out of any selected branch channel can be stopped by applying a pressure $P/n$ at the sample outlet of the desired branch channel, where n is the number of branch channels in the analysis unit. Accordingly, in an analysis unit having two branch channels, the pressure applied at the outlet of the branch to be blocked is $P/2$.

As shown in FIG. 5D, a valve is situated within each branch channel, rather than at the branch point, to close off and terminate pressurized flow through selected channels. Because the valves are located at a point downstream from the discrimination region, the channels in this region may be formed having a greater width than in the discrimination region in order to simplify the formation of valves. The width of the cantilever or diaphragm should approximately equal the width of the channel, allowing for movement within the channel. If desired, the element may be coated with a more malleable material, such as a metal, to allow for a better seal. Such coating may also be employed to render a non-conductive material, such as silicon dioxide, conductive. As above, suitable electrical contacts are provided for displacing the cantilever or diaphragm towards the opposing surface of the channel. When the upper surface is a glass cover plate, electrodes and contacts may be deposited onto the glass.

6.5. A Cascade Device

Figure 6:
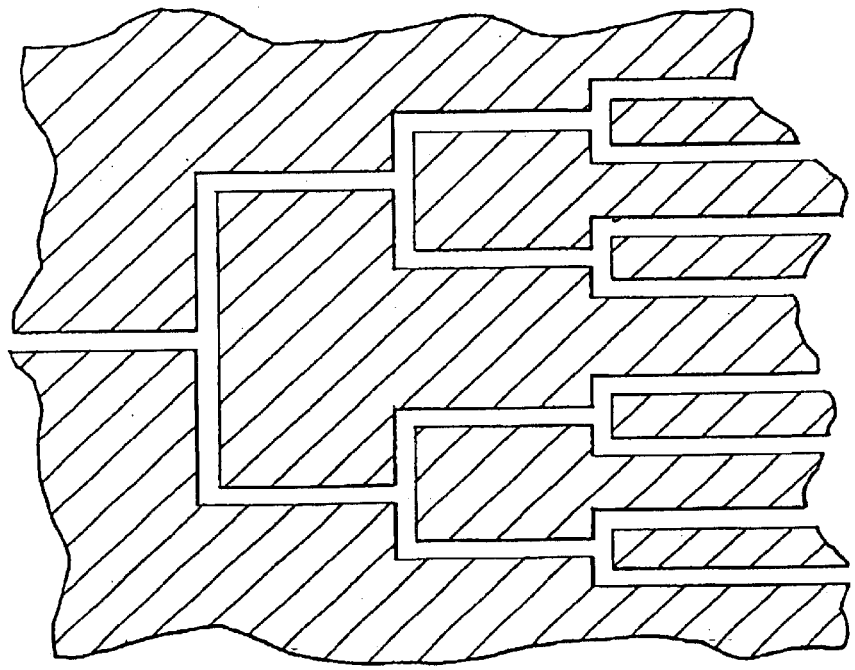
FIG. 6 shows a device with analysis units containing a cascade of detection and discrimination regions suitable for successive rounds of polynucleotide or cell sorting.

FIG. 6 shows a device with analysis units containing a cascade of detection and discrimination regions suitable for successive rounds of polynucleotide or cell sorting. Such a configuration may be used, for example, with a polynucleotide or cellsorting device to generate a series of samples containing "fractions" of polynucleotides, where each fraction contains a specific size range of polynucleotide fragments (e.g., the first fraction contains 100–500 bp fragments, the next 500–1000 bp fragments, and so on). In a cell sorting device, such a cascade configuration may be used to sequentially assay the cell for, e.g., three different fluorescent dyes corresponding to expression of three different molecular markers. Samples collected at the outlets of the different branch channels contain pools of cells expressing defined levels of each of the three markers. The number of reporters employed, and therefore the number of markers of interest, can be varied as desired, e.g. to meet the needs of a particular experiment or application.

6.6. Microfabricated Polynucleotide Analysis Device

Also included in the present invention is a microfabricated polynucleotide analysis device suitable for quantitation and analysis of the size distribution of polynucleotide fragments in solution. Such a device is a simplified version of the sorting device described above, in that analysis units in the device need not contain a discrimination region or branch channels, and the device need not contain a means for directing molecules to selected branch channels. Each analysis unit comprises a single main channel containing a detection region as described above. Since the optics which collect the optical signal (e.g., fluorescence) can be situated immediately adjacent the flow stream (e.g., diode embedded in the channel of a microscope objective adjacent a glass coverslip covering the channel), the signal-to-noise ratio of the signal collected using a microfabricated polynucleotide analysis device of the invention is high relative to other types of devices. Specifically, the invention allows, e.g., the use of oil-immersion high numerical apperature (N.A.) microscope objectives to collect the light (e.g., 1.4 N.A.). Since the collection of light is proportional to the square of the N.A., a 1.4 N.A. objective provides about a four-fold better signal than an 0.8 N.A. objective.

6.7. Microfabricated Cell Sorting Device

The invention also includes a microfabricated device for sorting reporter-labeled cells by the level of reporter they contain. The device is similar to polynucleotide-sorting devices described above, but is adapted for handling particles on the size scale of cells rather than molecules. This difference is manifested mainly in the dimensions of the microfabricated channels, detection and discrimination regions. Specifically, the channels in the device are typically between about 20 $\mu$m and about 500 $\mu$m in width and between about 20 $\mu$m and about 500 $\mu$m in depth, to allow for an orderly flow of cells in the channels. Similarly, the volume of the detection region in a cell sorting device is larger than that of the polynucleotide sorting device, typically being in the range of between about 10 pl and 100 nl. To prevent the cells from adhering to the sides of the channels, the channels (and coverslip) preferably contain a coating which minimizes cell adhesion. Such a coating may be intrinsic to the material from which the device is manufactured, or it may be applied after the structural aspects of the channels have been microfabricated. An exemplary coating has the surface properties of a material such as "TEFLON".

The device may be used to sort any procaryotic (e.g., bacterial) or eukaryotic (e.g., mammalian) cells which can be labeled (e.g., via antibodies) with optically-detectable reporter molecules (e.g., fluorescent dyes). Exemplary mammalian cells include human blood cells, such as human peripheral blood mononuclear cells (PBMCs). The cells can be labeled with antibodies directed against any of a variety of cell marker antigens (e.g., HLA DR, CD3, CD4, CD8, CD11a, CD11c, CD14, CD16, CD20, CD45, CD45RA, CD62L, etc.), and the antibodies can in turn be detected using an optically-detectable reporter (either via directly conjugated reporters or via labeled secondary antibodies) according to methods known in the art.

It will be appreciated that the cell sorting device and method described above can be used simultaneously with multiple optically-detectable reporters having distinct optical properties. For example, the fluorescent dyes fluorescein (FITC), phycoerythrin (PE), and "CYCHROME" (Cy5-PE) can be used simultaneously due to their different excitation and emission spectra. The different dyes may be assayed, for example, at successive detection and discrimination regions. Such regions may be cascaded as shown in FIG. 6 to provide samples of cells having a selected amount of signal from each dye.

6.8. Microfabrication of a Silicon Device

Analytical devices having microscale flow channels, valves and other elements can be designed and fabricated from a solid substrate material. Silicon is a preferred substrate material because of the well developed technology permitting its precise and efficient fabrication, but other materials may be used, including polymers such as polytetrafluoroethylenes. Micromachining methods well known in the art include film deposition processes, such as spin coating and chemical vapor deposition, laser fabrication or photolithographic techniques, or etching methods, which may be performed by either wet chemical or plasma processes. (See, for example, Angell et al. (37) and Manz et al. (38).

FIGS. 7A–7D illustrate the initial steps in microfabricating the discrimination region portion of a nucleic acid sorting device (e.g. Device 20 in FIG. 1) by photolithographic techniques. As shown, the structure includes a silicon substrate 160. The silicon wafer which forms the substrate is typically washed in a 4:1H$_2$SO$_4$/H$_2$O bath, rinsed in water and spun dry. A layer 162 of silicon dioxide, preferably about 0.5 μm in thickness, is formed on the silicon, typically by heating the silicon wafer to 800–1200° C. in an atmosphere of steam. The oxide layer is then coated with a photoresist layer 164, preferably about 1 μm inch-thickness. Suitable negative or positive resist materials are well known. Common negative resist materials include two-component bisarylazide/rubber resists. Positive resist materials include polymethyl-methacrylate (PMMA) and two component diazoquinone /phenol ic resin materials. See, e.g., "Introduction to microlithography", Thompson (36).

The coated laminate is irradiated through a photomask 166 imprinted with a pattern corresponding in size and layout to the desired pattern of the microchannels. Methods for forming photomasks having desired photomask patterns are well known. For example, the mask can be prepared by printing the desired layout on an overhead transparency using a high resolution (3000 dpi) printer. Exposure is carried out on standard equipment such as a Karl Suss contact lithography machine.

Figure 7A:
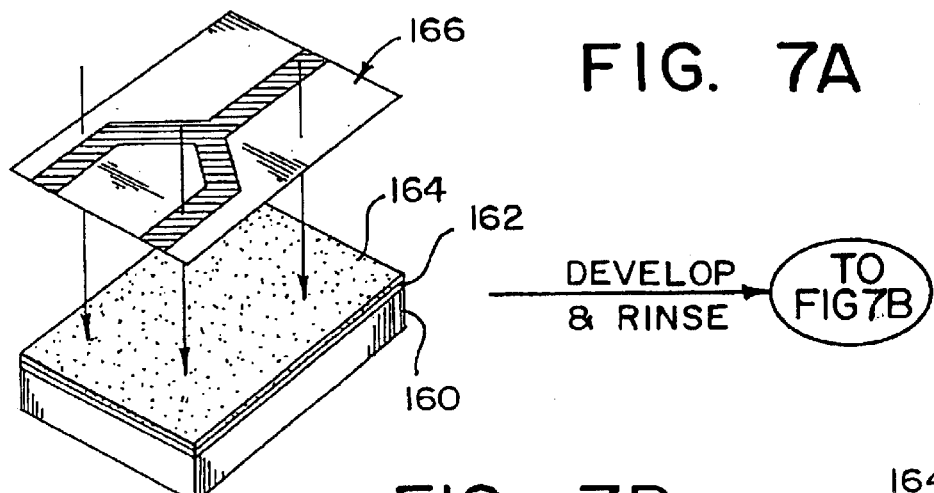
FIGS. 7A–7D show initial steps in photolithographic microfabrication of a nucleic acid sorting device from a silicon wafer, using photolithography and several stages of etching.
Figure 7B:
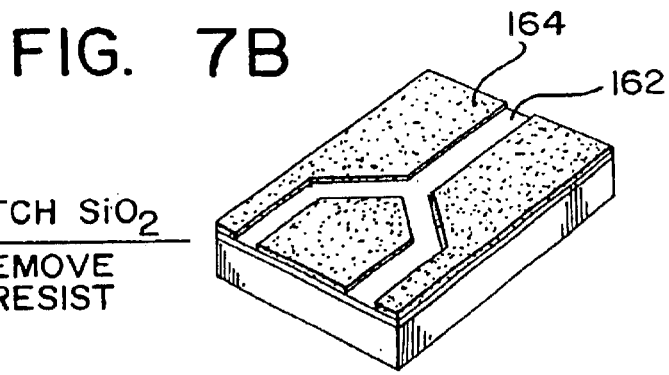
Figure 7C:
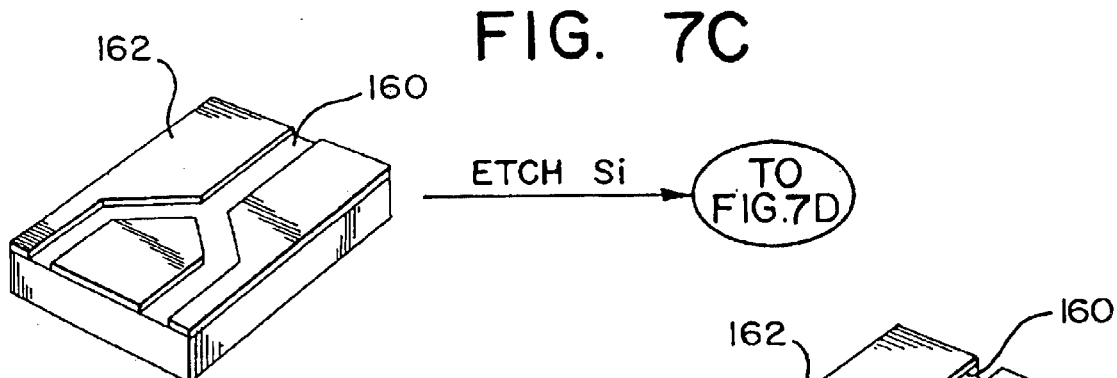
Figure 7D:
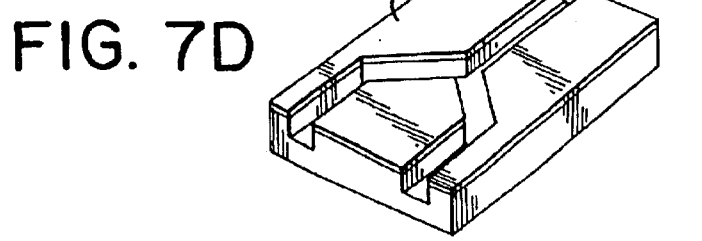

In the method illustrated in FIGS. 7A–5D, the photoresist is a negative resist, meaning that exposure of the resist to a selected wavelength, e.g., UV, light produces a chemical change that renders the exposed resist material resistant to the subsequent etching step. Treatment with a suitable etchant removes the unexposed areas of the resist, leaving a pattern of bare and resist-coated silicon oxide on the wafer surface, corresponding to the layout and dimensions of the desired microstructures. In this example, because a negative resist was used, the bare areas correspond to the printed layout on the photomask. The wafer is now treated with a second etchant material, such as a reactive ion etch (RIE), effective to dissolve the exposed areas of silicon dioxide. The remaining resist is removed, typically with hot aqueous H$_2$SO$_4$. The remaining pattern of silicon dioxide (162) now serves as a mask for the silicon (160). The channels are etched in the unmasked areas of the silicon substrate by treating with a KOH etching solution. Depth of etching is controlled by time of treatment. Additional microcomponents may also be formed within the channels by further photolithography and etching steps, as discussed below.

Depending on the method to be used for directing the flow of molecules through the device, electrodes and/or valves are fabricated into the flow channels. A number of different techniques are available for applying thin metal coatings to a substrate in a desired pattern. These are reviewed in, for example, Krutenat, Kirk-Othmer 3rd ed., Vol. 15, pp. 241–274 (32), incorporated herein by reference. A convenient and common technique used in fabrication of microelectronic circuitry is vacuum deposition.

For example, metal electrodes or contacts may be evaporated onto a substrate using vacuum deposition and a contact mask made from, e.g., a "MYLAR" sheet. Various metals such as platinum, gold, silver or indium/tin oxide (ITO) may be used for the electrodes.

Deposition techniques allowing precise control of the area of deposition are preferred for application of electrodes to the side walls of the channels in the device.

Such techniques are described, for example, in Krutenat (32), above, and references cited therein. They include plasma spraying, where a plasma gun accelerates molten metal particles in a carrier gas towards the substrate, and physical vapor deposition using an electron beam, where atoms are delivered on line-of-sight to the substrate from a virtual point source. In laser coating, a laser is focused onto the target point on the substrate, and a carrier gas projects powdered coating material into the beam, so that the molten particles are accelerated toward the substrate.

Another technique allowing precise targeting uses an electron beam to induce selective decomposition of a previously deposited substance, such as a metal salt, to a metal. This technique has been used to produce sub- micron circuit paths (e.g., 26).

6.9. Elastomeric Microfabricated Device

This Example demonstrates the manufacture of a disposable microfabricated device, which can function as a stand-alone device or as a component of an integrated microanalytical chip, in sorting molecules or cells.

Preparation of the microfabricated device. A silicon wafer was etched and fabricated as described above and in (15). After standard contact photolithography techniques to pattern the oxide surface of the silicon wafer, a $C_2F_2$/CHF$_3$ gas mixture was used to etch the wafer by RIE. The silicon wafer was then subjected to further etch with KOH to expose the silicon underneath the oxide layer, thereby forming a mold for the silicone elastomer. The silicon mold forms a "T" arrangement of channels. The dimensions of the channels may range broadly, having approximately 5×4 μm dimension.

Figure 8:
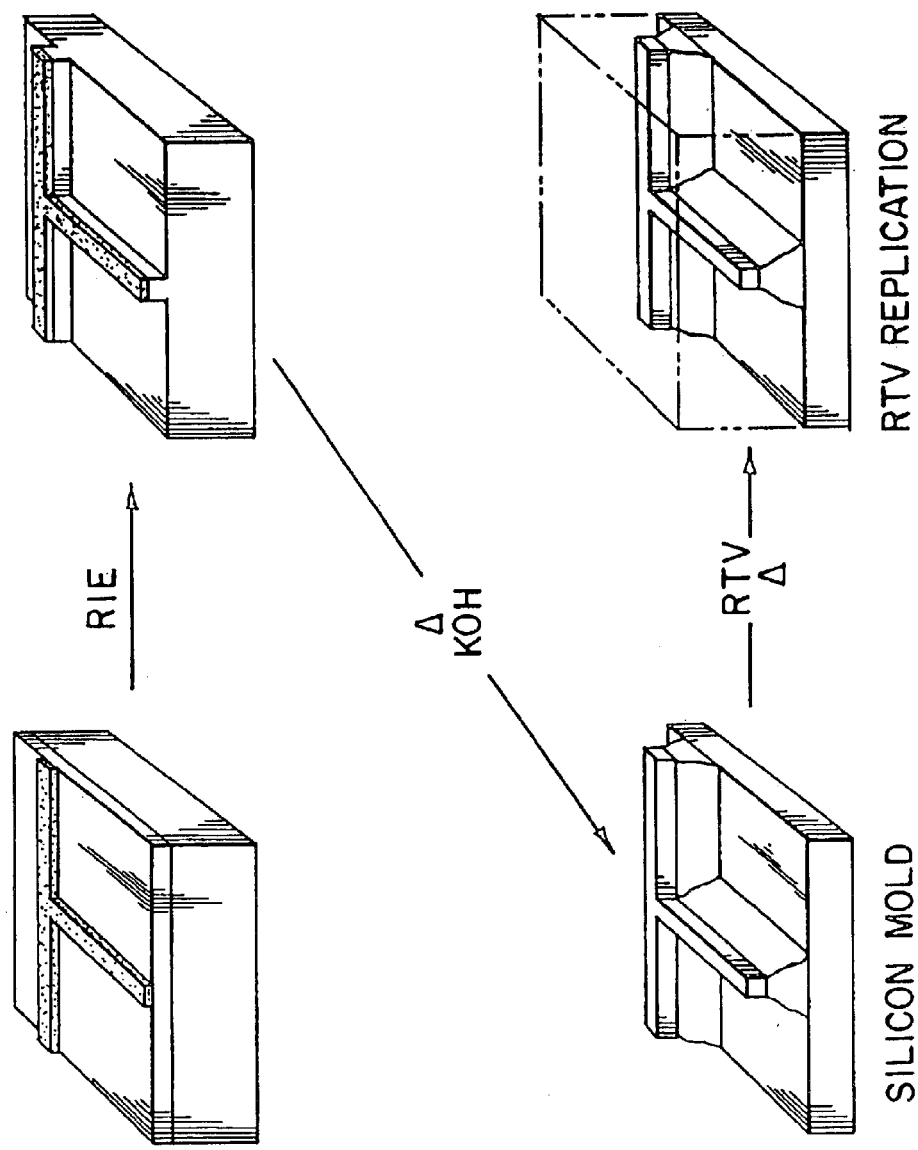
FIG. 8 shows a schematic representation of a process for obtaining a silicone elastomer impression of a silicon mold to provide a microfabricated chip according to the invention.

The etching process is shown schematically in FIG. 8. Standard micromachining techniques were used to create a negative master mold out of a silicon wafer. The disposable silicone elastomer chip was made by mixing General Electric RTV 615 components (20) together and pouring onto the etched silicon wafer. After curing in an oven for two hours at 80° C., the elastomer was peeled from the wafer and bonded hermetically to a glass cover slip for sorting. To make the elastomer hydrophilic the elastomer chip was immersed in HCl (pH=2.7) at 60 degrees C. for 40 to 60 min. Alternatively, the surface could have been coated with polyurethane (3% w/v in 95% ethanol and diluted 10× in ethanol). It is noted that the master wafer can be reused indefinitely. The device shown has channels that are 100 μm wide at the wells, narrowing to 3 μm at the sorting junction (discrimination region). The channel depth is 4 μm, and the wells are 2 mm in diameter. These dimensions can be modified according to the size range of the molecules or cells to be analyzed or sorted.

Figure 9:
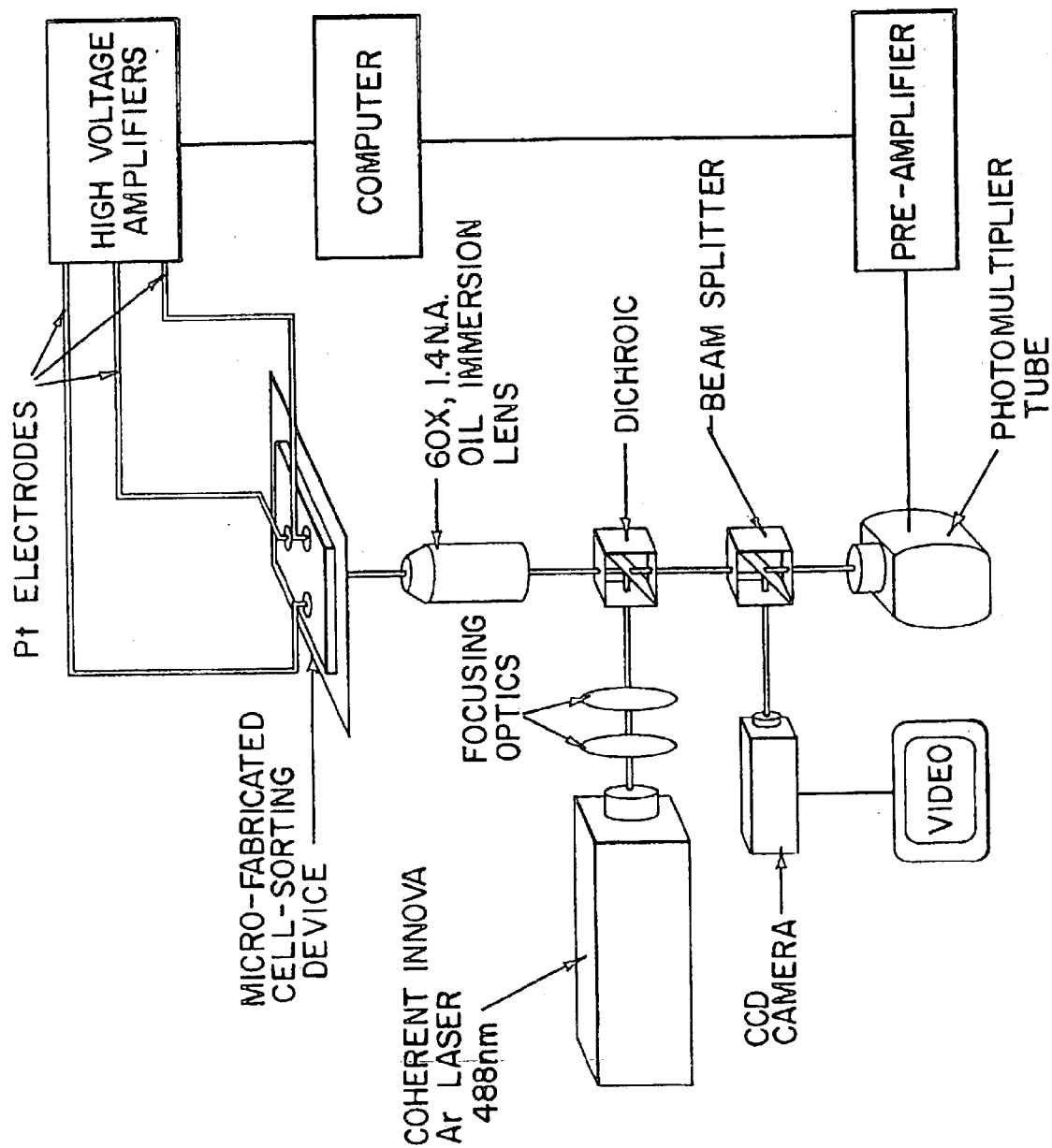
FIG. 9 shows a schematic representation of an apparatus of the invention, in which a silicone elastomer chip is mounted on an inverted microscope for optical detection of a laser-stimulated reporter. Electrodes are used to direct cells in response to the microscope detection.
Figure 10:
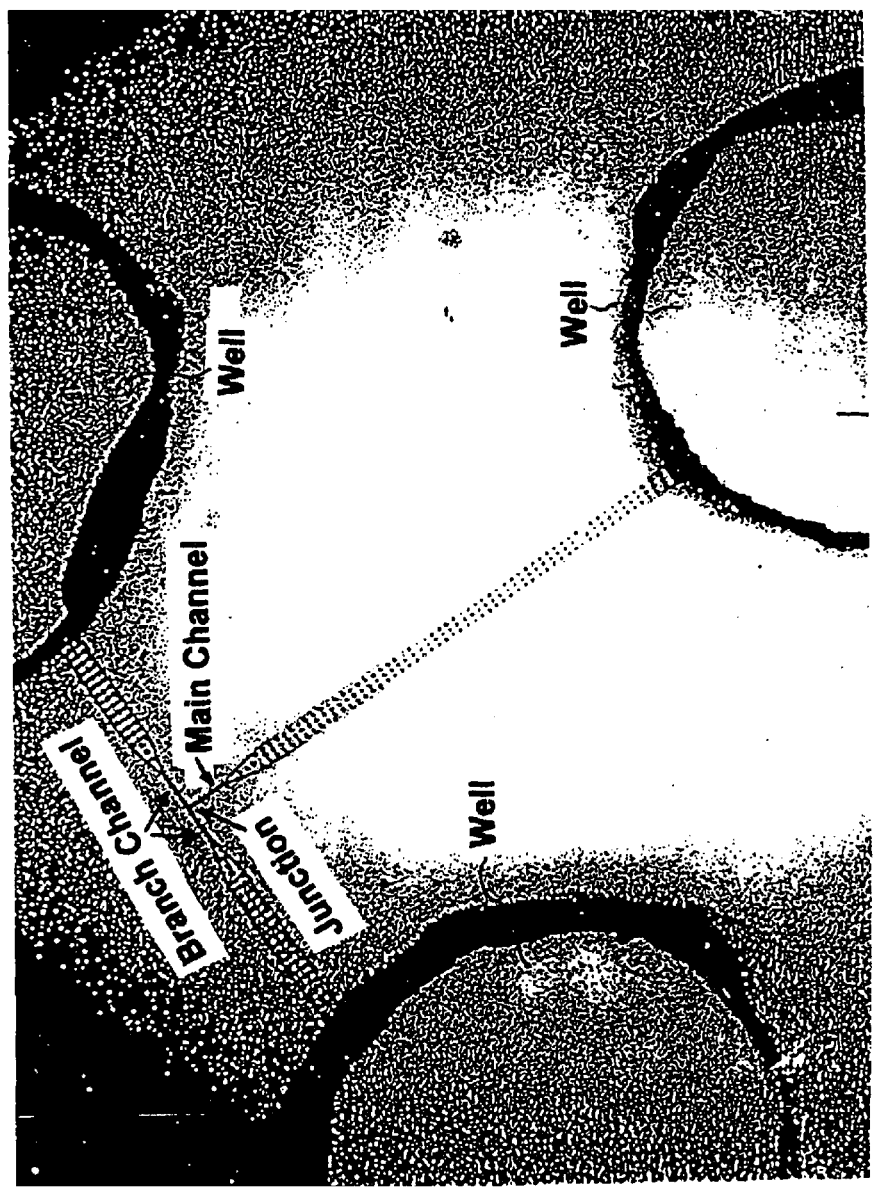
FIG. 10 is a photograph of an apparatus of the invention, showing a chip with an inlet channel and reservoir, a detection region, a branch point, and two outlet channels with reservoirs.

Detection Apparatus. In this embodiment the device was mounted on an inverted optical microscope (Zeiss Axiovert 35) as shown in FIG. 9. In this system, the flow control can be provided by voltage electrodes for electro-osmotic control or by capillaries for pressure-driven control. The detection system can be photomultiplier tubes or photodiodes, depending upon the application. The inlet well and two collection wells were incorporated into the elastomer chip on three sides of the "T" forming three channels (FIG. 7). The chip was adhered to a glass coverslip and mounted onto the microscope.

6.10. Operation of a Polynucleotide Analysis Device

The operation of a polynucleotide analysis chip is described. This example refers to polynucleotides, but it will be appreciated that other molecules may be analyzed or sorted using similar methods and devices. Likewise, cells can be processed using similar methods and devices, adapted to the appropriate size.

A solution of reporter-labeled polynucleotides is prepared as described below and introduced into the sample inlet end(s) of the analysis unit(s). The solution may be conveniently introduced into a reservoir, such as reservoir 48 of FIG. 1, via a port or connector, such as connector 70 in FIG. 2, adapted for attachment to a segment of tubing, such as liquid chromatography or HPLC tubing.

It is typically advantageous to "hydrate" the device (i.e., fill the channels of the device with the solvent, e.g., water or a buffer solution, in which the polynucleotides will be suspended) prior to introducing the polynucleotide-containing solution. Such hydrating can be achieved by supplying water or the buffer solution to the device reservoir and applying hydrostatic pressure to force the fluid through the analysis unit(s).

Following such hydration, the polynucleotide-containing solution is introduced into the sample inlets of the analysis unit(s) of the device. As the stream of labeled polynucleotides (e.g., tagged with a reporter such as a fluorescent dye) is passed in a single file manner through the detection region, the optical signal (e.g., fluorescence) from the optically-detectable reporter moieties on each molecule are quantitated by an optical detector and converted into a number used in calculating the approximate length of polynucleotide in the detection region.

Exemplary reporter moieties, described below in reference to sample preparation, include fluorescent moieties which can be excited to emit light of characteristic wavelengths by an excitation light source. Fluorescent moieties have an advantage in that each molecule can emit a large number of photons (e.g., upward of 106) in response to exciting radiation. Suitable light sources include lasers, laser diodes, high-intensity lamps, e.g., mercury lamps, and the like. In embodiments where a lamp is used, the channels are preferably shielded from the light in all regions except the detection region, to avoid bleaching of the label. In embodiments where a laser is used, the laser can be set to scan across a set of detection regions from different analysis units. Other optically-detectable reporter moieties include chemiluminescent moieties, which can be used without an excitation light source.

Where laser diodes are used as a light source, the diodes may be microfabricated into the same chip that contains the analysis units. Alternatively, the laser diodes may be incorporated into a second chip (laser diode chip; LDC) that is placed adjacent to the chip such that the laser light from the diodes shines on the detection regions. The photodiodes in the LDC are preferably placed at a spacing that corresponds to the spacing of the detection regions in the chip.

The level of reporter signal is measured using an optical detector, such as a photodiode (e.g., an avalanche photodiode), a fiber-optic light guide leading, e.g, to a photomultiplier tube, a microscope with a high numerical apperature (N.A.) objective and an intensified video camera, such as a SIT camera, or the like. The detector may be microfabricated or placed into the PAC itself (e.g., a photodiode as illustrated in FIGS. 3A and 3B), or it may be a separate element, such as a microscope objective.

In cases where the optical detector is a separate element, it is generally necessary to restrict the collection of signal from the detection region of a single analysis unit. It may also be advantageous to scan or move the detector relative to the polynucleotide analysis unit ("PAC"), preferably by automation. For example, the PAC can be secured in a movable mount (e.g., a motorized/computer-controlled micromanipulator) and scanned under the objective. A fluorescence microscope, which has the advantage of a built-in excitation light source (epifluorescence), is preferably employed for detection of a fluorescent reporter.

Since current microfabrication technology enables the creation of sub-micron structures employing the elements described herein, the dimensions of the detection region are influenced primarily by the size of the molecules under study. These molecules can be rather large by molecular standards. For example, lambda DNA (~50 kb) in solution has a diameter of approximately 0.5 $\mu$m. Accordingly, detection regions used for detecting polynucleotides in this size range have a cross-sectional area large enough to allow such a molecule to pass through without being substantially slowed down relative to the flow of the solution carrying it and causing a "bottle neck". The dimensions of a channel should therefore be at least about twice, preferably at least about five times as large per side or in diameter as the diameter of the largest molecule that will be passing through it.

Another factor important to consider in the practice of the present invention is the optimal concentration of polynucleotides in the sample solution. The concentration should be dilute enough so that a large majority of the polynucleotide molecules pass through the detection region one by one, with only a small statistical chance that two or more molecules pass through the region simultaneously. This is to insure that for the large majority of measurements, the level of reporter measured in the detection region corresponds to a single molecule, rather than two individual molecules.

The parameters which govern this relationship are the volume of the detection region and the concentration of molecules in the sample solution. The probability that the detection region will contain two or more molecules ($P_{>2}$) can be expressed as $$P_{\geq 2} = 1 - \{1 + [DNA]^* V\} * e^{-[DNA]^* V}$$

where [DNA] is the concentration of polynucleotides in units of molecules per $\mu m^3$ and V is the volume of the detection region in units of $\mu m^3$.

It will be appreciated that $P_{\geq 2}$ can be minimized by decreasing the concentration of polynucleotides in the sample solution. However, decreasing the concentration of polynucleotides in the sample solution also results in increased volume of solution processed through the device and can result in longer run times. Accordingly, the objectives of minimizing the simultaneous presence of multiple molecules in the detection chamber (to increase the accuracy of the sorting) needs to be balanced with the objective of generating a sorted sample in a reasonable time in a reasonable volume containing an acceptable concentration of polynucleotide molecules.

The maximum tolerable $P_{\geq 2}$ depends on the desired "purity" of the sorted sample. The "purity" in this case refers to the fraction of sorted polynucleotides that are in the specified size range, and is inversely proportional to $P_{>2}$.

For example, in applications where high purity is not required, such as the purification of a particular restriction fragment from an enzymatic digest of a portion of vector DNA, a relatively high $P_{>2}$ (e. g., $P_{>2}$ =0.2) may be acceptable. For most applications, maintaining $P_{>2}$ at or below about 0.1 provides satisfactory results.

In an example where $P_{\geq 2}$ is equal 0.1, it is expected that in about 10% of measurements, the signal from the detection region will be due to the presence of two or more polynucleotide molecules. If the total signal from these molecules is in the range corresponding to the desired size fragment, these (smaller) molecules will be sorted into the channel or tube containing the desired size fragments.

The DNA concentration needed to achieve a particular value $P_{>2}$ in a particular detection volume can be calculated from the above equation. For example, a detection region in the shape of a cube 1 $\mu m^3$ per side has a volume of 1 femtoliter (fl). A concentration of molecules resulting, on average, in one molecule per fl, is about 1.7 nM. Using a P22 of about 0.1, the polynucleotide concentration in a sample analyzed or processed using such a 1 fl detection region volume is approximately 0.85 nM, or roughly one DNA molecule per 2 detection volumes ($[DNA]*V=\sim 0.5$). If the concentration of DNA is such that $[DNA]*V$ is 0.1, $P_{>2}$ is less than 0.005; i.e., there is less than a one half of one percent chance that the detection region will at any given time contain two of more fragments.

The signal from the optical detector is routed, e.g., via electrical traces and pins on the chip, to a processor, which processes the signals into values corresponding to the length of the polynucleotide giving rise to the signal. These values are then compared, by the processor, to pre-loaded instructions containing information on which branch channel molecules of a particular size range will be routed into. Following a delay period that allows the molecule from which the reporter signal originated to arrive at the discrimination region, the processor sends a signal to actuate the active elements in the discrimination region such that the molecule is routed into the appropriate branch channel.

The delay period is determined by the rate at which the molecules move through the channel (their velocity relative to the walls of the channel) and the length of the channel between the detection region and the discrimination region. In cases where the sample solution is moved through the device using hydrostatic pressure (applied, e.g., as pressure at the inlet end and/or suction at the outlet end), the velocity is typically the flow rate of the solution. In cases where the molecules are pulled through the device using some other means, such as via electro-osmotic flow with an electric field set up between the inlet end and the outlet end, the velocity as a function of molecule size can be determined empirically by running standards, and the velocity for a specific molecule calculated based on the size calculated for it from the reporter signal measurement.

A relevant consideration with respect to the velocity at which the polynucleotide molecules move through the device is the shear force that they may be subject to. At the channel dimensions contemplated herein, the flow through the channels of the device is primarily laminar flow with an approximately parabolic velocity profile. Since the cross-sectional area of the channels in the device can be on the same order of magnitude as the diameter of the molecules being analyzed, situations may arise where a portion of a particular molecule is very near the wall of the channel, and is therefore in a low-velocity region, while another portion of the molecule is near the center of the channel, i.e., in a high-velocity region. This situation creates a shear force (F) on the molecule, which can be estimated using the following expression:

$$F=6\pi\eta R_\lambda V$$

where $R_\lambda$ is the radius of the molecule and $\eta$ is the viscosity of the solution. This expression assumes that the molecule is immobilized on a stationary surface and subject to uniform flow of velocity V.

The amount of force necessary to break a double stranded fragment of DNA is approximately 100 pN. Accordingly, the maximal shear force that the molecules are subjected to should preferably be kept below this value. Substituting appropriate values for the variables in the above expression for lambda DNA yields a maximum velocity of about 1 cm/sec for a channel 1 $\mu$m in radius (i.e., a channel of a dimension where one portion of the lambda molecule can be at or near the wall of the channel with the opposite side in the center of the channel). Since devices designed for use with such large molecules will typically have channels that are considerably larger in diameter, the maximum "safe" velocity will typically be greater than 1 cm/sec.

As discussed above, the sample solution introduced into a device of the invention should be dilute enough such that there is a high likelihood that only a single molecule occupies the detection region at any given time. It follows then that as the solution flows through the device between the detection and discrimination regions, the molecules will be in "single file" separated by stretches of polynucleotide-free solution. The length of the channel between the detection and discrimination region should therefore not be so long as to allow random thermal diffusion to substantially alter the spacing between the molecules. In particular, the length should be short enough that it can be traversed in a time short enough such that even the smallest molecules being analyzed will typically not be able to diffuse and "switch places" in the line of molecules.

The diffusion constant of a 1 kb molecule is approximately 5 $\mu m^2$/sec; the diffusion equation gives the distance that the molecule diffuses in time t as:

$$<X^2>\sim Dt$$

Using this relationship, it can be appreciated that a 1 kbp fragment takes about 0.2 seconds to diffuse 1 $\mu$m. The average spacing of molecules in the channel is a function of the cross-sectional area of the channel and the molecule concentration, the latter being typically determined in view of acceptable values of $P_{>2}$ (see above). From the above relationships, it is then straightforward to calculate the maximum channel length between the detection and discrimination region which would ensure that molecules don't "switch places". In practice, the channel length between the detection and discrimination regions is between about 1 $\mu$m and about 2 cm.

As illustrated above with respect to FIGS. 5A–D, there are a number of ways in which molecules can be routed or sorted into a selected branch channel. For example, in a device employing the discrimination region shown in FIG. 4A, the solution is preferably moved through the device by hydrostatic pressure. Absent any field applied across electrodes 110 and 112, a molecule would have an equal probability of entering one or the other of the two branch channels 106 and 108. The sorting is accomplished by the processor temporarily activating a voltage source connected to the electrode leads 114 and 116 just before or at the time the molecule to be routed enters the junction of the main channel and the two branch channels. The resulting electric field exerts a force on the negatively-charged DNA molecule biasing it toward the positively-charged electrode. The molecule will then be carried down the branch channel containing the positively-charged electrode by the bulk solution flow. The electric field is turned off when the molecule has committed itself to the selected channel. As soon as the molecule clears the corner from the discrimination region and into the branch channel, it escapes effects of the electric field that will be applied to the next molecule in the solution stream.

The discrimination region shown in FIG. 5B is designed for use in a device that employs electroosmotic flow, rather than flow induced by hydrostatic pressure, to move both the polynucleotides and bulk solution through the device. Electrodes are set up in the channels at the inlet and outlet ends of the device. Application of an electric field at the ends of the channels (with electrode 130 being negative, and electrodes 132 and 134 being positive) sets up bulk solution flow according to well -established principles of electroosmotic flow (see, e.g., 25). When a specific polynucleotide molecule enters the junction region between the main channel and the two branch channels, the voltage to one of either electrodes 132 or 134 is shut off, leaving a single attractive force, acting on the solution and the DNA molecule, into the selected branch channel. As above, both branch channel electrodes are activated after the molecule has committed to the selected branch channel in order to continue bulk flow through both channels.

In another embodiment of the invention the polynucleotides are directed into a selected branch channel via a valve in the discrimination region. An exemplary valve is shown in FIG. 5C. The valve consists of a thin extension of material 140 which can be charged via an electrode 142. The extension can then be deflected to close one or the other of the branch channels by application of an appropriate voltage across electrodes 144 and 146. As above, once the molecule has committed, the voltage can be turned off.

In a device in which the sample solution is moved through the device by application of positive pressure at the sample inlet end(s) of the analysis unit(s), the discrimination function may be affected by simply blocking branch channel sample outlets into which the sample is not supposed to go, and leaving the selected outlet open. Due to the small size scale of the channels and the incompressibility of liquids, blocking the solution flow creates an effective "plug" in the unselected branch channels, routing the molecule along with the bulk solution flow into the selected channel. This embodiment is illustrated in FIG. 4D. It can be achieved by, for example, incorporating valve structures downstream of the discrimination region.

Alternatively, the discrimination function may be affected by changing the hydrostatic pressure at the sample outlets of the branch channels into which the sample is not supposed to go. Specifically, if the branch channels in a particular analysis unit all offer the same resistance to fluid flow, and the pressure at the sample inlet of the main channel of an analysis unit is P, then the fluid flow out of any selected branch channel can be stopped by applying a pressure P/n at the sample outlet of that branch channel, where n is the number of branch channels in that analysis unit. Accordingly, in an analysis unit having two branch channels, the pressure applied at the outlet of the branch to be blocked is P/2.

It will be appreciated that the position and fate of the molecules in the discrimination region can be monitored by additional detection regions installed, e.g., immediately upstream of the discrimination region and/or in the branch channels immediately downstream of the branch point. This information be used by the processor to continuously revise estimates of the velocity of the molecules in the channels and to confirm that molecules having selected size characteristics end up in the selected branch channel.

Solution from the branch channels is collected at the outlet ends of the analysis units. As described above, devices with a plurality of analysis units typically collect the solution from corresponding branch channels of each unit into a manifold, which routes the solution flow to an outlet port, which can be adapted for receiving, e.g., a segment of tubing or a sample tube, such as a standard 1.5 ml centrifuge tube.

The time required to isolate a desired quantity of polynuclectide depends on a number of factors, including the size of the polynucleotide, the rate at which each analysis unit can process the individual fragments, and the number of analysis units per chip, and can be easily calculated using basic formulas. For example, a chip containing 1000 analysis units, each of which can sort 1000 fragments per second, could isolate 0.1 $\mu$g of 10 kb DNA in about 2.5 hours.

Other Microfabricated Devices

Operation of a microfabricated cell sorting device is essentially as described above with respect to the polynucleotide sorting device. Since cells typically do not have predictable a net charge, the directing means are preferably ones employing a valve in the discrimination region as described above, or flow stoppage, either by valve or hydrostatic pressure.

Operation of a microfabricated analysis device is accomplished essentially as is described above, except that functions relating to sorting polynucleotide molecules into branch channels don't need to be performed. The processor of such analysis devices is typically connected to a data storage unit, such as computer memory, hard disk or the like, as well as to a data output unit, such as a display monitor, printer and/or plotter. The sizes of the polynucleotide molecules passing through the detection region are calculated and stored in the data storage unit. This information can then be further processed and/or routed to the data output unit for presentation as, e.g., histograms of the size distribution of DNA molecules in the sample. The data can, of course, be presented in real time as the sample is flowing through the device, allowing the practitioner of the invention to continue the run only as long as is necessary to obtain the desired information.

In preferred molecular (e.g. DNA, polynucleotide or polypeptide) analysis and sorting embodiments, a microfabricated chip of the invention has a detection volume of about 10 to about 5000 femtoliters (fl), preferably about 50 to about 1000 fl, and most preferably on the order of about 200 fl. In preferred cell analysis and sorting embodiments, a microfabricated chip of the invention has a detection volume of approximately 1 to 1,000,000 femtoliters (fl), preferably about 200 to 500 fl, and most preferably about 375 fl.

Exemplary Embodiment and Additional Parameters

Microfluidic Chip Fabrication. In a preferred embodiment, the invention provides a "T" on "Y" shaped series of channels molded into optically transparent silicone rubber or PolyDiMethylSiloxane (PDMS), preferably PDMS. This is cast from a mold made by etching the negative image of these channels into the same type of crystalline silicon wafer used in semiconductor fabrication.

As described above, the same techniques for patterning semiconductor features are used to form the pattern of the channels. The uncured liquid silicone rubber is poured onto these molds placed in the bottom of a Petri dish. To speed the curing, these poured molds are baked. After the PDMS has cured, it is removed from on top of the mold and trimmed. In a chip with one set of channels forming a "T", three holes are cut into the silicone rubber at the ends of the "T", for example using a hole cutter similar to that used for cutting holes in cork, and sometimes called cork borers. These holes form the sample, waste and collection wells in the completed device. In this example, the hole at the bottom end of the T is used to load the sample. The hole at one arm of the T is used for collecting the sorted sample while the opposite arm is treated as waste. Before use, the PDMS device is placed in a hot bath of HCl to make the surface hydrophilic. The device is then placed onto a No. 1 (150 $\mu$m thick) (25×25 mm) square microscope cover slip. The cover slip forms the floor (or the roof) for all three channels and wells. The chip has a detection region as described above.

Any of or all of these manufacturing and preparation steps can be done by hand, or they can be automated, as can the operation and use of the device.

The above assembly is placed on an inverted Zeiss microscope. A carrier holds the cover slip so that it can be manipulated by the microscope's x-y positioning mechanism. This carrier also has mounting surfaces which support three electrodes, which implement the electro-osmotic and/ or electrophoretic manipulation of the cells or particles to be analyzed and sorted. The electrodes are lengths of platinum wire taped onto a small piece of glass cut from a microscope slide. The wire is bent into a hook shape, which allows it to reach into one of the wells from above. The cut glass acts as a support platform for each of the electrodes. They are attached to the custom carrier with double-sided tape. This allows flexible positioning of the electrodes. Platinum wire is preferred for its low rate of consumption (long life) in electrophoretic and electro-osmotic applications, although other metals such as gold wire may also be used.

Device Loading. To operate the device for sorting, one of the wells, e.g. the collection or waste well, is first filled with buffer. All three channels, starting with the channel connected to the filled well, wick in buffer via capillary action and gravity. Preferably, no other well is loaded until all the channels fill with buffer, to avoid the formation of air pockets. After the channels fill the remaining wells can be loaded with buffer, as needed, to fill or equilibrate the device. The input or sample well is typically loaded last so that the flow of liquid in the channels is initially directed towards it. Generally, equal volumes of buffer or sample are loaded into each well. This is done in order to prevent a net flow of liquid in any direction once all of the wells are loaded, including loading the sample well with sample. In this embodiment, it is preferred that the flow of material through the device (i.e. the flow of sample) be driven only by the electrodes, e.g. using electro-osmotic and/or electrophoretic forces. The electrodes may be in place during loading, or they can be placed into the wells after loading, to contact the buffer.

Electrodes. Two of the above electrodes are driven by high voltage operational amplifiers (op-amps) capable of supplying voltages of +−150 V. The third electrode is connected to the electrical ground (or zero volts) of the high voltage op-amp electronics. For sorting operation the driven electrodes are placed in the collection and waste wells. The ground electrode is placed in the sample well. The op-amps amplify, by a factor of 30, a control voltage generated by two digital to analog converters (DACs). The maximum voltage these DACs generate is +−5 V, which determines the amplification factor of 30. The 150 V limit is determined by the power supply to the amplifiers, which are rated for +−175 V. These DACs reside on a card (a Lab PC 1200 Card, available from National Instruments, Austin, Tex.) mounted in a personal computer. The card also contains multiple channels of analog to digital converters (ADC's) one of which is used for measuring the signal generated by photomultiplier tubes (PMTs). This card contains two DACs. A third DAC can be used to drive the third electrode with an additional high voltage op amp. This would provide a larger voltage gradient, if desired, and some additional operational flexibility.

Without being bound by any theory, it is believed that the electrodes drive the flow of sample through the device using electro-osmotic or electrophoretic forces, or both. To start the movement of molecules, cells or particles to be sorted, a voltage gradient is established in the channels. This is done by generating a voltage difference between electrodes.

In this example, the voltage of the two driven electrodes is raised or lowered with respect to the grounded electrode. The voltage polarity depends on the charge of the molecules, cells or particles to be sorted (if they are charged), on the ions in the buffer, and on the desired direction of flow. Because the electrode at the sample well in the examples is always at zero volts with respect to the other two electrodes, the voltage at the "T" intersection or branch point will be at a voltage above or below zero volts, whenever the voltage of the other two electrodes is raised or lowered. Typically, the voltage is set or optimized, usually empirically, to produce a flow from the sample well, toward a downstream junction or branch point where two or more channels meet. In this example, where two channels are used, one channel is typically a waste channel and terminates in a waste well; the other channel is a collection channel and terminates in a collection well.

To direct the molecules, particles or cells to a particular channel or arm of the "T" (e.g. collection or waste), the voltage at the electrode in one well (or multiple wells, in multi-channel embodiments) is made the same as the voltage at the junction or branch point, where the channels meet. The voltage of the electrode at one well of the two or more wells is raised or lowered, to produce a gradient between that well and the branch point. This causes the flow to move down the channel towards and into the well, in the direction produced by the gradient. Typically, the voltage of the electrode at the waste well is raised or lowered with respect to the voltage at the collecting well, to direct the flow into the waste channel and the waste well, until a molecule, particle or cell is identified for collection. The flow is diverted into the collection channel and collection well by adjusting the voltages at the electrodes to eliminate or reduce the gradient toward the waste well, and provide or increase the gradient toward the collection well. For example, in response to a signal indicating that a molecule or cell has been detected for sorting, by examination in a detection region upstream of the branch point, the voltage at the waste and collection points can be switched, to divert the flow from one channel and well to the other.

The voltage at the branch point (the intersection voltage) is determined by the voltage gradient desired (e.g. Volts/ mm) times the distance from the sample well electrode to the branch point (gradient x distance), which in this example is placed where all of the channels of the "T" intersect. The gradient also determines the voltage at the waste or collection electrode(gradient×distance from sample well to collection well).

Conceptually, the channels and wells of the "T" can be treated as a network of three resistors. Each segment of the "T" behaves as a resistor whose resistance is determined by the conductivity of the buffer and the dimensions of the channel. A voltage difference is provided across two of the resistors, but not the third. If the electrodes in each of the three wells is equidistant from the branch point, then each channel will have the same resistance.

For example, assume that each section of the "T" has 100 K ohms of resistance. If 100 volts is applied across two of the resistors and the third resistor is left unconnected, the current at the junction of the two resistors would be 50 volts. If a voltage source of 50 volts is connected to the end of the third resistor, the voltage at the junction does not change. That is, a net of zero volts is established across the third resistor; there is no voltage gradient and a flow is not initiated or changed. If a different voltage is applied, a gradient can be established to initiate or direct the flow into one channel or another. For example, to change the direction of flow from one arm of the "T" to the other, the voltage values of the two driven electrodes are swapped. The junction voltage remains the same. If the electrode distances from the "T" intersection are not equal, then the voltages can be adjusted to accommodate the resulting differences in the effective channel resistance. The end result is still the same. The electrode in the well of the channel which is temporarily designated not to receive particles or cells is set at the voltage of the"T" intersection. The voltage at the other driven electrode is set to provide a gradient that directs molecule, cell or particle flow into that well. Thus, cells or particles can be sent down one channel or another, and ultimately into one well or another, by effectively opening one channel with a net or relative voltage gradient while keeping the other channel or channels closed by a net or relative voltage gradient of zero.

In a preferred embodiment for sorting according to the invention, a slight flow down the channel that is turned "off" is desired. This keeps the molecules or cells moving away from the branch point (the "T" junction), particularly those which have already been directed to that channel. Thus, a small non-zero gradient is preferably established in the "off" or unselected channel. The selected channel is provided with a significantly higher gradient, to quickly and effectively divert the desired molecules or cells into that channel.

The placement of the wells and their electrodes with respect to the branch point, and in particular their distance from the branch point, is an important factor in driving the flow of molecules or cells as desired. As the wells and electrodes are brought closer to the branch point, it becomes more important to precisely place the electrodes, or precisely adjust the voltages.

Detection Optics. In this example, a Ziess Axiovert 35 inverted microscope is used for detection of molecules or cells for sorting. The objective lens of this microscope faces up, and is directed at the detection region of the described microfluidic chip, through the coverslip which in this example is the floor of the device. This microscope contains all the components for epifluorescence microscopy. See, Inoue pp 67–70, 91–97 (52). In this embodiment a mercury arc lamp or argon ion laser is used as the light source. The mercury lamp provides a broad spectrum of light that can excite many different fluorophores. The argon ion laser has greater intensity, which improves the detection sensitivity but is generally restricted to fluorophores that excite at 488 or 514 nm. The mercury lamp is used, for example, to sort beads as described elsewhere herein. The laser is used for sorting sorting GFP *E. coli* bacterial cells as described elsewhere herein. The high power argon ion beam is expanded to fill the illumination port of the microscope, which matches the optical characteristics of the mercury arc lamp and provides a fairly uniform illumination of the entire image area in a manner similar to the mercury lamp. However, it is somewhat wasteful of the laser light. If a lower powered laser is used, the laser light is focused down to coincide with the detection region of the chip, to achieve the same or similar illumination intensity and uniformity with less power consumption.

The objective used in the example is an Olympus PlanApo 60×1.4 N.A. oil immersion lens. The optics are of the infinity corrected type. An oil immersion lens enables collecting a substantial percentage of the 180 degree hemisphere of emitted light from the sample. This enables some of the highest sensitivity possible in fluorescence detection. This microscope has 4 optical ports including the ocular view port. Each port, except the ocular, taps ~20% of the available light collected from the sample when switched into the optical path. Only the ocular port can view 100% of the light collected by the objective. In this embodiment, a color video camera is mounted on one port, another has a Zeiss adjustable slit whose total light output is measured with a photomultiplier tube (PMT). The fourth port is not used.

The microscope focuses the image of the sample onto the plane of the adjustable slit. An achromatic lens collimates the light from the slit image onto the active area of the PMT. Immediately in front of the PMT window an optical band pass filter is placed specific to the fluorescence to be detected. The PMT is a side on-type and does not have a highly uniform sensitivity across its active area. By relaying the image to the PMT with the achromat, this non-uniformity is averaged and its effect on the measured signal is greatly minimized. This also enables near ideal performance of the bandpass filter. A 20% beam splitter has been placed in the light path between the achromat and filter. An ocular with a reticle re-images this portion of the collimated light. This enables viewing the adjustable slit directly, to insure that the detection area that the PMT measures is in focus and aligned. The adjustable slit allows windowing a specific area of the channel for detection. Its width, height, and x,y position are adjustable, and conceptually define a detection region on the chip. In this embodiment, the microscope is typically set to view a 5 $\mu$m (micron) length of the channel directly below the "T" intersection.

The PMT is a current output device. The current is proportional to the amount of light incident on the photocathode. A transimpedance amplifier converts this photocurrent to a voltage that is digitized by the Lab PC 1200 card. This allows for interpreting the image to select cells or particles having an optical reporter for sorting, as they pass through the detection region, based for example on the amount of light or fluorescence measured as an indication of whether a cell or particle has a predetermined level of reporter and should be chosen for collection. Voltages at the electrodes of the chip can be adjusted or switched according to this determination, for example by signals initiated by or under the control of a personal computer acting in concert with the Lab PC1200 card.

Absorbence Detection. In another embodiment for detecting cells or molecules, absorbence detection is employed, which typically uses relatively longer wavelengths of light, e.g., ultraviolet (UV). Thus, for example, a UV light source can be employed. Additional objective lenses can be used to image a detection region, such that the lenses are preferably positioned from the top surface if the PDMS device is made reasonably thin. Measurement of the light transmitted, i e., not absorbed by the particle or cell, using an adjustable slit, e.g., a Zeiss adjustable slit as described above, is similar to that used in fluorescence detection. A spectrophotometer may also be used. As molecules, particles or cells pass through the detection window they attenuate the light, permitting detection of a desired characteristic or the lack thereof. This can improve the accuracy of the particle sorting, for example, when sorting based on an amount of a characteristic, rather than presence of the characteristic alone, or to confirm a signal.

It is noted that in some cases, detection by absorbence may be detrimental at certain wavelengths of light to some biological material, e.g., *E. coli* cells at shorter (UV) wavelengths. Therefore, biological material to be sorted in this manner should first be tested first under various wavelengths of light using routine methods in the art. Preferably, a longer wavelength can be selected which does not damage the biological material of interest, but is sufficiently absorbed for detection.

Optical trapping. In another embodiment, an optical trap, or laser tweezers, may be used to sort or direct molecules or cells in a PDMS device of the invention. One exemplary method to accomplish this is to prepare an optical trap, methods for which are well known in the art, that is focused at the "T" intersection proximate to, and preferably downstream of, the detection region. Different pressure gradients are established in each branch. A larger gradient at one branch channel creates a dominant flow of molecules, particles or cells, which should be directed into the waste channel. A second, smaller gradient at another branch channel should be established to create a slower flow of fluid from the "T" intersection to another channel for collection. The optical trap remains in an "off" mode until a desired particle is detected at the detection region. After detection of a desired characteristic, the particle or cell is "trapped", and thereby directed or moved into the predetermined branch channel for collection. The molecule or cell is released after it is committed to the collection channel by turning off the trap laser. The movement of the cell or molecule is further controlled by the flow into the collection well. The optical trap retains its focus on the "T" intersection until the detection region detects the next molecule, cell or particle.

Flow control by optical trapping permits similar flexibility in buffer selection as a pressure driven system. In addition, the pressure gradients can be easily established by adjusting the volume of liquid added to the wells. However, it is noted that the flow rate will not be as fast when the pressure in one channel is above ambient pressure and pressure in another is below.

Forward Sorting. In an electrode-driven embodiment, prior to loading the wells with sample and buffer and placing the electrodes, the electrode voltages are set to zero. Once the sample is loaded and the electrodes placed, voltages for the driven electrodes are set, for example using computer control with software that prompts for the desired voltages, for example the voltage differential between the sample and waste electrodes. If the three wells are equidistant from the "T" intersection, one voltage will be slightly more than half the other. In a typical run, the voltages are set by the program to start with directing the molecules, particles or cells to the waste channel. The user is prompted for the threshold voltage of the PMT signal, to identify a molecule, particle or cell for sorting, i.e. diversion to the collection channel and well. A delay time is also set. If the PMT voltage exceeds the set threshold, the driven electrode voltages are swapped and then, after the specified delay time, the voltages are swapped back. The delay allows the selected molecule, particle or cell enough time to travel down the collection channel so that it will not be redirected or lost when the voltages are switched back. As described above, a slight gradient is maintained in the waste channel, when the voltages are switched, to provide continuity in the flow. This is not strong enough to keep the molecule, particle or cell moving into the other or "off" channel it if is too close to or is still at the branch point.

The value of this delay depends primarily on the velocity of the molecules, particles or cells, which is usually linearly dependent on the voltage gradients. It is believed that momentum effects do not influence the delay time or the sorting process. The molecules, particles or cells change direction almost instantaneously with changes in the direction of the voltage gradients. Unexpectedly, experiments have so far failed to vary the voltages faster than the particles or cells can respond. Similarly, experiments have so far shown that the dimensions of the channels do not effect the delay, on the distance and time scales described, and using the described electronics. In addition the speed with which the cells change direction even at high voltage gradients is significantly less than needed to move them down the appropriate channel, when using a forward sorting algorithm.

Once the voltage and delay value are entered the program, it enters a sorting loop, in which the ADC of the Lab PC 1200 card is polled until the threshold value is exceeded. During that time, the flow of particles or cells is directed into one of the channels, typically a waste channel. Once the threshold is detected, the above voltage switching sequence is initiated. This directs a selected cell or particle (usually and most preferably one at a time) into the other channel, typically a collection channel. It will be appreciated that the cells or particles are being sorted and separated according to the threshold criteria, without regard for which channel or well is considered "waste" or "collection". Thus, molecules or cells can be removed from a sample for further use, or they can be discarded as impurities in the sample.

After the switching cycle is complete (i.e. after the delay), the program returns to the ADC polling loop. A counter has also been implemented in the switching sequence which keeps track of the number of times the switching sequence is executed during one run of the program. This should represent the number of molecules, cells or particles detected and sorted. However, there is a statistical chance that two molecules, cells or particles can pass through simultaneously and be counted as one. In this embodiment, the program continues in this polling loop indefinitely until the user exits the loop, e.g. by typing a key on the computer keyboard. This sets the DACs (and the electrodes) to zero volts, and the sorting process stops.

Reverse Sorting. The reverse sorting program is similar to the forward sorting program, and provides additional flexibility and an error correction resource. In the event of a significant delay in changing the direction of flow in response to a signal to divert a selected molecules, cell or particle, for example due to momentum effects, reversible sorting can change the overall direction of flow to recover and redirect a molecule, cell or particle that is initially diverted into the wrong channel. Experiments using the described electrode array show a delay problem and an error rate that are low enough (i.e. virtually non-existent), so that reversible sorting does not appear necessary. The algorithm and method may be beneficial, however, for other embodiments such as those using pressure driven flow, which though benefitting from an avoidance of high voltages, may be more susceptible to momentum effects.

If a molecule or cell is detected for separation from the flow, and switching is not fast enough, the molecule or cell will end up going down the waste channel with all of the other undistinguished cells. However, if the flow is stopped as soon as possible after detection, the molecule or cell will not go too far. A lower driving force can then be used to slowly drive the particle in the reverse direction back into the detection window. Once detected for a second time, the flow can be changed again, this time directing the molecule or cell to the collection channel. Having captured the desired molecule or cell, the higher speed flow can be resumed until the next cell is detected for sorting. This is achieved by altering the voltages at the electrodes, or altering the analogous pressure gradient, according to the principles described above.

To move molecules or cells at higher velocities, for faster and more efficient sorting, higher voltages may be needed, which could be damaging to molecules or cells, and can be fatal to living cells. Preliminary experiments indicate that there may be a limit to the trade-off of voltage and speed in an electrode driven system. Consequently, a pressure driven flow may be advantageous for certain embodiments and applications of the invention. Reversible sorting may be advantageous or preferred in a pressure driven system, as hydraulic flow switching may not be done as rapidly as voltage switching. However, if a main or waste flow can move fast enough, there may be a net gain in speed or efficiency over voltage switching even though the flow is temporarily reversed and slowed to provide accurate sorting. Pressure driven applications may also offer wider flexibility in the use of buffers or carriers for sample flow, for example because a response to electrodes is not needed.

6.13. Diagnosis of Tuberculosis

A method for DNA fingerprinting is disclosed, and is particularly suitable for forensic identification (e.g. by VNTR), bacterial typing and humam or animal pathogen diagnosis. The method applies restriction length polymorphism using synthetically generated polynucleotide fragments. This method may be used with PCR, but in preferred embodiments PCR is not required.

In this example, the invention is applied to diagnosing the presence of the tuberculosis bacteria (TB). A short sequence of the TB genome, e.g. 20–50 bp (base pairs), is selected that is a fixed distance from a restriction site. This sequence and its relationship to the restriction site are known or statistically predicted to be unique or strongly characteristic of TB and can serve to distinguish TB from other organisms, alone or in combination with other sequences and/or restriction sites. Thus, additional short sequences can be selected in relation to the same or different restriction sites, in order to increase statistical discrimination. In this way, a unique fingerprint of DNA fragments can be constructed.

To identify the bacteria, a single-stranded DNA oligolnucleotide is synthesized to complement the sequence of each short fragment. The sample DNA to be identified is denatured, and is combined with the oligonuclotides, triphosphates and DNA polymerase. Some of the nucleotides should be fluorescently labeled to serve as a reporter. A strand of fluorescent DNA will be synthesized, which can be cut at the restriction site to yield a fragment of fixed length. The resulting DNA fragments can then be sized in any suitable way, for example by gel electrophoresis, or the microfabricated technologies described herein, or both. The use of microfabricated devices is preferred. These devices are fast (10 minutes) and require only femtograms of sample DNA, i.e. only a few thousand molecules. If multiple oligonucleotides are made, the reactions can be multiplexed, for example all of the oligonucleotides can be combined with the sample DNA in one test tube.

6.14. DNA Fingerprinting

This example demonstrates construction a synthetic fingerprint of a DNA sample and identification of a sample. The method can be varied in a number of ways that will be apparent to the practitioner. For example, post-staining with an intercalating dye can be used in place of labeled nucleotides. Suitable dyes include those that are specific to double stranded polynucleotides or DNA (e.g. picogreen from Molecular Probes, Inc.). Alternatively, single stranded DNA can be digested, for example using a single-strand specific nuclease. Another variation is to use affinity purification to pull down the fragment of interest, for example using biotinylated oligonucleotides and streptavidin magnetic coated beads.

DNA samples are denatured or digested with a specific restriction enzyme, such as Bgl II, EcoR I, Hind III or Xho I in the presence of a buffer, according to the instructions from the manufacturer. This can be done at about 34° C. for about 1 minute. Multiple digestions may be done and a final mixture of thousands of base pairs is preferred. The DNA fragments are then extended with primers and fluorescent nucleotides. If the buffer used for digestion is not compatible with DNA extension, another buffer may be used, or dialysis or ethanol precipitation can be conducted.

The DNA extension is accomplished by first preparing a 10× primer solution (1 $\mu$M) and a 10× nucleotide mix comprising 250 $\mu$M dATP, 500 $\mu$M fluorescein-dATP (from NEN), and 750 $\mu$M dTTP, dCTP and dGTP. The DNA sample is then diluted in TE buffer to get a final 10× concentration of about 5–50 ng/$\mu$l. This strongly depends on the average size of DNA fragments in the digestion sample and also the relative amount of DNA fragments (templates) that will hybridize with the primers. Generally speaking, about 1 nM of DNA templates (10×) gives optimum results. DNA extension can be done at about 68° C. for about 2 hours.

The following solutions are made:

| Mix 1 | Mix 2 (Gibco Elongase Enzyme Mix) (total 100 $\mu$l) |
|---|---|
| 2 $\mu$l ultra-pure water | 16 $\mu$l 5X Buffer A |
| 1 $\mu$l of 10x nucleotide mix | 24 $\mu$l Buffer B |
| 1 $\mu$l of 10x primer | 4 $\mu$l Elongase Enzyme Mix (Gibco) |
| 1 $\mu$l of 10x DNA samples | 56 $\mu$l of ultra-pure water |

Buffer A and Buffer B are from the Gibco Elongase Enzyme Package. Then, combine equal volumes of Mix 1 and Mix 2 and mix well. 100 $\mu$l of Mix 2 can be used for about 20 different DNA samples (in Mix 1). Therefore, the total volume of Mix 2 can be adjusted according to the number of DNA samples to be run.

Following these procedures, a polymerase reaction is run for 1 minute at 96° C. for denaturing, for 1 minute at 55° C. for annealing and for 1 hour at 68° C. for extension. The annealing time and temperature may vary, depending on the primer used in Mix 1. The PCR reaction and conditions can be optimized or modified according to techniques known in the art.

Preferably, only one reaction is performed. Successive rounds of PCR amplification are not needed. Dialysis or a spin column is then used to clean out unused fluorescent single nucleotides (fluorescein-dATP).

After the extension reaction is run the fluorescent-labeled DNA samples are diluted to about 100 fM (1,000 times for a 10× template with a concentraion of 1 nM). Then 10 μl of the diluted sample is run on the SMS system described above, using 10 mW laser power and 2,450-volt APD bias for 10 to 30 minutes. The data is analyzed using a DNA size distribution or threshold method according to a pre-selected fluorescent level, as described above.

6.15. Identification of T7 DNA

This example demonstrates construction of a synthetic fingerprint from the genome of T7 phage, and identification of a sample, according to the methods of Example 14. An oligonuceotide primer specific to T7 phage was used, fluorescent fragments were generated, and these were sized in an SMS device of the invention. Control tests using the T7 olignucleotide primer as the fingerprint with a lambda phage sample showed virtually no signal in the SMS device of Example 9.

In this example, with T7 and λ, digestion was not needed and was not done, because the DNA fragments were already of fixed length. The DNA fragments are extended with primers and fluorescent nucleotides. Dialysis was done at 4° C. for 3 hours using a 5 μl sample in 10 ml of TE buffer. After dialysis a 10× dilution in TE buffer was done (i.e. by adding 45 μl of TE buffer).

The DNA extension is accomplished by first preparing a 10× primer solution 1 μM and a 10× nucleotide mix comprising 250 μM dATP, 500 μM fluorescein-dATP (from NEN), and 750 μM dTTP, dCTP and dGTP. The DNA sample is then diluted in TE buffer to get a final 10× concentration of about 5–50 ng/μl. This strongly depends on the average size of DNA fragments in the digestion sample and also the relative amount of DNA fragments (templates) that will hybridize with the primers. Generally speaking, about 1nM of DNA templates (10×) gives optimum results. DNA extension can be done at about 68° C. for about 2 hours.

Mix 1 and Mix 2 were made as in Example 14. Then, 5 μl of Mix 2 was added to Mix 1 and they are mixed well.

In this example the following T7 primer was used, which binds to T7 at base position 588:

5'-CATTGACAACATGAAGTAACATGCAGTAAGA-3'
(SEQ. ID. NO. 1).

Following these procedures, a polymerase reaction is run for 1 minute at 96° C. for denaturing, for 1 minute at 60° C. for annealing and for 2 hours at 68° C. for extension. In this example, 0.5 μl of a 100 μl solution of Taq polymerase was used. Only one reaction is performed. Successive rounds of PCR amplification are not needed. Dialysis or spin column is then used to clean out unused fluorescent single nucleotides (fluorescein-dATP). After the extension reaction is run the fluorescent-labeled DNA samples are diluted to about 100 fM. Then 10 μl of the diluted sample is run on the SMS system, using 10 mW laser power and 2,450-volt APD bias for 10 to 30 minutes. The data is analyzed using DNA size distribution or threshold method according to a pre-selected fluorescent level.

For analysis using a microfabricated device of the invention, a sample solution was diluted by a factor of two. The device comprised a T-shaped set of channels about 3 μm wide and about 1.75 μm deep in an elastomer substrate. This chip was treated with HCl to render it hydrophillic. The device, as described in Example 9, used a laser with 3.5 mW of power (488 nm) with a 2,450 V APD detector bias.

Figure 13:
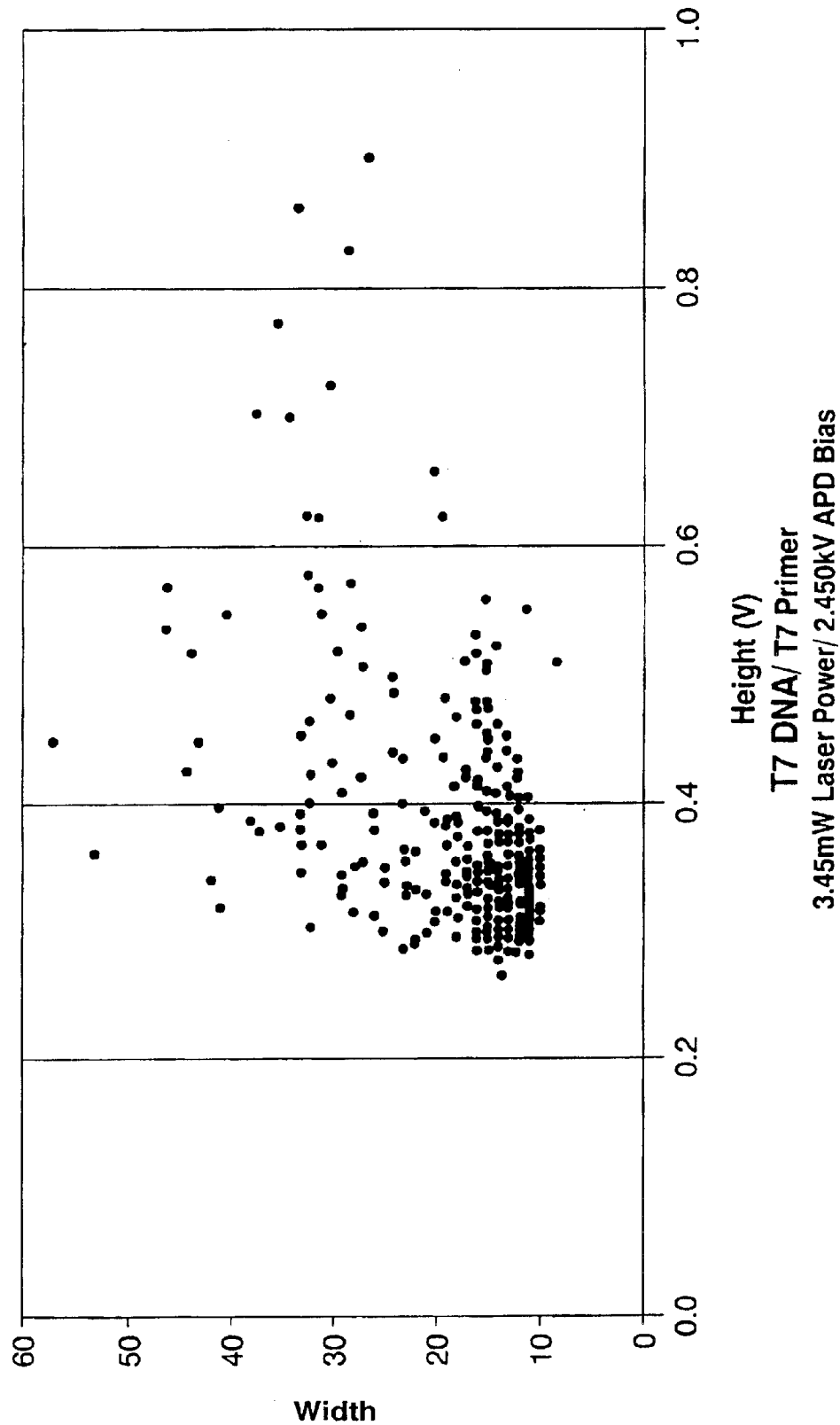
FIG. 13 shows the results a comparison between a fingerprint for T7 phage and a known T7 sample, using the method and a microfabricated device of the invention.
Figure 14:
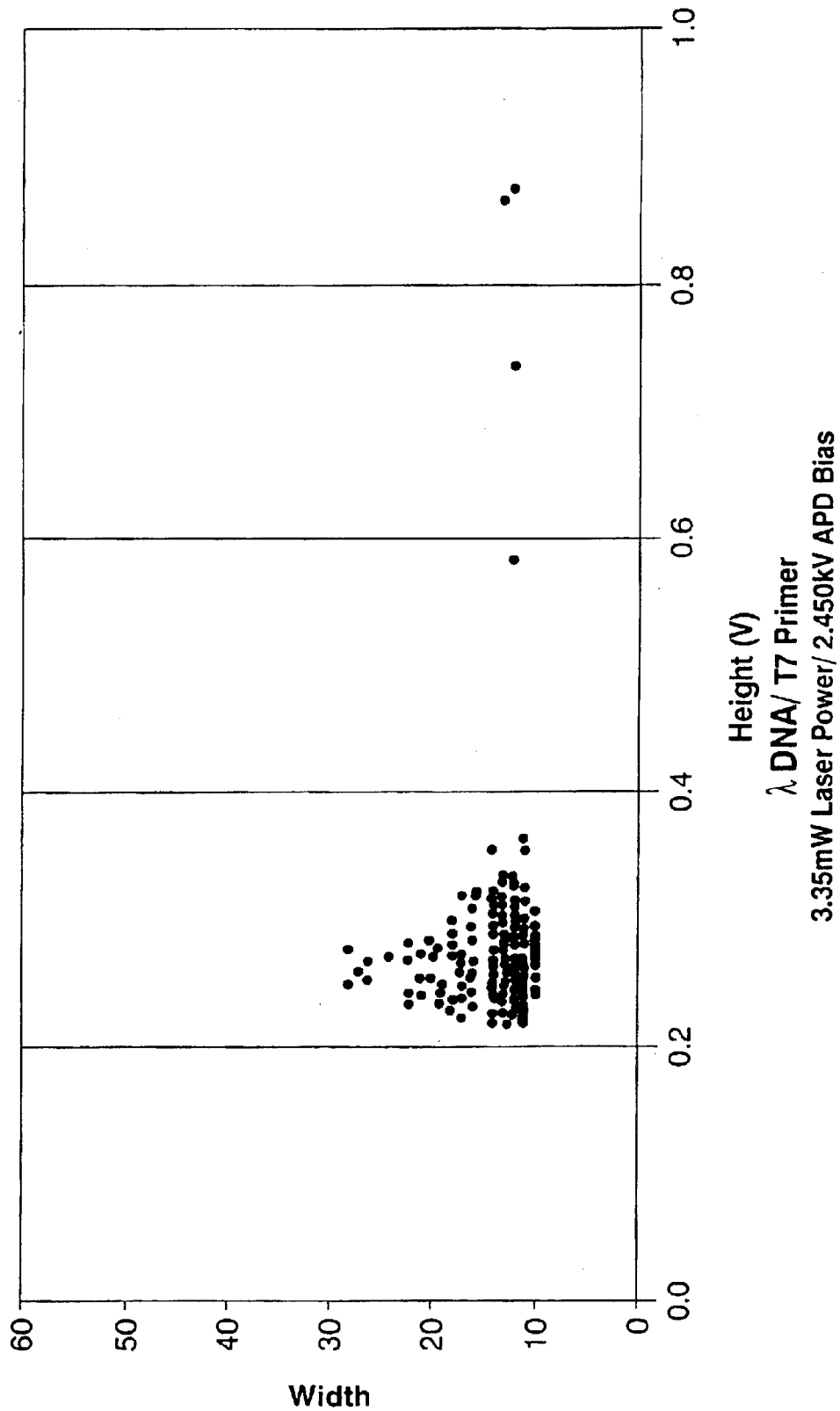
FIG. 14 shows the results a comparison between a fingerprint for T7 phage and a known lambda phage sample, using the method and a microfabricated device of the invention.
Figure 15:
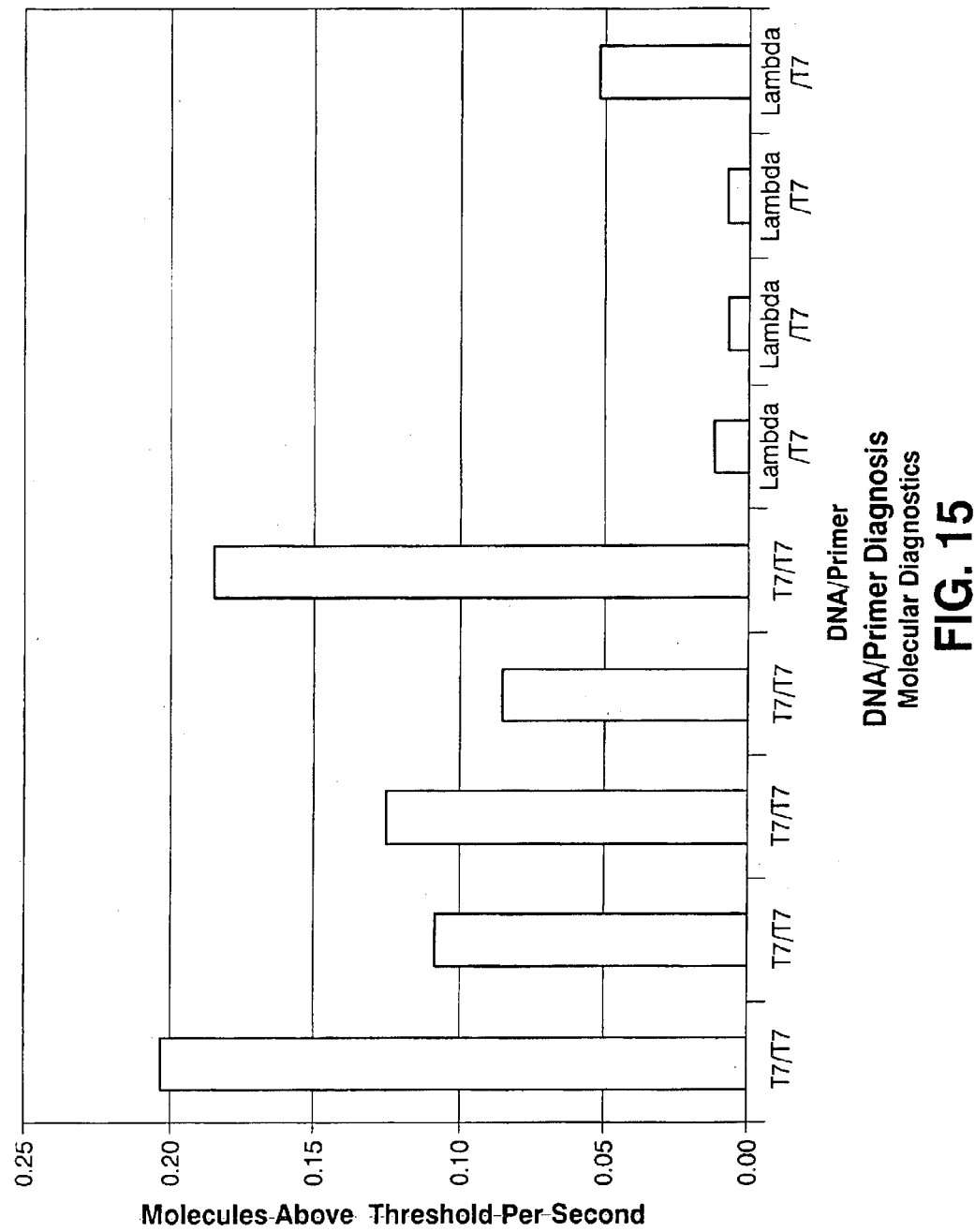
FIG. 15 shows a comparison between a T7 phage sample and a lambda phage sample against a T7 fingerprint, using a threshold detection algorithm in a microfabricated device of the invention.

The above procedure was repeated with an unknown test sample, which comprised either T7 phage DNA (which should match) or lambda phage (which should not match). The sizing results for the test sample were compared against the T7 phage standard. The results of the T7 v. T7 experiment are shown in FIG. 13. The results of the T7 v. lambda phage experiment are shown in FIG. 14. These results are compared in FIG. 15, showing strong signals for the T7 matching T7, and weak signals for lambda, which does not match T7. As shown, there is a clearly a distinguishable signal between the T7 and lambda results. FIG. 13 shows many brightly fluorescent DNA fragments that are relatively long (match), compared to the relatively short and dull fragments of FIG. 14 (no match). These differences can be readily detected based on a preset threshold, as shown in FIG. 15. The results shown in the figures were obtained with 5–10 minutes of run time on the SMS device of the invention.

6.16. Preferred Systems and Embodiments for Molecular Fingerprinting

This Example describes, in general terms, preferred embodiments of the molecular fingerprinting assays that are described and demonstrated elsewhere in this application (see, for instance, the Examples presented in Sections 6.13–6.15, supra). The description of these methods is made by way of non-limiting examples. Accordingly, the skilled artisan will appreciate that many variations of these methods may be practiced without departing from the spirit of the present invention. For example, many of the specific steps described above may be eliminated and, moreover, the steps need not necessarily be performed in the particular sequential order(s) recited herein.

Using the methods described herein, a skilled artisan may readily analyze any sample, e.g., to detect a particular nucleic acid and to thereby determine whether that particular nucleic acid is present in the sample. For example, the methods of the invention may be used to analyze samples of cells or tissue (or samples of nucleic acid derived therefrom) to determine whether a particular nucleic acid is present in the cells or tissue. In one embodiment, the methods may be used to determine whether the cells or tissue express a particular nucleic acid. In another embodiment the particular nucleic acid may be a nucleic acid from a pathogen (e.g., from an infectious agent such as a virus or bacteria), and the fingerprinting methods of this invention may be used to determine whether the cells or tissues are infected with that pathogen.

In other embodiments, the methods of the invention may be used to analyze a sample derived from an individual (e.g., a clinical sample derived from a patient). For example, the molecular fingerprinting methods of this invention may be used to analyze a cell or tissue sample from an individual or, more preferably, a sample or nucleic acids derived from such cells or tissue. In such embodiments the molecular fingerprinting methods of the invention may be used, e.g., as a diagnostic method (e.g., to detect a nucleic acid or nucleic acids characteristic of a particular pathogen), as part of a therapeutic methods (e.g., to monitor expression of a certain gene or genes during a therapy) or as a forensic method (for example, paternity testing) to name a few applications.

In preferred embodiments, the methods of this invention are used to detect or analyze single stranded nucleic acids within a sample. Accordingly, a nucleic acid sample analyzed according to the invention will preferably be a sample of single-stranded nucleic acid molecules. However, samples containing double-stranded nucleic acids may also be analyzed. In such embodiments, the sample is preferably denatures (e.g., by heat) or otherwise exposed to conditions in which the complementary nucleic acids separate to produce single-stranded nucleic acid.

The skilled artisan will readily appreciate that the methods of this invention may be used to analyze and/or detect any type of nucleic acid in a sample. Thus, although the specific examples presented herein frequently describe the invention in terms of detecting or analyzing DNA, the invention may also be used to detect and/or analyze RNA. Indeed, any type of synthetic or naturally occurring nucleic acid may be analyzed and/or detected using the invention, including but not limited to the various types recited, supra, in Section 5.1.

In preferred embodiments, therefore, the invention is used to detect a particular nucleic acid, referred to here as the "target" nucleic acid, in a sample. Preferably, the base sequence of the target nucleic acid detected with this invention will be at least partly known. More preferably, the known (or partly known) sequence will comprise at least one sequence that is recognized by a particular "cleavage agent". The term cleavage agent, as used herein, refers to any agent (e.g., any enzyme, chemical or other substance) that is able to cut or cleave a nucleic acid molecule into two or more fragments. In preferred embodiments, each cleavage agent used in the methods and compositions of this invention will recognize a specific (and preferably different) nucleic acid sequence; i.e., each cleavage agent preferably has a specific recognition site (also referred to herein as the "cleavage site" or the "restriction site"). Recognition sites that are four bases in length are preferred. However, the invention is not limited to recognition sites of any particular length. Indeed, in embodiments where a plurality of different cleavage agents are used, the different cleavage agents may have recognition sites of different lengths.

In particularly preferred embodiments, a cleavage agent used in the invention is a restriction enzyme. Restriction enzymes are well known in the art and may be readily obtained, e.g., from a variety of commercial sources (for example, Promega Corp., Madison, Wis.). Similarly, methods for using restriction enzymes are also generally well known and routine in the art. See, for example, the references cited in Section 5.1, supra, for general molecular biology techniques. Preferred restriction enzymes are ones that cut nucleic acids by recognizing a specific sequence of bases (i.e., the recognition site). Typically, the recognition site for a restriction enzyme will be about 4, 5 or 6 nucleotides in length. A cut is typically made within the recognition site. Therefore the location of the cut in a nucleic acid having a known recognition site will also be known.

In one preferred, exemplary embodiment of the invention, a primer is selected or chosen (e.g., by a user) which is able to bind or hybridize to the target nucleic acid under suitable conditions and at a specific, known or predetermined location in the target nucleic acid sequence. In particular, the primer preferably binds or hybridizes to the target nucleic acid at a location that is a known or predetermined distance from the restriction site; i.e., at a site that is a specific number of bases away from the restriction site. Generally, the primer is a nucleic acid that is complementary to a particular sequence of the target nucleic acid molecule and is therefore capable of hybridizing to that complementary sequence under appropriate hybridization conditions. In preferred embodiments, the primer is an oligonucleotides between about 4 and about 100 bases in length, more typically about 10–100 bases in length and preferably between about 20–50 bases in length.

A suitable primer having been selected, chosen or otherwise obtained, the primer is then contacted to the nucleic acid sample under suitable conditions so that the primer binds to the target nucleic acid at the predetermined location. The sample, with the primer, is then incubated with a polymerase and a plurality of nucleotides under conditions such that primer extension can occur, e.g., by adding nucleotides to the primer and using the target nucleic acid as a template, thereby generating a second nucleic acid molecule that is complementary to the target nucleic acid. Typically, the plurality of nucleotides will include one or more nucleotides that are detectably labeled (e.g., with a reporter) so that the primer extension product, or a fragment thereof, may be detected by detecting the reporter.

In one embodiment, the primer extension reaction continues to the end of the target nucleic acid. However, in preferred embodiments primer extension need only continue up to at least the restriction site so that the complementary nucleic acid that is generated by the primer extension also contains the restriction site. Generally, polymerases synthesize polynucleotides beginning at the 3'-end of a polynucleotide primer and moving in the 3'-direction. Thus, in preferred embodiments of the invention, a primer is chosen that hybridizes to a sequence of the target nucleic acid that is situated a particular known distance upstream (i.e., in the 3'-direction) from the restriction site on the single-stranded target nucleic acid.

Having generated a nucleic acid that is complementary to the target nucleic acid and contains the target nucleic acid's restriction site (or a complement thereof), the complementary nucleic acid may also be cut or cleaved by a cleavage agent (e.g., a restriction enzyme) which recognizes the particular restriction site. Because synthesis of the complementary nucleic acid beings a fixed, predetermined distance from the restriction site, using the cleavage agent to cut or cleave the complementary nucleic acid gives rise to a fragment having a known length; namely, the length of the known, fixed distance from the restriction site to the position on the target sequence where the primer hybridizes and primer extension begins.

Accordingly, in preferred embodiments the cleavage agent is next contacted to the sample so that the target sequence and/or the complementary sequence are cut or cleaved, thereby generating a fragment or fragments having the fixed known length. In one embodiment, the cleavage agent is contact to the sample without denaturing the polynucleotides; i.e., so that the target and complementary nucleic acids are hybridized to each other and are therefore double stranded. However, in an alternative embodiment the cleavage agent is able to specifically recognize the restriction site in the single-stranded complementary nucleic acid, and the two strands are separated (e.g., by heating the sample) before contacting the cleavage agent.

A user may then readily determine whether the target nucleic acid is present in the sample by detecting fragments of the known fixed length. For instance, in preferred embodiments where primer extension is performed using detectably labeled nucleotides (e.g., with a reporter), the fragments may be readily detected by separating polynucleotides in the sample according to length and detecting the reporter. A variety of techniques are known in the art for separating polynucleotides by their length or size and any of these techniques may be used in the present invention. Exemplary, non-limiting techniques include gel electrophoresis, high performance liquid chromatography (HPLC) and mass spectroscopy. However, in particularly preferred embodiments polynucleotides are sorted according to size using a microfluidic device of the present invention, e.g., according to any of the polynucleotide sorting algorithms described supra.

A skilled artisan will recognize that the above-described methods may be readily adapted to various nucleic acid amplification techniques such as the polymerase chain reaction (PCR). For example, many different copies of a single primer may be repeatedly contacted to the sample followed by repeated primer extension reactions so that a plurality of complementary nucleic acids are obtained. Alternatively, sense and antisense primers may be designed to amplify a particular subsequence of the target nucleic acid which contains the restriction site. Contacting the cleavage agent with the resulting amplification products will then produce fragments having a specific, predetermined size and these fragments may be detected as described above.

The methods of the invention are ideally suited however, to performing only a single round of primer extension so that a single complementary nucleic acid is created and a single fragment is detected. Single nucleic acid fragments may be readily detected, e.g., using a microfluidic device of the invention to sort polynucleotides one molecular at a time, as described supra. Moreover, these methods are particularly advantageous since analysis may be performed using small samples and without undergoing complicated thermocycling that is required, e.g., for PCR. As result, the molecular fingerprinting methods of this invention are ideally suited for "lab on a chip" devices (described supra) that comprise a single microfluidic device. In such devices, the entire sequence of primer extension, strand cleavage and fragment detection may be performed using a single microfluidic device or kit and such kits are therefore considered to be part of the present invention.

A skilled artisan will also readily appreciate that steps of these molecular fingerprinting methods may be performed in a variety of different sequences. For example, in one alternative embodiment the nucleic acid sample may be contacted with a cleavage agent before implementing primer extension. In such embodiments, the primer will then hybridize to a nucleic acid fragment generated when the target nucleic acid is cut or cleaved with the cleavage agent. In particular, the primer preferably hybridizes to this fragment a known, predetermined distance from the fragment's end (i.e., from the cut site). As a result, primer extension occurs from the primer and along the target sequence to the cut site, and a complementary fragment having the known, predetermined length is thereby obtained.

Those skilled in the art will further appreciate that variations of the above-described methods may be performed using a plurality of different primers. Preferably, each primer will hybridize to a different sequence within the target nucleic acid, each different sequence being a known but different distance from the target nucleic acid's restriction site. In such variations of the invention, a plurality of primer extension reactions may be implemented (preferably at least one for each different primer) either sequentially or at the same time, and the different extension products may then be cleaved with the cleavage agent. A plurality of fragments having different predetermined lengths are then produced, and these fragments may be separated according to their size and detected as described, above.

It will be appreciated by persons of ordinary skill in the art that the examples and preferred embodiments herein are illustrative, and that the invention may be practiced in a variety of embodiments which share the same inventive concept.

7. REFERENCE CITED

Numerous references, including patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification and/or listed here below are incorporated herein by reference in their entirety and to the same extent as if each reference was individually incorporated by reference.

BIBLIOGRAPHY

1. J. P. Nolan, L. A. Sklar, *Nature Biotechnology* 16, 633 (1998).
2. P. J. Crosland-Taylor, *Nature (London)* 171, 37 (1953).
3. U.S. Pat. No. 2,656,508 issued to Coulter (1949).
4. L. A. Kamensky, M. R. Melamed, H. Derman, *Science* 150, 630 (1965).
5. A. Moldavan, *Science* 80, 188 (1934).
6. M. A. Van Villa, T. T. Trujillo, P. F. Mullaney, *Science* 163, 1213 (1969).
7. M. A. Van Villa, et al., *A fluorescent cell photometer: a new method for the rapid measurement of biological cells stained with fluorescent dyes*. (Biological and Medical Research Group of the Health Division, LASL., 1997).
8. M. J. Fulwyer, *Science* 156, 910 (1974).
9. H. M. Shapiro, *Practical Flow Cytometry* (Wiley-Liss Inc., New York City, 1995).
10. M. R. Melamed, T. Lindmo, M. L. Mendelsohn, *Flow Cytometry and Sorting* (Wiley-Liss Inc., New York City, 1990).
11. G. Whitesides, Y. Xia, *Angewandte Chemie International Edition* 37, 550 (1998).
12. P. H. Li, D. J. Harrison, *Analytical Chemistry* 69, 1564 (1997).
13. S. Fiedler, et al. *Analytical Chemistry* 70, 1909–1915 (1998).
14. L. A. Sklar, *Proc. SPIE* 3256, 144 (1998).
15. H. P. Chou, A. Scherer, C. Spence, S. R. Quake, Proc. Natl. Acad. Sci. USA 96: 11–13 (1998).
16. A. Ashkin, J. M. Dziedzic, *Science* 235, 1517 (1987).
17. A. Ashkin, J. M. Dziedzic, *Nature* 330, 769 (1987).
18. T. N. Buican, M. J. Smyth, H. A. Verissman, *Applied Optics* 26, 5311 (1987).
19. C. Spence, S. R. Quake, "Transformation of cells with DNA sorting on microchips."; personal communication, 1998.
20. R. V. Hare, "Polyvinylsiloxane impression material."; U.S. Pat. No. 5,661,222, 1997.
21. M. U. Kopp et al., *Science*, 280:1046 (1998)
22. D. J. Harrison et al., *Science*, 261:895 (1993)
23. J. P. Brody, "Valveless Microswitch, U.S. Pat. No. 5,656,155 (1998).
24. Aine, H. E., et al., U.S. Pat. No. 4,585,209 (1986).
25. Baker, D. R., in Capillary Electrophoresis, John Wiley Sons, New York, 1995.
26. Ballantyne, J. P., eL al., J. Vac. Sci. Technol. 10:1094 (1973).
27. Castro, A., et al., Anal. Chem. 85:849–852 (1993).
28. Goodwin, P. M., et: al., Nucleic Acids Research 21(4):803–806 (1993).
29. Gravesen, P., et: al., U.S. Pat. No. 5,452,878 (1995).

30. Haugland, R. P., in Handbook of Fluorescent Probes and Research Chemicals, 5th Ed., Molecular Probes, Inc., Eugene, Ore. (1992).

31. Keller, R. A., et al., GB Patent No. 2,264,296 (10/95).

32. Krutenat, R. C., Kirk-Othmer Concise Encyclopedia of Chemical Technology, John Wiley & Sons, New York (1985).

33. O'Connor, J. M., U.S. Pat. No. 4,581,624 (1986).

34. van Lintel, H. T. G., U.S. Pat. No. 5,271,274 (1993).

35. Wise, K. D., et al., U.S. Pat. No. 5,417,235 (1995).

36. Thompson, L. F., "Introduction to Lithography", ACS Symposium Series 219:1–13, (1983).

37. Angell et al., Scientific American 248:44–55 (1983).

38. Manz et al., Trends in Analytical Chemistry 10:144–149 (1991)

39. Harrison et al., International Publication No. 98/52691, published Nov. 26, 1998.

40. Bein, Thomas, Efficient Assays for Combinatorial Methods for the Discovery of Catalysts, *Angew. Chem Int. Ed*. 38:3, 323–26 (1999).

41. F. H. Arnold, *Acct. Chem. Research*31, 125–131 (1998).

42. Hanes, J. & Pluckthun A. *Proc. Natl. Acad. Sci., USA* 94, 4937 (1997).

43. Hoffmuller, U. & J. Schneider-Mergener, *Angew. Chemie. Int. Ed*. 37, 3241–3243 (1998).

44. Jermutus, L., L. A. Ryabova & A. Pluckthun, *Curr. Opin. Biotechnol*. 9, 534–548 (1998).

45. Roberts, R. W. & Szostak, J. W. *Proc. Natl. Acad. Sci USA* 94, 12297–12302 (1997).

46. Stemmer, W. P. C. Nature, 370, 389 (1994).

47. Tawfik, D. and Griffiths, A. *Nat. Biotechnol*. 16, 656 (1998).

48. Sambrook et al., *Molecular Cloning: A Laboratory Manual 2$^{nd}$ Edition*, Cold Spring Harbor Laboratory Press (1989).

49. Benecke et al., U.S. Pat. No. 5,454,472 (1995).

50. J. Affholter and F. Arnold, "Engineering a Revolution," *Chemistry in Britain*, April 1999, p.48.

51. H. Joo, Z. Lin and F. Arnold, "Laboratory evolution of peroxide-mediated cytochrome P450 hydroxylation," *Nature* 399, 670–673 (1999).

52. Inoue, Shinya and Spring, Kenneth R.,Video Microscopy: The Fundamentals, 2$^{nd}$ ed., Plenum Press, New York, N.Y. (1997).

53. Giusti, J. Forensic Sci. 31:409–417 (1986).

54. Kanter et al, J. Forensic Sci. 31:403–408 (1986).

55. Jeffreys et al., Nature 314:67–72 (1985).

56. Budowle et al., Am. J. Hum. Genet. 48:137–144 (1991).

57. Nakamura et al., Science 235:1616–22 (1987).

58. Crow et al., "The Evaluation of Forensic DNA Evidence," National Academy Press (1996).

59. Quake et al., "A Microfabricated Device for Sizing and Sorting DNA Molecules," PNAS 96:11–13 (1999).

What is claimed is:

1. A method for detecting a particular nucleic acid in a sample, which particular nucleic acid has at least one restriction site, and which method comprises:

(a) contacting the sample with
   (i.) a primer that hybridizes to the particular nucleic acid a predetermined distance from the restriction site,
   (ii.) a polymerase and
   (iii.) a plurality of nucleotides, so that a complementary nucleic acid is synthesized from the primer at least to the restriction site;

(b) contacting the complementary nucleic acid with a restriction enzyme under conditions capable of cutting the complementary nucleic acid at the restriction site; and (c) detecting a nucleic acid fragment having a particular length equal to the fixed distance by a method that comprises:
   (i) sorting polynucleotide molecules in the sample according to size in a device for processing a flow of polynucleotide molecules, which device comprises a substrate and an analysis unit, wherein the analysis unit comprises:
      a main channel having a polynucleotide sample inlet, a detection region downstream of the sample inlet and a branch point discrimination region adjacent to and downstream of the detection region, wherein on average one polynucleotide molecule at a time is placed within the detection region;
      at least two branch channels originating at the branch point discrimination region and in communication with the main channel;
      a detector sensitive to polynucleotide molecules passing through the detection region; and
      a flow control responsive to the detector and acting to direct polynucleotide molecules at the discrimination region into a selected branch channel; and
   (ii) identifying a polynucleotide having the particular length, wherein the presence of the nucleic acid fragment in the sample indicates that the particular nucleic acid is present in the sample.

2. A method according to claim 1 wherein the channels of the device are about 1–100 µm in depth.

3. A method according to claim 1 wherein the detection region of the device has a volume between about 1 femtoliter and 1 nanoliter.

4. A method according to claim 1 wherein:
   at least some of the plurality of nucleotides are detectably labeled, and
   polynucleotides are directed to a selected branch channel based on a measured level of the detectable label.

5. A method according to claim 4 wherein the labeled nucleotides are fluorescently labeled.

6. A method for detecting a particular nucleic acid in a sample, which particular nucleic acid has at least one restriction site, and which method comprises:
   (a) contacting the sample with a restriction enzyme under conditions capable of cutting the particular nucleic acid at the restriction site;
   (b) contacting the sample with a primer that hybridizes to the nucleic acid a predetermined distance from the cut at the restriction site, a polymerase and a plurality of nucleotides, so that a complementary nucleic acid fragment is synthesized; and
   (c) detecting the complementary nucleic acid fragment using a device for processing a flow of polynucleotide molecules, which device comprises a substrate and an analysis unit,
      wherein the analysis unit comprises:
         a main channel having a polynucleotide sample inlet, a detection region downstream of the sample inlet and an outlet region adjacent to and downstream of the detection region; and a detector sensitive to polynucleotides passing through the detector region, and where, on average, one polynucleotide at a time is placed within the detection region, wherein the presence of the complementary nucleic acid fragment in the sample indicates that the particular nucleic acid is present in the sample.

7. A method according to claim 6 wherein the channels of the device are about 1–100 µm in depth.

8. A method according to claim 6 wherein the detection region of the device has a volume between about 1 femtoliter and 1 nanoliter.

9. A method according to claim 6 wherein the detector is sensitive to the size of polynucleotide molecules passing through the detection region.

10. A method according to claim 6 wherein:

at least some of the plurality of nucleotides are detectably labeled; and the detector is sensitive to the detectable label.

11. A method according to claim 10 wherein the labeled nucleotides are fluorescently labeled.

12. A method for detecting a particular nucleic acid in a sample, which particular nucleic acid has at least one restriction site, and which method comprises:

(a) contacting the sample with a restriction enzyme under conditions capable of cutting the particular nucleic acid at the restriction site;

(b) contacting the sample with a primer that hybridizes to the nucleic acid a predetermined distance from the cut at the restriction site, a polymerase and a plurality of nucleotides, so that a complementary nucleic acid fragment is synthesized; and (c) detecting the complementary to nucleic acid fragment according to a method that comprises:

(i.) sorting polynucleotide molecules in the sample according to size in which polynucleotide molecules are sorted in a device for processing a flow of polynucleotide molecules, which device comprises a substrate and an analysis unit, wherein the analysis unit comprises:

a main channel having a polynucleotide sample inlet, a detection region downstream of the sample inlet and a branch point discrimination region adjacent to and downstream of the detection region, wherein on average one polynucleotide molecule at a time is placed within the detection region;

at least two branch channels originating at the branch point discrimination region and in communication with the main channel;

a detector sensitive to polynucleotide molecules passing through the detection region; and a flow control responsive to the detector and acting to direct polynucleotide molecules at the discrimination region into a selected branch channel; and (i.) identifying a polynucleotide having the particular length, wherein the presence of the complementary nucleic acid fragment in the sample indicates that the particular nucleic acid is present in the sample.

13. A method according to claim 12 wherein the channels of the device are about 1–100 µm in depth.

14. A method according to claim 12 wherein the detection region of the device has a volume between about 1 femtoliter and 1 nanoliter.

15. A method according to claim 12 wherein:

at least some of the plurality of nucleotides are detectably labeled, and polynucleotides are directed to a selected branch channel based on a measured level of the detectable label.

16. A method according to claim 12 wherein the labeled nucleotides are fluorescently labeled.

* * * * *

UNITED STATES PATENT AND TRADEMARK OFFICE
CERTIFICATE OF CORRECTION

PATENT NO. : 6,833,242 B2
APPLICATION NO. : 09/826373
DATED : December 21, 2004
INVENTOR(S) : Stephen R. Quake et al.

It is certified that error appears in the above-identified patent and that said Letters Patent is hereby corrected as shown below:

Column 1, line 13, before "1. FIELD OF THE INVENTION," insert the following heading and paragraph:

--STATEMENT AS TO RIGHTS TO INVENTIONS MADE UNDER FEDERALLY SPONSORED RESEARCH OR DEVELOPMENT

This invention was made with government support under Grant Nos. DAAH04-96-1-0141 and DAAH04-95-1-0613 awarded by the Army Research Office. The government has certain rights in the invention.--

Signed and Sealed this

Fourteenth Day of April, 2009

JOHN DOLL
*Acting Director of the United States Patent and Trademark Office*